(12) United States Patent
Belyakov et al.

(10) Patent No.: US 8,329,665 B2
(45) Date of Patent: *Dec. 11, 2012

(54) COMPOSITIONS AND METHODS FOR TREATING CANCER

(75) Inventors: Sergei Belyakov, Singapore (SG); Bridget Duvall, Nottingham, MD (US); Dana Ferraris, Eldersburg, MD (US); Gregory Hamilton, Catonsville, MD (US); Mark Vaal, Perry Hall, MD (US)

(73) Assignee: Eisai Inc., Andover, MA (US)

( * ) Notice: Subject to any disclaimer, the term of this patent is extended or adjusted under 35 U.S.C. 154(b) by 36 days.

This patent is subject to a terminal disclaimer.

(21) Appl. No.: 12/755,116

(22) Filed: Apr. 6, 2010

(65) Prior Publication Data

US 2010/0279977 A1    Nov. 4, 2010

Related U.S. Application Data

(60) Provisional application No. 61/167,117, filed on Apr. 6, 2009.

(51) Int. Cl.
 *A61K 31/7072*  (2006.01)
 *A61K 31/7052*  (2006.01)
 *A61P 35/00*  (2006.01)
 *A61P 35/02*  (2006.01)

(52) U.S. Cl. .............................. 514/43; 514/49; 514/50
(58) Field of Classification Search .................... 514/43, 514/49, 50
 See application file for complete search history.

(56) References Cited

U.S. PATENT DOCUMENTS

| | | | |
|---|---|---|---|
| 4,017,606 A | 4/1977 | Hanze et al. | |
| 4,275,057 A * | 6/1981 | Marquez et al. ................ 514/52 |
| 4,526,988 A | 7/1985 | Hertel | |
| 4,808,614 A | 2/1989 | Hertel | |
| 4,965,374 A | 10/1990 | Chou et al. | |
| 5,223,608 A | 6/1993 | Chou et al. | |
| 5,371,210 A | 12/1994 | Chou | |
| 5,426,183 A | 6/1995 | Kjell | |
| 5,464,826 A * | 11/1995 | Grindey et al. ................ 514/50 |
| 5,521,294 A | 5/1996 | Wildfeuer | |
| 5,530,110 A * | 6/1996 | Sowers ....................... 536/28.55 |
| 5,552,539 A | 9/1996 | Duplaa et al. | |
| 5,594,124 A | 1/1997 | Chou | |
| 5,606,048 A | 2/1997 | Chou et al. | |
| 5,637,688 A | 6/1997 | Berglund | |
| 5,821,357 A | 10/1998 | Chou et al. | |
| 5,932,719 A | 8/1999 | Abushanab et al. | |
| 5,945,547 A | 8/1999 | Chou et al. | |
| 5,968,914 A | 10/1999 | Von Borstel et al. | |
| 6,001,994 A | 12/1999 | Weigel | |
| 6,326,491 B1 | 12/2001 | Abushanab et al. | |
| 6,344,447 B2 | 2/2002 | Von Borstel et al. | |
| 6,462,191 B1 | 10/2002 | Lal | |
| 6,933,287 B1 | 8/2005 | Greer | |
| 7,125,983 B2 | 10/2006 | Iizuka et al. | |
| 7,141,576 B2 * | 11/2006 | Lackey et al. ............ 514/264.11 |
| 2004/0063926 A1 | 4/2004 | Iizuka et al. | |
| 2009/0099105 A1 | 4/2009 | Wedekind et al. | |
| 2009/0137521 A1 | 5/2009 | Hamilton et al. | |
| 2009/0325897 A1 | 12/2009 | Greer | |
| 2010/0279966 A1 | 11/2010 | Belyakov et al. | |
| 2010/0279967 A1 | 11/2010 | Belyakov et al. | |

FOREIGN PATENT DOCUMENTS

| | | |
|---|---|---|
| EP | 1 172 369 A1 | 1/2002 |
| EP | 1 348 712 A1 | 10/2003 |
| GB | 2136425 A | 9/1984 |
| WO | WO 85/01871 A1 | 5/1985 |
| WO | WO 92/18517 A1 | 10/1992 |
| WO | WO 94/26761 A1 | 11/1994 |
| WO | WO 94/27632 A1 | 12/1994 |
| WO | WO 00/51639 A2 | 9/2000 |
| WO | WO 02/094844 A2 | 11/2002 |
| WO | WO 2004/028454 A2 | 4/2004 |
| WO | WO 2005/115410 A2 | 12/2005 |
| WO | WO 2006/015346 A1 | 2/2006 |
| WO | WO 2006/063105 A1 | 6/2006 |
| WO | 2008/085611 A2 | 7/2008 |
| WO | WO 2009/021551 A1 | 2/2009 |
| WO | 2009/052287 A1 | 4/2009 |
| WO | WO 2010/047698 A1 | 4/2010 |

OTHER PUBLICATIONS

Goodman and Gilman's "The Pharmacological Basis of Therapeutics", 10th Ed., 1996, p. 54.*
Laliberte et al Cancer Chemother. Pharmacol. 1992, 30, 7-11.*
Bouffard, David Y. et al., "Kinetic Studies on 2',2'-Difluorodeoxycytidine (Gemcitabine) with Purified Human Deoxycytidine Kinase and Cytidine Deaminase," Biochemical Pharmacology, vol. 45(9):1857-1861 (1993).
Laliberte, Josee et al., "Potent inhibitors for the deamination of cytosine arabinoside and 5-aza-2'-deoxycytidine by human cytidine deaminase," Cancer Chemother. Pharmacol., vol. 30:7-11 (1992).
Lemaire, Maryse et al., "Inhibition of cytidine deaminase by zebularine enhances the antineoplastic action of 5-aza-2'-deoxycytidine," Cancer Chemother. Pharmacol., vol. 63:411-416 (2009).
Liu, Paul S. et al., "Cyclic Urea Nucleosides. Cytidine Deaminase Activity as a Function of Aglycon Ring Size," J Med. Chem., vol. 24:662-666 (1981).
Ludek, Olaf R. et al., "Synthesis of conformationally locked carbocyclic 1,3-diazepinone nucleosides as inhibitors of cytidine deaminase," Nucleic Acids Symposium Series, vol. 52:659-660 (2008).
Marquez, Victor E. et al., "Synthesis of 1,3-Diazepin-2-one Nucleosides as Transition-State Inhibitors of Cytidine Deaminase," Journal of Medicinal Chemistry, vol. 23(7):713-715 (1980).

(Continued)

*Primary Examiner* — Shaojia Anna Jiang
*Assistant Examiner* — Ganapathy Kishnan
(74) *Attorney, Agent, or Firm* — Myers Bigel Sibley & Sajovec P.A.

(57) ABSTRACT

Provided herein are compounds used to inhibit the deamination enzyme responsible for the inactivation of therapeutic compounds, and methods of using them.

20 Claims, 12 Drawing Sheets

OTHER PUBLICATIONS

International Search Report and Written Opinion for Application No. PCT/US2010/030081, dated Sep. 7, 2010.
Aduma et al., "Anti-herpes virus activity of 5-methoxymethyl-2'-deoxycytidine in combination with deaminase inhibitors," Antiviral Chem. Chemother. 1(4):255-262 (1990).
Avramis et al., "Pharmacology of combination chemotherapy of cytosine arabinoside (Ara-C) and uracil arabinoside (Ara-U) or tetrahydrouridine (THU) against murine leukemia L1210/0 in tumor-bearing mice," Cancer Invest. 5:293-99 (1987).
Beumer et al., "Concentrations of the DNA methyltransferase inhibitor 5-fluoro-2'deoxycytidine (FdCyd) and its cytotoxic metabolites in plasma of patients treated with FdCyd and tetrahydrouridine (THU)," Cancer Chemother. Pharmacol. 62:363-68 (2008).
Beumer et al., "Modulation by tetrahydrouridine (THU) of gemcitabine (2',2'-difluoro-2'—deoxcycytidine, dFdC) pharmacokinetics, metabolism and bioavailability in mice," Abstract No. 1556, 2007 Amer. Assoc. Cancer Res. Annual Meeting, Los Angeles, CA (Apr. 14-18, 2007).
Beumer et al., "Modulation of gemcitabine (2',2'-difluoro-2'-deoxcycytidine) pharmacokinetics, metabolism, and bioavailability in mice by 3,4,5,6-tetrahydrouridine," Clin. Cancer Res. 14:3529-35 (2008).
Beumer et al., "Pharmacokinetics, metabolism, and oral bioavailability of the DNA methyltransferase inhibitor 5-fluoro-2'-deoxycytidine in mice," Clin. Cancer Res. 12:7483-91 (2006).
Cacciamani et al., "Purification of Human Cytidine Deaminase: Molecular and Enzymatic Characterization and Inhibition by Synthetic Pyrimidine Analogs," Arch. Biochem. Biophys. 290(2):285-92 (1991).
Chabot et al., "Kinetics of deamination of 5-aza-2'-deoxycytidine and cytosine arabinoside by human liver cytidine deaminase and its inhibition by 3-deazauridine, thymidine or uracil arabinoside," Biochem. Pharmacol. 32(7):1327-28 (1983).
Chou et al., "Stereospecific Synthesis of 2-Deoxy-2,2-difluororibonolactone and Its Use in the Preparation of 2'-deoxy-2',2'-difluoro-β-D-ribofuranosyl Pyrimidine Nucleosides: The Key Role of selective Crystallization," Synthesis pp. 565-570 (Jun. 1992).
Cohen et al., "The Equilibrium of Hydrolytic Deamination of Cytidine and N-Methylcytidine," J. Biol. Chem 246(24):7566-68 (1971).
Cristalli et al., "Diazepinone nucleosides as inhibitors of cytidine deaminase," Nucleosides Nucleotides 15:1567-80 (1996).
Desimone et al., "Tetrahydrouridine, cytidine analogs, and hemoglobin F," Am. J. Hematol. 18:283-88 (1985).
Dover et al., "5-Azacytidine increases HbF production and reduces anemia in sickle cell disease: dose-response analysis of subcutaneous and oral dosage regimens," Blood 66:527-32 (1985).
Eliopoulos et al., "Drug resistance to 5-aza-2'-deoxycytidine, 2',2'-difluorodeoxycytidine, and cytosine arabinoside conferred by retroviral-mediated transfer of human cytidine deaminase cDNA into murine cells." Cancer Chemother. Pharmacol. 42:373-78 (1998).
Goodman and Gilman's "The Pharmacological Basis of Therapeutics," 10th Ed., (Hardman, Limbird, eds.), McGraw-Hill, 1996, p. 54.
Gura, "Cancer models: Systems for identifying new drugs are often faulty," Science 278:1041-42 (1997).
Ho et al., "Clinical pharmacology of tetrahydrouridine," J. Clin. Pharmacol. 18:259-65 (1978).
International Preliminary Report on Patentability Corresponding to International Application No. PCT/US2010/030081; Date of Mailing: Oct. 20, 2011; 11 pages.
International Search Report Corresponding to International Application No. PCT/US2008/080163; Date of Mailing: Feb. 11, 2009; 6 pages.
International Search Report Corresponding to International Application No. PCT/US2010/030073; Date of Mailing; May 20, 2010; 5 pages.
International Search Report Corresponding to International Application No. PCT/US2010/030078; Date of Mailing: Sep. 7, 2010; 5 pages.
Kantarjian et al., "Decitabine improves patient outcomes in myelodysplastic syndromes," Cancer 106:1794-1803 (2006).

Kararli, "Comparison of the Gastrointestinal Anatomy, Physiology, and Biochemistry of Humans and Commonly Used Laboratory Animals," Biopharm. Drug Disposition 16:351-80 (1995).
Kees et al., "Development of resistance to 1-β-D-Arabinofuranosylcytosine after High-Dose Treatment in Childhood Lymphoblastic Leukemia: Analysis of resistance Mechanism in Established Cell Lines," Cancer Res. 49:3015-19 (1989).
Kelley et al., "Furanose-pyranose isomerization of reduced pyrimidine and cyclic urea ribosides," J. Med. Chem. 29:2351-58 (1986).
Kim et al., "Synthesis of Pyrimidin-2-one Nucleosides as Acid-Stable inhibitors of Cytidine Deaminase." J. Med. Chem. 29:1374-80 (1986).
Kondo et al., "Characteristics of the Gastric pH Profiles of Unfed and Fed Cynomolgus Monkeys as Pharmaceutical Product Development Subjects," Biopharm. Drug Disposition. 24:45-51 (2003).
Kreis et al., "Combinations of Tetrahydrouridine and Cytosine Arabinoside in Mouse Tumors," Cancer Treat. Rep. 61:1355-64 (1977).
Kreis et al., "Effect of tetrahydrouridine on the clinical pharmacology of 1-β-D-arabinofuranosylcytosine when both drugs are coinfused over three hours," Cancer Res, 48:1337-42 (1988).
Kreis et al., "Tetrahydrouridine: physiologic disposition and effect upon deamination of cytosine arabinoside in man," Cancer Treatment Rep. 61:1347-53 (1977).
Kreis et al., "Therapy of refractory/relapsed acute leukemia with cytosine arabinoside plus tetrahydrouridine (an inhibitor of cytidine deaminase)—a pilot study," Leukemia 5:991-98 (1991).
Lemaire et al., "Enhancement of antineoplastic action of 5-aza-2'-deoxycytidine by zebularine on L1210 leukemia," Anticancer Drugs 16:301-08 (2005).
Marquez et al., "1,3-Diazepinones. 1. Synthesis of 5-Hydroxyperhydro-1,3-diazepin-2-one." J. Organic Chem. 45:485-89 (1980).
Marsh et al., Therapy of refractory/relapsed acute myeloid leukemia and blast crisis of chronic myeloid leukemia with the combination of cytosine arabinoside, tetrahydrouridine, and carboplatin, Cancer Chemther. Pharmacol. 31:481-84 (1993).
Momparler et al., "Induction of cytidine deaminase in HL-60 myeloid leukemic cells by 5-aza-2'-deoxycytidine," Leukemia Res. 14:751-54 (1990).
Neil et al., Enhancement by tetrahydrouridine (NSC-112907) of the oral activity of 5-azacytidine (NSC-102816) in L1210 leukemic mice, Cancer Chemother. Rep. Part 1 59:459-65 (1975).
Neil et al., "Enhancement by tetrahydrouridine of 1-β-D-arabinofuranosylcytosine (cytarabine) oral activity in L1210 leukemic mice," Cancer Res. 30:2166-72 (1970).
Norton et al., "Synthesis of Deoxytetrahydrouridine," J. Organic Chem. 74:2221-23 (2009).
Office Action Corresponding to U.S. Appl. No. 12/252,961; Mailed Jun. 8, 2011.
Office Action Corresponding to U.S. Appl. No. 12/755,106; Mailed Sep. 29, 2011.
Office Action Corresponding to U.S. Appl. No. 12/755,122; Mailed Oct. 18, 2011.
Vincenzetti et al., "Recombinant Human Cytidine Deaminase: Expression, Purification, and Characterization," Protein Expression Purification 8:247-53 (1996).
Watanabe et al., Nucleosides. 110. Synthesis and antiherpes virus activity of some 2'-fluoro-2'-deoxyarabinofuranoslpyrimidine nucleosides, J. Med. Chem. 22:21-24 (1979).
Wentworth et al., "Cytidine deaminases (from *Escherichia coli* and human liver)," Meth. Enzymol. 51:401-7 (1978).
Wisdom et al., "Cytidine Aminohydrolase from Sheep Liver," Proc. Biochem. Soc., 471st Meeting , CIBA Laboratories, Ltd., Horsham, May 20, 1967, 7P.
Wong et al., "Phase I evaluation of tetrahydrouridine combined with cytosine arabinoside," Cancer Treatment Rep. 63:1245-49 (1979).
Atallah et al., "Use of hypomethylating agents in myelodysplastic syndromes," Clin. Adv. Hematol. Oncol. 5(7):544-52 (2007).
Bellmunt et al., "Phase I-II study of paclitaxel, cisplatin, and gemcitabine in advanced transitional-cell carcinoma of the urothelium," J. Clin. Oncol. 18(18):3247-55 (2000).

Bendell et al., "Phase I dose-escalation study of tezacitabine in combination with 5-fluorouracil in patients with advanced solid tumors," Cancer 103(9):1925-31 (2005).

Blum et al., "Phase I study of decitabine alone or in combination with valproic acid in acute myeloid leukemia," J. Clin. Oncol. 25(25):3884-91 (2007).

Cantor et al., "Epigenetic modulation of endogenous tumor suppressor expression in lung cancer xenografts suppresses tumorigenicity," Int. J. Cancer 120:24-31 (2006).

Choy, "Combination chemoradiotherapy with gemcitabine: Potential applications," Oncology, 14(74) (Suppl 4):20-25 (2000).

Dueñas-Gonzalez et al., "A phase II study of gemcitabine and cisplatin combination as induction chemotherapy for untreated locally advanced cervical carcinoma," Ann. Oncol. 12:541-47 (2001).

Fang et al., "A phase I and pharmacodynamic study of decitabine in combination with carboplatin in patients with recurrent, platinum-resistant, epithelial ovarian cancer," Cancer 116:4043-53 (2010).

Fenaux, "Inhibitors of DNA methylation: beyond myelodysplastic syndromes," Nature Clin. Pract. Oncol. 2:S36-S44 (2005).

Flaherty et al., "Dose escalation study of tezacitabine in combination with cisplatin in patients with advanced cancer," Cancer 97(8):1985-90 (2003).

Foss, "Nucleoside analogs and antimetabolite therapies for myelodysplastic syndrome," Best Pract. Res. Clin. Haematol. 17(4):573-84 (2004).

Gallardo et al., "A phase II study of gemcitabine in gallbladder carcinoma," Ann. Oncol. 12:1403-06 (2001).

Gore, "Intravenous azacitidine for MDS," Clin. Adv. Hematol. Oncol. 5(3):234 (2007).

Iliopoulos et al., "Inhibition of breast cancer cell growth in vitro and in vivo: Effect of restoration of wwox expression," Clin. Cancer Res. 13(1):268-74 (2007).

Isanbor et al., "Fluorine in medicinal chemistry: A review of anticancer agents," J. Fluorine Chem. 127:303-19 (2006).

Kantarjian et al., "Results of decitabine (5-aza-2'deoxycytidine) therapy in 130 patients with chronic myelogenous leukemia," Cancer 98:522-28 (2003).

Lange et al., "Distinctive demography, biology, and outcome of acute myeloid leukemia and myelodysplastic syndrome in children With Down Syndrome: Children's cancer group studies 2861 and 2891," Blood 91:608-15 (1998).

Lübbert et al., "Efficacy of a 3-day, low-dose treatment with 5-azacytidine followed by donor lymphocyte infusions in older patients with acute myeloid leukemia or chronic myelomonocytic leukemia relapsed after allografting," Bone Marrow Transpl. 45:627-32 (2010).

Makhija et al., "Results from a phase II randomized, placebo-controlled, double-blind trial suggest improved PFS with the addition of pertuzumab to gemcitabine in patients with platinum-resistant ovarian, fallopian tube, or primary peritoneal cancer," J. Clin. Oncol. 25(18S):275 s Abstract 5507 (2007).

Missiaglia et al., "Growth delay of human pancreatic cancer cells by methylase inhibitor 5-aza-2'-deoxycytidine treatment is associated with activation of the interferon signalling pathway," Oncogene 24:199-211 (2005).

Momparler et al., "Epigenetic therapy of cancer with 5-aza-2'-deoxycytidine (decitabine)," Semin. Oncol. 32:443-51 (2005).

Penz et al., "Phase II trial of two-weekly gemcitabine in patients with advanced biliary tract cancer," Ann. Oncol. 12:183-86 (2001).

Rizzieri et al., "Phase I evaluation of prolonged-infusion gemcitabine with mitoxantrone for relapsed or refractory acute leukemia," J. Clin, Oncol. 20(3):674-79 (2002).

Rodriguez et al., "Phase I clinical trials of tezacitabine [(E)-2'-deoxy-2'—(fluoromethylene)cytidine] in patients with refractory solid tumors", Clin. Cancer Res. 8:2828-34 (2002).

Scaife et al., (2008) *Antimetabolites In Cancer Therapy*, In *Anticancer Therapeutics*, John Wiley & Sons, Ltd., pp. 91-110.

Shao et al., "Ribonucleotide reductase inhibitors and future drug design," Curr. Cancer Drug Targets 6:409-31 (2006).

Soriano et al., "Safety and clinical activity of the combination of 5-azacytidine, valproic acid, and all-*trans* retinoic acid in acute myeloid leukemia and myelodysplastic syndrome," Blood 110:2302-08 (2007).

Szafraniec et al., "New nucleoside analogs in the treatment of hematological disorders," Acta Poloniae Pharmaceutica—Drug Res. 61(3):223-32 (2004).

Thaler et al., "Comparative analysis of two consecutive phase II studies with IFN-α and IFN-α + ara-C in untreated chronic-phase CML patients," Bone Marrow Transpl. 17(Suppl 3):S25-S28 (1996).

Tsavaris et al., "Weekly gemcitabine for the treatment of biliary tract and gallbladder cancer," Invest. New Drugs 22:193-98 (2004).

Van Cutsem et al., "Phase III trial of gemcitabine plus tipifarnib compared with gemcitabine plus placebo in advanced pancreatic cancer," J. Clin. Oncol. 22(8):1430-38 (2004).

Yang et al., "Phase II study of gemcitabine in patients with advanced hepatocellular carcinoma", Cancer 89(4):750-56 (2000).

U.S. Appl. No. 12/755,106, filed Apr. 6, 2010; Office Action mailed Mar. 28, 2012.

U.S. Appl. No. 12/755,122, filed Apr. 6, 2010; Office Action mailed Mar. 30, 2012.

Pakistan Application No. 283/2010, filed Apr. 6, 2010, Office Action received May 21, 2012.

* cited by examiner

Figure 3 Effect of combination gemcitabine (1 mg/kg) PO plus ER-876437 (10 mg/kg) PO in the A2780 human ovarian cancer xenograft model Figure 5 HPLC Chromatograms of Gemcitabine in the Presence of CDA in Tris-HCl buffer at 37 °C at Selected Time Points Figure 6  HPLC Chromatograms of Gemcitabine in the Presence of CDA and ER-876437 in Tris-HCl buffer at 37 °C at Selected Time Points Figure 7  Effect of ER-876437 on the Levels of Gemcitabine in the Presence of CDA in Tris-HCl buffer at 37 °C

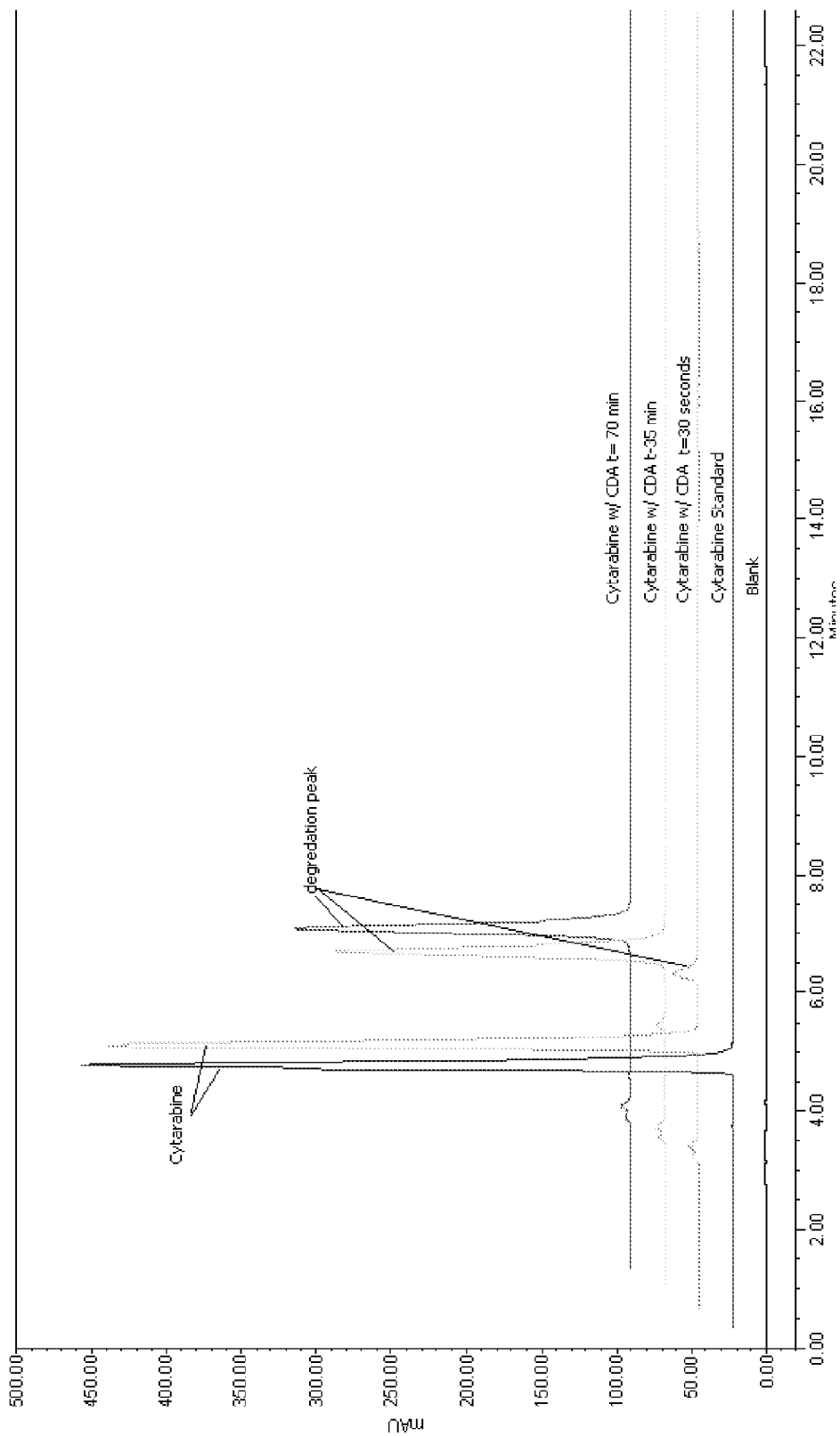
Figure 9 HPLC Chromatograms of Cytarabine in the Presence of CDA in Tris-HCl buffer at 37 °C at Selected Time Points

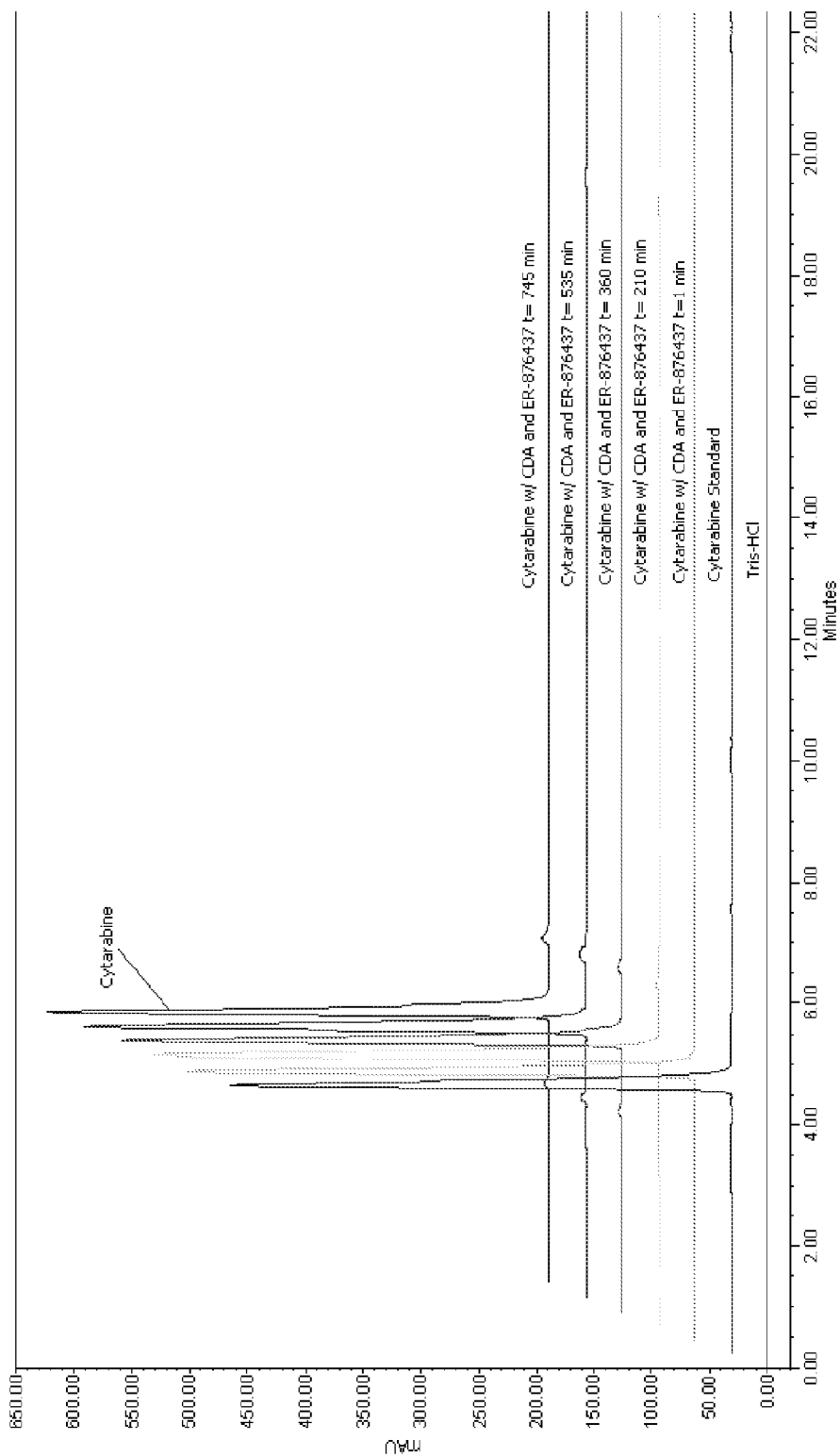
Figure 10 HPLC Chromatograms of Cytarabine in the Presence of CDA and ER-876437 in Tris-HCl buffer at 37 °C at Selected Time Points

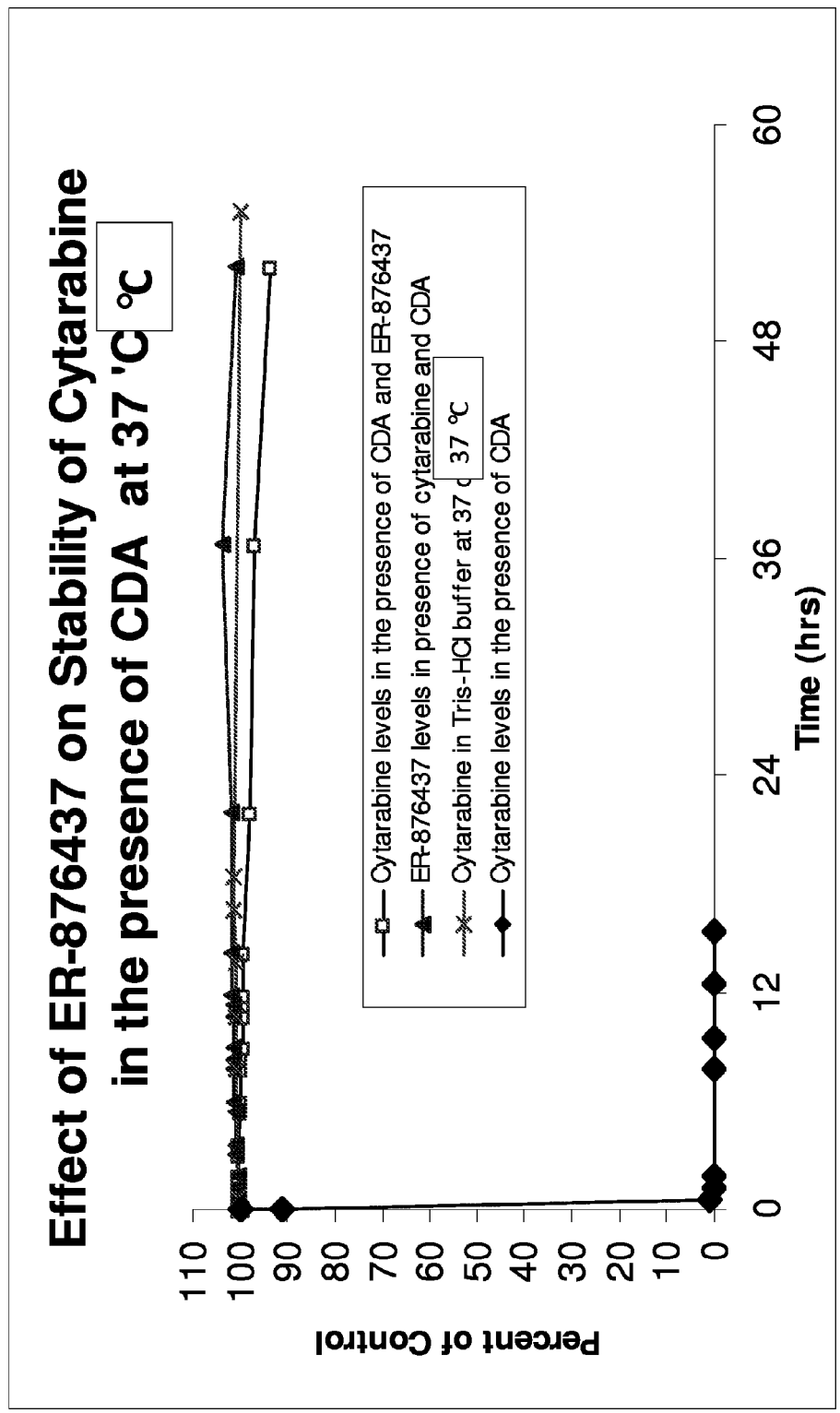
Figure 11   Effect of ER-876437 on the Levels of Cytarabine in the Presence of CDA in Tris-HCl buffer at 37 °C (Full Scale)

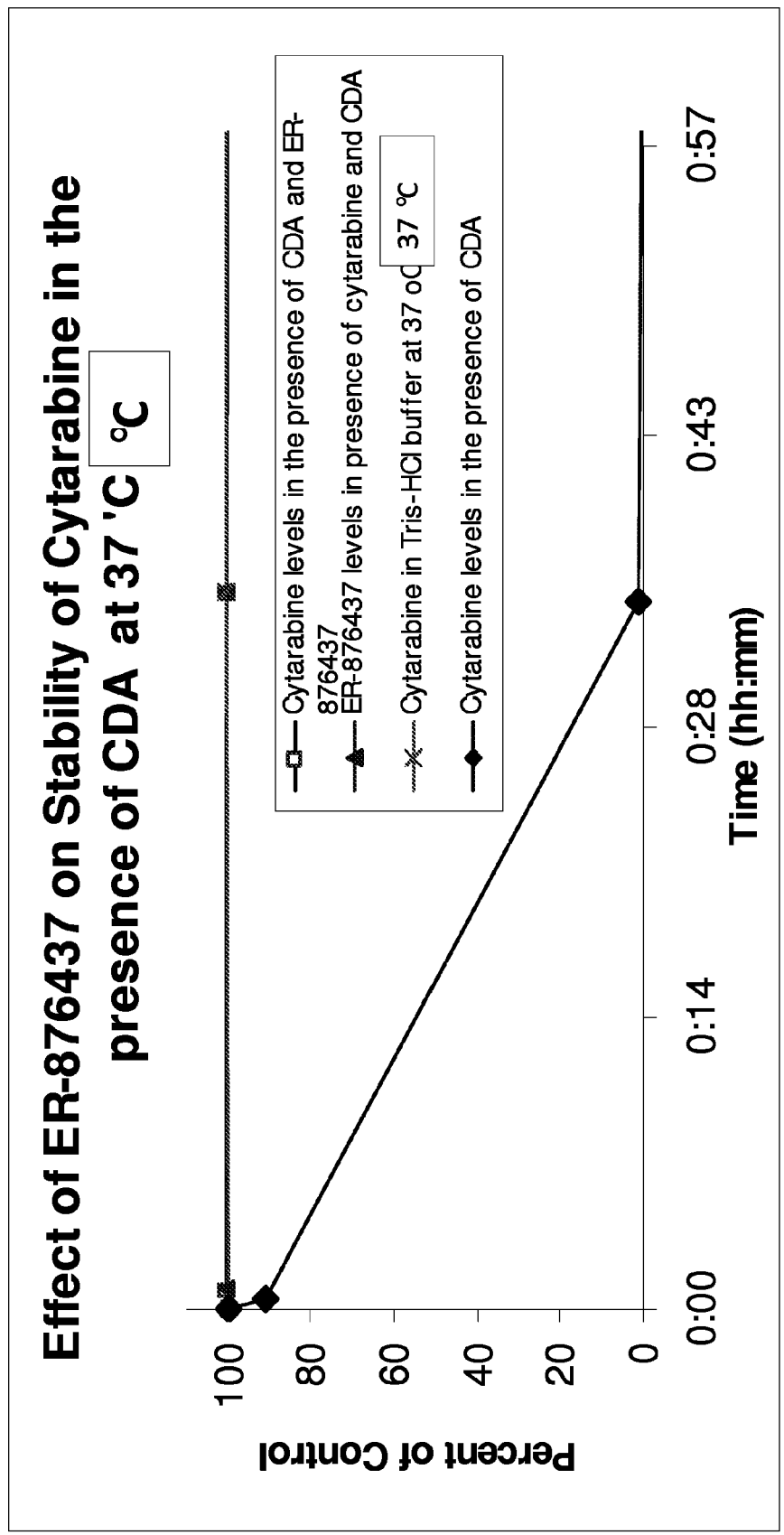
Figure 12  Effect of ER-876437 on the Levels of Cytarabine in the Presence of CDA in Tris-HCl buffer at 37 °C (Enlarged)

COMPOSITIONS AND METHODS FOR TREATING CANCER

RELATED APPLICATION

This application claims priority to U.S. Provisional Application No. 61/167,117, filed Apr. 6, 2009, entitled "COMPOSITIONS AND METHODS FOR TREATING CANCER." The contents of any patents, patent applications, and references cited throughout this specification are hereby incorporated by reference in their entireties.

BACKGROUND OF THE INVENTION

Cancer is the second most common cause of death in the U.S., exceeded only by heart disease, and accounts for 1 of every 4 deaths. Since 1990, in the U.S. alone, nearly five million lives have been lost to some form of cancer.

For example, breast cancer affects 186,000 women annually in the U.S., and the mortality rate of this disease has remained unchanged for 50 years. Surgical resection of the disease through radical mastectomy, modified radical mastectomy, or lumpectomy remains the mainstay of treatment for this condition. Unfortunately, a high percentage of those treated with lumpectomy alone will develop a recurrence of the disease.

Lung cancer is the most common cause of cancer death in both sexes in the United States. Lung cancer can result from a primary tumor originating in the lung or a secondary tumor which has spread from another organ such as the bowel or breast. Primary lung cancer is divided into three main types; small cell lung cancer; non-small cell lung cancer; and mesothelioma. There are three types of non-small cell lung cancer: squamous cell carcinoma, adenocarcinoma, and large cell carcinoma. Mesothelioma is a rare type of cancer that affects the covering of the lung called the pleura, and is often caused by exposure to asbestos.

Ovarian cancer accounts for about 3% of all cancers among women and ranks second among gynecologic cancers, following cancer of the uterine corpus. Ovarian cancer affects over 20,000 women in the United States each year and causes some 15,000 deaths annually. If the disease is diagnosed at the localized stage, the 5-year survival rate
is over 90%; however, only about 19% of all cases are detected at this stage.

The incidence of pancreatic cancer has been increasing steadily in the past twenty years in most industrialized countries, exhibiting the characteristics of a growing epidemiological problem.

Leukemia is a type of cancer that affects blood cells. Among the currently prescribed treatment regimes for leukemia are total body irradiation and chemotherapy. The two treatment regimes, however, pose a clinical dilemma: because leukemia is a cancer of the blood, all of the cells in the blood and all of the cells that arise in bone marrow must be treated in order to ensure destruction of the neoplastic cells. Destruction of all these cells leaves the patient in a severely immunodepressed state which could be as fatal as the leukemia.

Some cancer drugs are metabolized by an organism's naturally occurring enzymes such as adenosine deaminase (ADA, EC 3.5.4.4) and cytidine deaminase (CDA, also termed cytosine nucleoside deaminase, cytidine aminohydrolase, or EC 3.5.4.5). These enzymes function to deaminate natural aminopurine and aminopyrimidine nucleosides, respectively, in human and other organisms. These enzymes also convert active nucleoside-based cancer drugs into inactive metabolites. For example, the purine nucleoside drug arabinosyladenine (fludarabine, ara-A) is deaminated by ADA; the resulting compound, with the parent amino group replaced with hydroxyl, is inactive as an antitumor agent compared to the parent compound. Similarly, the antileukemia drug arabinosylcytosine (also termed cytarabine, Ara-C (or AraC); 4-Amino-1-(β-D-arabinofuranosyl)-2(1H)-pyrimidinone; Cytosine arabinoside; or 1-(β-D-Arabinofuranosyl)cytosine) is metabolically degraded by CDA into inactive arabinosyluracil.

CDA is a component of the pyrimidine salvage pathway. It converts cytidine and deoxycytidine to uridine and deoxyuridine, respectively, by hydrolytic deamination (*Arch. Biochem. Biophys.* 1991, 290, 285-292; *Methods Enzymol.* 1978, 51, 401-407; *Biochem. J.* 1967, 104, 7P). It also deaminates a number of synthetic cytosine analogs which are clinically useful drugs, such as ara-C mentioned above (*Cancer Chemother. Pharmacol.* 1998, 42, 373-378; *Cancer Res.* 1989, 49, 3015-3019; *Antiviral Chem. Chemother.* 1990, 1, 255-262). Conversion of the cytosine compounds to the uridine derivatives usually confers loss of therapeutic activity or addition of side-effects. It has also been shown that cancers that acquire resistance to cytosine analog drugs often overexpress CDA (*Leuk. Res.* 1990, 14, 751-754). Leukemic cells expressing a high level of CDA can manifest resistance to cytosine antimetabolites and thereby limit the antineoplastic activity of such therapeutics (*Biochem. Pharmacol.* 1993, 45, 1857-1861).

Tetrahydrouridine (THU, or 1(β-D-Ribofuranosyl)-4-hydroxytetrahydropyrimidin-2(1H)-one) has been known as an inhibitor of cytidine deaminase for a number of years.

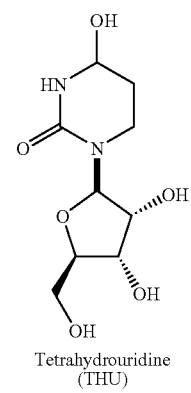

Tetrahydrouridine
(THU)

Various reports have suggested that co-administration with THU increases the efficacy and oral activity of cytidine-based drugs. For example, THU has been shown to enhance the oral activity of anti-leukemic agent 5-azacytidine (also termed AzaC; azacytidine; 5-azacitidine; azacitidine; 4-Amino-1-(β-D-ribofuranosyl)-1,3,5-triazin-2(1H)-one; or 1-(β-D-Ribofuranosyl)-5-azacytosine) in L1210 leukemic mice (*Cancer Chemotherapy Reports* 1975, 59, 459-465). The combination of THU plus 5-azacytidine has also been studied in a baboon sickle cell anemia model (*Am. J. Hematol.* 1985, 18, 283-288), and in human patients with sickle cell anemia in combination with orally administered 5-azacytidine (*Blood* 1985, 66, 527-532).

THU has also been shown to enhance the oral efficacy of ara-C in L1210 leukemic mice (*Cancer Research* 1970, 30, 2166; *Cancer Invest* 1987, 5, (4), 293-9), and in tumor-bearing mice (*Cancer Treat. Rep.* 1977, 61, 1355-1364). The combination of intravenously-administered ara-C with intravenously-administered THU has been investigated in several clinical studies in humans (*Cancer Treat. Rep.* 1977, 61, 1347-1353; *Cancer Treat. Rep.* 1979, 63, 1245-1249; *Cancer Res.* 1988, 48, 1337-1342). In particular, combination studies in patients with acute myeloid leukemia (AML) and chronic myeloid leukemia (CML) have been performed (*Leukemia* 1991, 5, 991-998; *Cancer Chemother. Pharmacol.* 1993, 31, 481-484).

Gemcitabine (also termed dFdC; 1-(4-Amino-2-oxo-1H-pyrimidin-1-yl)-2-deoxy-2,2-difluoro-β-D-ribofuranose: or 2'-deoxy-2',2'-difluorocytidine; or 2',2'-difluoro-2'-deoxycytidine), another cytidine-based antineoplastic drug, has also been studied in conjunction with CDA inhibitors (*Biochem. Pharmacol.* 1993, 45, 1857-1861). Co-administration with THU has been shown to alter the pharmacokinetics and bioavailability of gemcitabine in mice (*Abstr.* 1556, 2007 AACR Annual Meeting, Apr. 14-18, 2007, Los Angeles, Calif.; *Clin. Cancer Res.* 2008, 14, 3529-3535).

5-Fluoro-2'-deoxycytidine (fluorocytidine, FdCyd) is another cytidine-based anticancer drug which is an inhibitor of DNA methyltransferase. The modulation of its metabolism and pharmacokinetics by THU in mice has been studied (*Clin Cancer Res.*, 2006, 12, 7483-7491; *Cancer Chemother. Pharm.* 2008, 62, 363-368). FdCyd in combination with THU is currently the subject of an ongoing clinical trial identified by National Cancer Institute clinical trial no. NCT00378807.

The results of the aforementioned studies suggest that there is therapeutic utility in the administration of CDA inhibitors together with cytidine-based drugs such as gemcitabine, ara-C, 5-azacytidine and others. However, early CDA inhibitors such as THU suffer from drawbacks that include acid instability (*J. Med. Chem.* 1986, 29, 2351) and poor bioavailability (*J. Clin. Pharmacol.* 1978, 18, 259).

There is therefore an ongoing need for new, potent and therapeutically useful inhibitors of CDA, and new compositions that are useful for treating cancer or neoplastic disease.

SUMMARY OF THE INVENTION

There remains a need for new treatments and therapies for cancer and cancer-associated disorders. There is also a need for compounds useful in the treatment or amelioration of one or more symptoms of cancer. Furthermore, there is a need for methods for inhibiting the activity of the enzyme cytidine deaminase.

Thus, provided herein are compounds of formula I, II, III, IV, V, VI, VII, or VIII. Also provided herein are pharmaceutical compositions comprising (i) any one of the compounds of formula I, II, III, IV, V, VI, VII, or VIII and (ii) a pharmaceutically acceptable excipient or a pharmaceutically acceptable carrier.

In another aspect, provided herein is a method of inhibiting cytidine deaminase which comprises utilizing an effective amount of any compound of the formulae I-VIII. In one embodiment of this method, the compound is of the formula VIII.

In another aspect, provided herein is a pharmaceutical composition comprising a non-decitabine CDA substrate and any compound of the formulae I-VIII. In another aspect, provided herein is a pharmaceutical composition comprising a non-decitabine CDA substrate and a compound of formula I. In still another aspect, provided herein is a pharmaceutical composition comprising a non-decitabine CDA substrate and a compound of formula VIII. In certain embodiments of these pharmaceutical compositions, the non-decitabine CDA substrate may be cytidine, deoxycytidine, 5-azacytidine, gemcitabine, ara-C, tezacitabine, 5-fluoro-2'-deoxycytidine, cytochlor, 5,6-dihydro-5-azacytidine, 6-azacytidine, or 1-methyl-Ψ-isocytidine. In another embodiment, the non-decitabine CDA substrate may be 5-azacytidine, gemcitabine, ara-C, tezacitabine, 5-fluoro-2'-deoxycytidine, or cytochlor. In another embodiment, the non-decitabine CDA substrate may be gemcitabine.

In another aspect, provided herein is a method of treating cancer comprising: administering to a subject a pharmaceutical composition comprising a non-decitabine CDA substrate; and administering to a subject a pharmaceutical composition comprising a compound of formula I. In one embodiment of this method, the non-decitabine CDA substrate may be cytidine, deoxycytidine, 5-azacytidine, gemcitabine, ara-C, tezacitabine, 5-fluoro-2'-deoxycytidine, cytochlor, 5,6-dihydro-5-azacytidine, 6-azacytidine, or 1-methyl-Ψ-isocytidine. In another embodiment, the non-decitabine CDA substrate may be 5-azacytidine, gemcitabine, ara-C, tezacitabine, 5-fluoro-2'-deoxycytidine, or cytochlor. In another embodiment, the non-decitabine CDA substrate may be gemcitabine. In one embodiment of this method, the composition comprising a non-decitabine CDA substrate and the composition comprising a compound of formula I are simultaneously administered. In another embodiment, the composition comprising a non-decitabine CDA substrate and the composition comprising a compound of formula I are sequentially administered.

In another embodiment of this method, the cancer may be a hematological cancer or a solid cancer. Hematological cancers may be myelodysplastic syndromes or leukemias. Leukemias may be acute myeloid leukemia or chronic myeloid leukemia. Solid cancers may be pancreatic cancer, ovarian cancer, peritoneal cancer, non small cell lung cancer, or metastatic breast cancer.

In another aspect, provided herein is a method of treating cancer comprising:
administering to a subject a pharmaceutical composition comprising a non-decitabine CDA substrate; and administering to a subject a pharmaceutical composition comprising a compound of formula VIII. The non-decitabine CDA substrate may be cytidine, deoxycytidine, 5-azacytidine, gemcitabine, ara-C, tezacitabine, 5-fluoro-2'-deoxycytidine, cytochlor, 5,6-dihydro-5-azacytidine, 6-azacytidine, or 1-methyl-Ψ-isocytidine. In another embodiment, the non-decitabine CDA substrate may be 5-azacytidine, gemcitabine, ara-C, tezacitabine, 5-fluoro-2'-deoxycytidine, or cytochlor. In another embodiment, the non-decitabine CDA substrate may be gemcitabine. In one embodiment of this method, the composition comprising a non-decitabine CDA substrate and the composition comprising a compound of formula VIII are simultaneously administered. In another embodiment, the composition comprising a non-decitabine CDA substrate and the composition comprising a compound of formula VIII are sequentially administered.

In one embodiment of this method, the cancer may be a hematological cancer or a solid cancer. The hematological cancer may be myelodysplastic syndromes or leukemias. Leukemias may be acute myeloid leukemias or chronic myeloid leukemias. Solid cancers may be pancreatic cancer, ovarian cancer, peritoneal cancer, non small cell lung cancer, or metastatic breast cancer.

In another aspect, the invention provides herein use of the compound of formula I
for the manufacture of a medicament for treating cancer in a subject being treated with a non-decitabine CDA substrate. In still another aspect, the invention provides herein use of a compound of formula VIII for the manufacture of a medicament for treating cancer in a subject being treated with a non-decitabine CDA substrate. For either of these uses, the non-decitabine CDA substrate may be cytidine, deoxycytidine, 5-azacytidine, gemcitabine, ara-C, tezacitabine, 5-fluoro-2'-deoxycytidine, cytochlor, 5,6-dihydro-5-azacytidine, 6-azacytidine, or 1-methyl-Ψ-isocytidine. In another embodiment, the non-decitabine CDA substrate may be 5-azacytidine, gemcitabine, ara-C, tezacitabine, 5-fluoro-2'-deoxycytidine, or cytochlor. In another embodiment, the non-decitabine CDA substrate may be gemcitabine. In one embodiment of these uses, the cancer may be hematological cancers or solid cancers. In still another embodiment of these uses, hematological cancers may be myelodysplastic syndromes or leukemias. The leukemia may be acute myeloid leukemias or chronic myeloid leukemia. Solid cancers may be pancreatic cancer, ovarian cancer, peritoneal cancer, non small cell lung cancer, or metastatic breast cancer.

In another aspect, provided herein is a pharmaceutical composition comprising gemcitabine and a compound of formula I. In still another aspect, provided herein is a pharmaceutical composition comprising gemcitabine and a compound of formula VIII.

In still another aspect, provided herein is a method of treating cancer comprising: administering to a subject a pharmaceutical composition comprising gemcitabine; and administering to a subject a pharmaceutical composition comprising a compound of formula I. In one embodiment of this method, the composition comprising gemcitabine and the composition comprising a compound of formula I are simultaneously administered. In another embodiment of this method, the composition comprising gemcitabine and the composition comprising a compound of formula I are sequentially administered.

In another aspect, provided herein is a method of treating cancer comprising: administering to a subject a pharmaceutical composition comprising gemcitabine; and administering to a subject a pharmaceutical composition comprising a compound of formula VIII. In one embodiment of this method, the composition comprising gemcitabine and the composition comprising a compound of formula VIII are simultaneously administered. In another embodiment of this method, the composition comprising gemcitabine and the composition comprising a compound of formula VIII are sequentially administered.

In one embodiment of these methods, the cancer may be a hematological cancer or a solid cancer. The hematological cancer may be a myelodysplastic syndrome or a leukemia. The leukemia may be acute myeloid leukemia or chronic myeloid leukemia. The solid cancer may be pancreatic cancer, ovarian cancer, peritoneal cancer, non small cell lung cancer, or metastatic breast cancer.

In another aspect, provided herein is the use of a compound of formula I for the manufacture of a medicament for treating cancer in a subject being treated with a composition comprising gemcitabine. In another aspect, provided herein is the use of a compound of formula VIII for the manufacture of a medicament for treating cancer in a subject being treated with a composition comprising gemcitabine. In one embodiment of these uses, the cancer may be a hematological cancer or a solid cancer. A hematological cancer may be a myelodysplastic syndrome or a leukemia. The leukemia may be acute myeloid leukemia and chronic myeloid leukemia. The solid cancer may be pancreatic cancer, ovarian cancer, peritoneal cancer, non small cell lung cancer, or metastatic breast cancer.

In another aspect, provided herein is a method of inhibiting CDA from binding a non-decitabine CDA substrate, which comprises utilizing an effective amount of any compound of the formulae I-VIII. In one embodiment of this method, the non-decitabine CDA substrate may be cytidine, deoxycytidine, 5-azacytidine, gemcitabine, ara-C, tezacitabine, 5-fluoro-2'-deoxycytidine, cytochlor, 5,6-dihydro-5-azacytidine, 6-azacytidine, or 1-methyl-Ψ-isocytidine. In another embodiment of this method, the compound is of the formula VIII, and the non-decitabine CDA substrate is gemcitabine.

In one embodiment, the present invention is directed to combinations of (i) any of the compounds given by formulae I-VIII and (ii) a non-decitabine CDA substrate. In another embodiment, the present invention is directed to pharmaceutical compositions comprising combinations of (i) any of the compounds given by formulae I-VIII, (ii) a non-decitabine CDA substrate, and (iii) a pharmaceutically acceptable excipient. In yet another embodiment, the present invention is directed to methods of administering to a subject pharmaceutical compositions comprising combinations of (i) any of the compounds given by formulae I-VIII and (ii) a non-decitabine CDA substrate. In yet another embodiment, the present invention is directed to methods of treating cancer comprising administering to a subject pharmaceutical compositions comprising combinations of (i) any of the compounds given by formulae I-VIII and (ii) a non-decitabine CDA substrate.

In a preferred embodiment, the present invention is directed to combinations of (i) the compound given by formula VIII and (ii) a non-decitabine CDA substrate. In another preferred embodiment, the present invention is directed to pharmaceutical compositions comprising combinations of (i) the compound given by formula VIII, (ii) a non-decitabine CDA substrate, and (iii) a pharmaceutically acceptable excipient. In yet another preferred embodiment, the present invention is directed to methods of administering to a subject pharmaceutical compositions comprising combinations of (i) the compound given by formula VIII and (ii) a non-decitabine CDA substrate. In yet another preferred embodiment, the present invention is directed to methods of treating cancer comprising administering to a subject pharmaceutical compositions comprising combinations of (i) the compound given by formula VIII and (ii) a non-decitabine CDA substrate.

In another embodiment, the present invention is directed to combinations of (i) any of the compounds given by formulae I-VIII and (ii) a CDA substrate; with the proviso that the CDA substrate is neither (a) decitabine, nor (b) a decitabine prodrug. In another embodiment, the present invention is directed to pharmaceutical compositions comprising combinations of (i) any of the compounds given by formulae I-VIII, (ii) a CDA substrate, and (iii) a pharmaceutically acceptable excipient; with the proviso that the CDA substrate is neither (a) decitabine, nor (b) a decitabine prodrug. In yet another embodiment, the present invention is directed to methods of administering to a subject pharmaceutical compositions comprising combinations of (i) any of the compounds given by formulae I-VIII and (ii) a CDA substrate; with the proviso that the CDA substrate is neither (a) decitabine, nor (b) a decitabine prodrug. In yet another embodiment, the present invention is directed to methods of treating cancer comprising administering to a subject pharmaceutical compositions comprising combinations of (i) any of the compounds given by formulae I-VIII and (ii) a CDA substrate; with the proviso that the CDA substrate is neither (a) decitabine, nor (b) a decitabine prodrug.

In another preferred embodiment, the present invention is directed to combinations of (i) the compound given by formula VIII and (ii) a CDA substrate; with the proviso that the CDA substrate is neither (a) decitabine, nor (b) a decitabine prodrug. In another preferred embodiment, the present invention is directed to pharmaceutical compositions comprising combinations of (i) the compound given by formula VIII, (ii) a CDA substrate, and (iii) a pharmaceutically acceptable excipient; with the proviso that the CDA substrate is neither (a) decitabine, nor (b) a decitabine prodrug. In yet another preferred embodiment, the present invention is directed to methods of administering to a subject pharmaceutical compositions comprising combinations of (i) the compound given by formula VIII and (ii) a CDA substrate, with the proviso that the CDA substrate is neither (a) decitabine, nor (b) a decitabine prodrug. In yet another preferred embodiment, the present invention is directed to methods of treating cancer comprising administering to a subject pharmaceutical compositions comprising combinations of (i) the compound given by formula VIII and (ii) a CDA substrate; with the proviso that the CDA substrate is neither (a) decitabine, nor (b) a decitabine prodrug.

In another embodiment, the present invention is directed to combinations of (i) any of the compounds given by formulae I-VIII and (ii) a prodrug of a non-decitabine CDA substrate. In another embodiment, the present invention is directed to pharmaceutical compositions comprising combinations of (i) any of the compounds given by formulae I-VIII, (ii) a prodrug of a non-decitabine CDA substrate, and (iii) a pharmaceutically acceptable excipient. In yet another embodiment, the present invention is directed to methods of administering to a subject pharmaceutical compositions comprising combinations of (i) any of the compounds given by formulae I-VIII and (ii) a prodrug of a non-decitabine CDA substrate. In yet another embodiment, the present invention is directed to methods of treating cancer comprising administering to a subject pharmaceutical compositions comprising combinations of (i) any of the compounds given by formulae I-VIII and (ii) a prodrug of a non-decitabine CDA substrate.

In another preferred embodiment, the present invention is directed to combinations of (i) the compound given by formula VIII and (ii) a prodrug of a non-decitabine CDA substrate. In another preferred embodiment, the present invention is directed to pharmaceutical compositions comprising combinations of (i) the compound given by formula VIII, (ii) a prodrug of a non-decitabine CDA substrate, and (iii) a pharmaceutically acceptable excipient. In yet another preferred embodiment, the present invention is directed to methods of administering to a subject pharmaceutical compositions comprising combinations of (i) the compound given by formula VIII and (ii)) a prodrug of a non-decitabine CDA substrate. In yet another preferred embodiment, the present invention is directed to methods of treating cancer comprising administering to a subject pharmaceutical compositions comprising combinations of (i) the compound given by formula VIII and (ii) a prodrug of a non-decitabine CDA substrate.

In another embodiment, the present invention is directed to combinations of (i) any of the compounds given by formulae I-VIII and (ii) a prodrug of a CDA substrate; with the proviso that the prodrug of a CDA substrate is neither (a) decitabine, nor (b) a decitabine prodrug. In another embodiment, the present invention is directed to pharmaceutical compositions comprising combinations of (i) any of the compounds given by formulae I-VIII, (ii) a prodrug of a CDA substrate, and (iii) a pharmaceutically acceptable excipient; with the proviso that the prodrug of a CDA substrate is neither (a) decitabine, nor (b) a decitabine prodrug. In yet another embodiment, the present invention is directed to methods of administering to a subject pharmaceutical compositions comprising combinations of (i) any of the compounds given by formulae I-VIII and (ii) a prodrug of a CDA substrate; with the proviso that the prodrug of a CDA substrate is neither (a) decitabine, nor (b) a decitabine prodrug. In yet another embodiment, the present invention is directed to methods of treating cancer comprising administering to a subject pharmaceutical compositions comprising combinations of (i) any of the compounds given by formulae I-VIII and (ii) a prodrug of a CDA substrate; with the proviso that the prodrug of a CDA substrate is neither (a) decitabine, nor (b) a decitabine prodrug.

In another embodiment, the present invention is directed to combinations of (i) the compound given by formula VIII and (ii) a prodrug of a CDA substrate; with the proviso that the prodrug of a CDA substrate is neither (a) decitabine, nor (b) a decitabine prodrug. In another embodiment, the present invention is directed to pharmaceutical compositions comprising combinations of (i) the compound given by formula VIII, (ii) a prodrug of a CDA substrate, and (iii) a pharmaceutically acceptable excipient; with the proviso that the prodrug of a CDA substrate is neither (a) decitabine, nor (b) a decitabine prodrug. In yet another embodiment, the present invention is directed to methods of administering to a subject pharmaceutical compositions comprising combinations of (i) the compound given by formula VIII and (ii) a prodrug of a CDA substrate; with the proviso that the prodrug of a CDA substrate is neither (a) decitabine, nor (b) a decitabine prodrug. In yet another embodiment, the present invention is directed to methods of treating cancer comprising administering to a subject pharmaceutical compositions comprising combinations of (i) the compound given by formula VIII and (ii) a prodrug of a CDA substrate; with the proviso that the prodrug of a CDA substrate is neither (a) decitabine, nor (b) a decitabine prodrug.

BRIEF DESCRIPTION OF THE DRAWINGS

FIG. 9 shows HPLC chromatograms of cytaribine in the presence of CDA in Tris-HCl buffer at 37° C. at selected time points.

FIG. 10 shows HPLC chromatograms of cytaribine in the presence of CDA and ER-876437 in Tris-HCl buffer at 37° C. at selected time points.

FIG. 11 shows the effect of ER-876437 on the levels of cytarabine in the presence of CDA in Tris-HCl buffer at 37° C.

FIG. 12 shows the effect of ER-876437 on the levels of cytarabine in the presence of CDA in Tris-HCl buffer at 37° C.

DETAILED DESCRIPTION OF THE INVENTION

Figure 1:
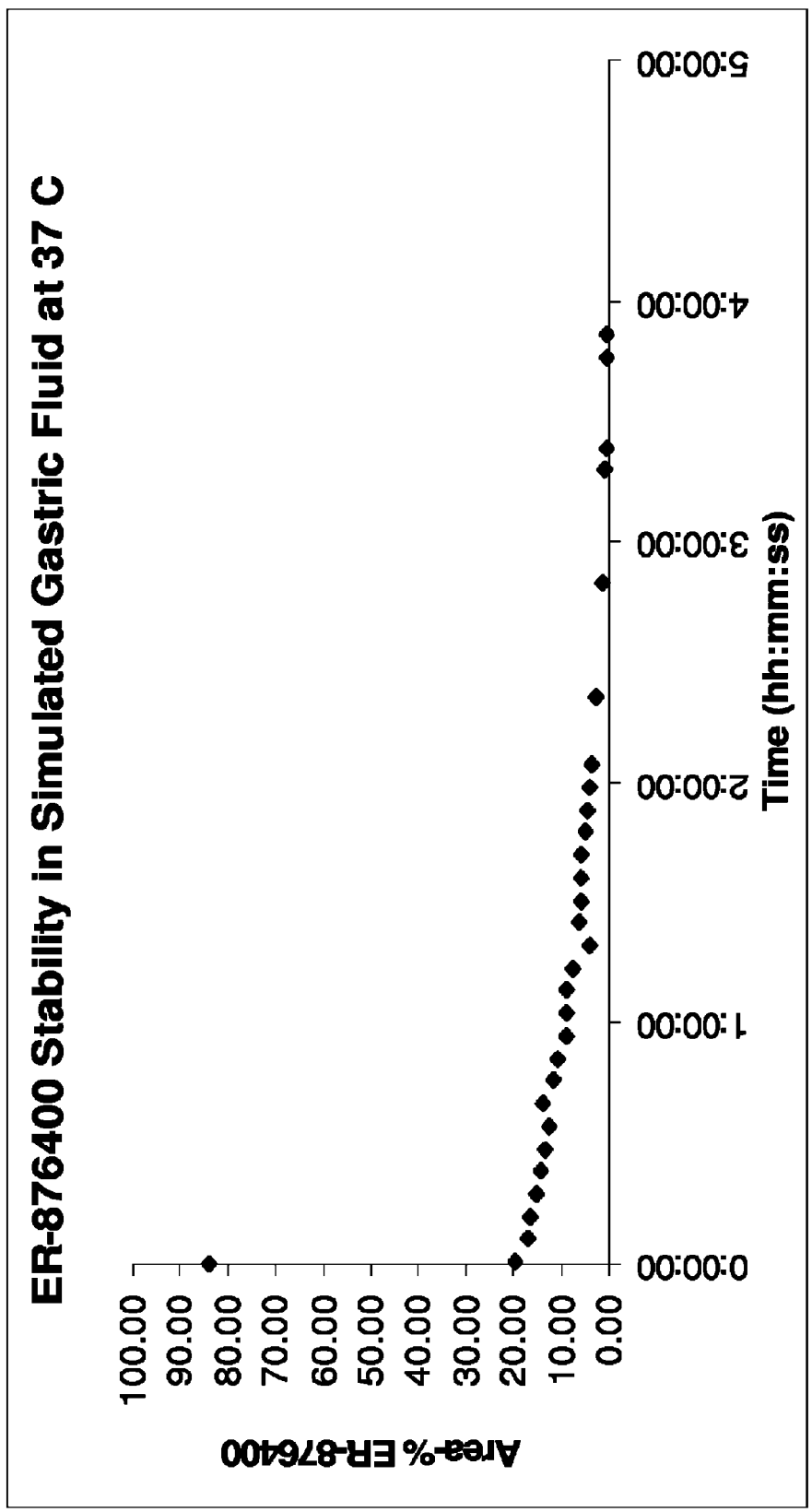
FIG. 1 shows a plot of total HPLC area-% purities of ER-876400 (1-((2R,3R,4S,5R)-3,4-dihydroxy-5-(hydroxymethyl)tetrahydrofuran-2-yl)-3,4-dihydro-1H-1,3-diazepin-2(7H)-one) as a function of time in simulated gastric fluid at 37° C.

Enzymes that deaminate natural aminopurine and aminopyrimidine nucleosides can also convert active anti-cancer drugs into inactive compounds in the human body. For example, the enzyme cytidine deaminase can rapidly convert the amino group of certain drugs to a hydroxyl group, rendering these compounds inactive. When an inhibitor of cytidine deaminase is co-administered with a drug that is otherwise deaminated (and consequently deactivated) by this enzyme, improved anti-tumor activity will be achieved.

The cytidine deaminase inhibitor (Z)-3,4-dihydro-1-((2R,3R,4S,5R)-tetrahydro-3,4-dihydroxy-5-(hydroxymethyl)furan-2-yl)-1H-1,3-diazepin-2(7H)-one (also referred to herein as "ER-876400"; 1-((2R,3R,4S,5R)-3,4-dihydroxy-5-(hydroxymethyl)tetrahydrofuran-2-yl)-3,4-dihydro-1H-1,3-diazepin-2(7H)-one; 2H-1,3-Diazepin-2-one, 1,3,4,7-tetrahydro-1-β-D-ribofuranosyl-; or given by chemical registry no. 75421-11-3) has been described in Liu, P. S. et al., *J. Med. Chem.* 24:662-666 (1981); and in U.S. Pat. No. 4,275,057 (both of which are incorporated herein by reference in their entireties). ER-876400 is given by formula IX:

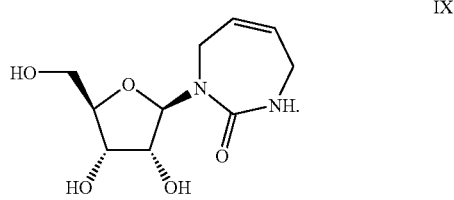

IX (Here and elsewhere, where discrepancies exist between a compound's name and a compound's structure, the chemical structure will control.)

Other cytidine deaminase inhibitors have previously been described in international application no. PCT/US2008/80163, filed on Oct. 16, 2008; in U.S. patent application Ser. No. 12/252,961, filed on Oct. 16, 2008; and in U.S. provisional patent application No. 60/980,397, filed Oct. 16, 2007; all of which are hereby incorporated by reference in their entireties.

Provided herein is a new class of inhibitors of cytidine deaminase ("CDA"). As described herein, these compounds have an improved half-life over other known compounds. In one embodiment, the compounds of the invention have an improved half-life in simulated gastric fluid compared to ER-876400. These compounds may be administered in combination with another anti-cancer medicament (e.g., a non-decitabine CDA substrate) for purposes of treating cancer (e.g., myelodysplastic syndrome, leukemia, pancreatic cancer, ovarian cancer, peritoneal cancer, non small cell lung cancer, or metastatic breast cancer).

DEFINITIONS

The following definitions are used throughout this specification:

As used in the specification and claims, the singular forms "a," "an," and "the" include plural references unless the content clearly dictates otherwise. Thus, for example, reference to a pharmaceutical composition comprising "a compound" may encompass two or more compounds.

"Alkyl" or "alkyl group" as used herein, means a straight-chain (i.e., unbranched), branched, or cyclic hydrocarbon chain that is completely saturated. Examples include without limitation methyl, ethyl, propyl, iso-propyl, butyl, iso-butyl, tert-butyl, n-pentyl and n-hexyl. In some embodiments, the alkyl chain is a $C_1$ to $C_6$ branched or unbranched carbon chain. In some embodiments, the alkyl chain is a $C_2$ to $C_5$ branched or unbranched carbon chain. In some embodiments, the alkyl chain is a $C_1$ to $C_4$ branched or unbranched carbon chain. In some embodiments, the alkyl chain is a $C_2$ to $C_4$ branched or unbranched carbon chain. In some embodiments, the alkyl chain is a $C_3$ to $C_5$ branched or unbranched carbon chain. In some embodiments, the alkyl chain is a $C_1$ to $C_2$ carbon chain. In some embodiments, the alkyl chain is a $C_2$ to $C_3$ branched or unbranched carbon chain. "In certain embodiments, the term "alkyl" or "alkyl group" includes a cycloalkyl group, also known as a carbocycle. Exemplary $C_{1-3}$ alkyl groups include methyl, ethyl, propyl, isopropyl, and cyclopropyl.

"Alkenyl" or "alkenyl group," as used herein, refers to a straight-chain (i.e., unbranched), branched, or cyclic hydrocarbon chain that has one or more double bonds. Examples include without limitation ethenyl, propenyl, iso-propenyl, butenyl, iso-butenyl, tert-butenyl, n-pentenyl and n-hexenyl. In some embodiments, the alkenyl chain is a $C_2$ to $C_6$ branched or unbranched carbon chain. In some embodiments, the alkenyl chain is a $C_2$ to $C_5$ branched or unbranched carbon chain. In some embodiments, the alkenyl chain is a $C_2$ to $C_4$ branched or unbranched carbon chain. In some embodiments, the alkenyl chain is a $C_3$ to $C_5$ branched or unbranched carbon chain. According to another aspect, the term alkenyl refers to a straight chain hydrocarbon having two double bonds, also referred to as "diene." In other embodiments, the term "alkenyl" or "alkenyl group" refers to a cycloalkenyl group.

"$C_{1-6}$ alkyl ester" refers to a $C_{1-6}$ alkyl ester where each $C_{1-6}$ alkyl group is as defined above. Accordingly, a $C_{1-6}$ alkyl ester group of an alcohol (—OH) has the formula —C(═O)O($C_{1-6}$ alkyl), wherein the terminal oxygen occupies the position of the alcoholic oxygen.

"$C_{2-6}$ alkenyl ester" refers to a $C_{2-6}$ alkenyl ester where each $C_{2-6}$ alkenyl group is as defined above. Accordingly, a $C_{2-6}$ alkenyl ester group of an alcohol (—OH) has the formula —C(═O)O($C_{2-6}$ alkenyl), wherein the terminal oxygen occupies the position of the alcoholic oxygen.

Unless indicated otherwise, where a bivalent group is described by its chemical formula, including two terminal bond moieties indicated by "—," it will be understood that the attachment is read from left to right.

Unless stereochemistry is depicted or otherwise stated or shown, structures depicted herein are also meant to include all enantiomeric, diastereomeric, and geometric (or conformational) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Any tautomeric forms of the compounds of the invention are within the scope of the invention.

Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention. Such compounds are useful, for example, as analytical tools or probes in biological assays.

"Treatment," "treat," and "treating" refer to reversing, alleviating, delaying the onset of, or inhibiting the progress of a disease or disorder as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms or in light of genetic or other susceptibility factors, or in light of a history of symptoms and in light of genetic or other susceptibility factors). Treatment may also be continued after symptoms have resolved, for example to mitigate or delay their recurrence. "Treating" in reference to a disease, disorder or condition also refers to: (i) slowing a disease, disorder or condition, e.g., arresting its development; or (ii) relieving a disease, disorder or condition, e.g., causing regression of the clinical symptoms, or (iii) slowing a disease, disorder or condition and relieving a disease, disorder or condition.

"Preventing" in reference to a disease, disorder or condition refers to preventing a disease, disorder or condition, e.g., causing the clinical symptoms of the disease, disorder or condition not to develop.

"Inhibit," "inhibitor," and "inhibition" in reference to any of the compounds given by formulae I-VIII (or the CDA inhibitors described herein including without limitation any of their salts, alkyl esters or alkenyl esters) refers to reducing the ability of CDA to bind a CDA substrate, thereby reducing the ability of CDA to enzymatically deaminate a CDA substrate. Without being bound by any theory, a compound's ability to inhibit CDA may be due to the compound's ability to bind the active site of a particular CDA protein thereby reducing the ability of that particular CDA protein from binding a CDA substrate. "Inhibit," "inhibitor," and "inhibition" in this context does not refer to a complete prevention of all CDA proteins from binding any CDA substrates. Rather, in this context, "inhibit," "inhibitor," and "inhibition" relate to the ability of CDA inhibitors to reduce the enzymatic deamination of CDA substrates by CDA. In one aspect, the methods of the present invention comprise contacting a cell with an effective amount of a CDA inhibitor compound, i.e., a compound of the invention, thereby inhibiting the activity of CDA.

"Patient" or "subject", as used herein, means an animal subject, preferably a mammalian subject (e.g., dog, cat, horse, cow, sheep, goat, monkey, etc.), and particularly human subjects (including both male and female subjects, and including neonatal, infant, juvenile, adolescent, adult and geriatric subjects). "Subject" can also refer to a cell or tissue, in vitro or in vivo, of an animal or a human.

As discussed further below, the term "CDA substrate" refers to any compound that may be deaminated by CDA. In one embodiment, the CDA substrate is neither (i) decitabine, nor (ii) a decitabine prodrug. The term "non-decitabine CDA substrate" as used herein refers to a CDA substrate that is neither (i) decitabine, nor (ii) a decitabine prodrug. The term "pro-drug of a non-decitabine CDA substrate" as used herein refers to a prodrug of a CDA substrate, wherein the CDA substrate is neither (i) decitabine, nor (ii) a decitabine prodrug. A "decitabine prodrug" is any compound that is transformed in vivo into decitabine. Nonlimiting examples of non-decitabine CDA substrates include cytidine, deoxycytidine, aza-C (5-azacytidine), gemcitabine, ara-C (1-β-D-arabinofuranosylcytosine), tezacitabine, 5-fluoro-2'-deoxycytidine, cytochlor, 5,6-dihydro-5-azacytidine, 6-azacytidine, and 1-methyl-Ψ-isocytidine. Cytidine and deoxycytidine are naturally occurring non-decitabine CDA substrates. In a particular embodiment, the non-decitabine CDA substrate is gemcitabine.

As discussed further below, a compound may be determined to be a CDA substrate through at least one of the following: (i) demonstration of relevant kinetics of deamination by CDA ($K_m$), and (ii) changes to its exposure in a subject when administered with any one of the compounds given by formulae I-VIII. A compound need not be positively evaluated by both of these evaluations to be determined to be a CDA substrate.

A compound may be determined to be a CDA substrate by evaluation of its kinetics of deamination by CDA ($K_m$) using known assays. See, for example, Bouffard, D. Y. et al., *Biochem. Pharm.* 45(9):1857-1861 (1993); Momparler, R. L. et al., *Biochem. Pharm.* 32(7):1327-1328 (1983); Cacciamani, T. et al., *Arch. Biochem. Biophys.* 290(2): 285-292 (1991); Wentworth, D. F. and Wolfenden, R., *Biochemistry* 14(23): 5099-5105 (1975); and Vincenzetti, S. et al., *Prot. Expression and Purification* 8:247-253 (1996), all of which are hereby incorporated by reference in their entireties. The $K_m$ value for cytidine was previously reported as 12±0.9 µM; the $K_m$ value for deoxycytidine was previously reported as 19±4 µM. Chabot et al., Biochem. Pharm. 32(7):1327-8 (1983). Additionally, $K_m$ values for ara-C (87±10 µM), gemcitabine (95.7±8.4 µM), and 5-azacytidine (216±51 µM) were also previously reported. Id. and Bouffard, D. Y. et al., *Biochem. Pharm.* 45(9):1857-1861 (1993). The $K_m$ value for cytidine for CDA from human liver has also been reported as 9.2 µM. Wentworth, D. F. and Wolfenden, R., *Biochemistry* 14(23): 5099-5105 (1975). This publication also identifies the $K_m$ value for 5-azacytidine (58 µM) and for 6-azacytidine (4200 µM). Id.

Hence, CDA substrates include those compounds having a $K_m$ value from at least greater than 10 µM and up to 4500 µM. The $K_m$ of the CDA substrate can fall within the range of 10 µM to 500 µM, from 10 µM to 400 µM, from 10 µM to 300 µM, from 10 µM to 200 µM, from 10 µM to 175 µM, from 10 µM to 150 µM, or from 200 µM to 300 µM. Alternatively, the $K_m$ value is at least greater than 50 µM and no greater than 500 µM. The $K_m$ of the CDA substrate can fall within the range of 50 µM to 500 µM, from 50 µM to 400 µM, from 50 µM to 300 µM, from 50 µM to 200 µM, from 50 µM to 175 µM, or from 50 µM to 150 µM.

A compound can also be determined to be a CDA substrate by evaluation of certain pharmacological parameters when administered to a subject simultaneously or sequentially with any one of the CDA inhibitors given by formulae I-VIII. For example, a compound's exposure in a subject may increase when it is administered simultaneously or sequentially with one of the CDA inhibitors given by formulae I-VIII. Such an evaluation would measure (i) the exposure of the compound when administered alone to a subject as compared to (ii) the exposure of the same compound when administered to a subject along with any one of the CDA inhibitors given by formulae I-VIII. When simultaneous or sequential administration of any one of the CDA inhibitors given by formulae I-VIII is found to increase the exposure of the compound, then the compound is a CDA substrate.

The exposure of a compound may be followed by taking a biological sample from the subject (e.g., blood or urine) and evaluating the biological sample using analytical techniques (e.g., high pressure or high performance liquid chromatography, or other analytical means). The analytical measurements may be used to determine the concentration-time profile of the compound and compute the compound's exposure using well known techniques. See, e.g., Gibaldi, M. and Perrier, D., *Pharmacokinetics*, 2d ed., Marcel Dekker, New York, 1982, which is hereby wholly incorporated by reference. Typically, the disappearance of the compound is followed as a function of time.

Exposure experiments may be conducted for purposes of determining whether a substance is a CDA substrate regardless of the form of the substance (e.g., salts, polymorphs, prodrugs). Thus, for example, a compound may be administered to a subject as a prodrug in, for example, an esterified or other metabolizable protected form. Upon administration to the subject, the prodrug may be, for example, de-esterified thereby releasing the active drug in vivo. Whether this active drug is a CDA substrate may be determined by conducting the above described analytical measurements with respect to the active drug. Alternatively, whether the prodrug itself is a CDA substrate may be determined by conducting the analytical measurements described in the preceeding two paragraphs with respect to the prodrug.

A non-decitabine CDA substrate may be a drug used for treating a cancer; or, a drug used for treating any other disease or ailment.

As used herein, a "prodrug" is a composition that undergoes an in vivo modification when administered to a subject, wherein the product of the in vivo modification is a therapeutically effective compound. Prodrugs of compounds may be prepared by, for example, preparing a given compound as an ester. The esterified form of the compound may be administered to a subject and may be de-esterified in vivo thereby releasing a therapeutically effective compound. Alternatively, some compounds may be prepared as prodrugs by adding short polypeptides (e.g., 1-6 amino acids) to the compound. Such prodrugs when administered to a subject may be cleaved (by, e.g., trypsin or other peptidases) thereby releasing a therapeutically effective compound. Formation of prodrugs is not limited by the specific examples described herein. Other ways of preparing therapeutically effective compounds as prodrugs are known. Examples of prodrugs of non-decitabine CDA substrates include, without limitation, Gemcitabine elaidate (also termed 9(E)-Octadecenoic acid 2'-deoxy-2',2'-difluorocytidin-5'-yl ester; 2'-Deoxy-2',2'-difluoro-5'-O-[9(E)-octadecenoyl]cytidine; CP-4126; or CAS Registry no. 210829-30-4); Azelaic acid gemcitabine ester meglumine salt (also termed 1-[5-O-(9-Carboxynonanoyl)-β-D-arabino-furanosyl]cytosine meglumine salt); other salts of Azelaic acid gemcitabine ester; and 1-[4-(2-Propylpentanamido)-2-oxo-1H-pyrimidin-1-yl]-2-deoxy-2,2-difluoro-β-D-ribo-furanose (also termed LY-2334737).

By the term "combination" is meant either a fixed combination in one dosage unit form, or a kit of parts for the combined administration where a compound of the present invention and a combination partner may be administered independently, at the same time, or separately within time intervals that especially allow that the combination partners show a cooperative, e.g., additive or synergistic, effect, or any combination thereof.

"Pharmaceutically acceptable" refers to those properties or substances that are acceptable to the patient from a pharmacological or toxicological point of view, or to the manufacturing pharmaceutical chemist from a physical or chemical point of view regarding composition, formulation, stability, patient acceptance, bioavailability and compatibility with other ingredients.

"Pharmaceutically acceptable excipient" can mean any substance, not itself a therapeutic agent, used as a carrier, diluent, binder, or vehicle for delivery of a therapeutic agent to a subject, or added to a pharmaceutical composition to improve its handling or storage properties or to permit or facilitate formation of a compound or composition into a unit dosage form for administration. Pharmaceutically acceptable excipients are well known in the pharmaceutical arts and are described, for example, in Remington's Pharmaceutical Sciences, Mack Publishing Co., Easton, Pa. (e.g., $20^{th}$ Ed., 2000), and Handbook of Pharmaceutical Excipients, American Pharmaceutical Association, Washington, D.C., (e.g., $1^{st}$, $2^{nd}$ and $3^{rd}$ Eds., 1986, 1994 and 2000, respectively). Excipients may provide a variety of functions and may be described as wetting agents, buffering agents, suspending agents, lubricating agents, emulsifiers, disintegrants, absorbents, preservatives, surfactants, colorants, flavorants, and sweeteners. Examples of pharmaceutically acceptable excipients include without limitation: (1) sugars, such as lactose, glucose and sucrose; (2) starches, such as corn starch and potato starch; (3) cellulose and its derivatives, such as sodium carboxymethyl cellulose, ethyl cellulose, cellulose acetate, hydroxypropylmethylcellulose, and hydroxypropylcellulose; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates or polyanhydrides; and (22) other non-toxic compatible substances employed in pharmaceutical formulations.

"Pharmaceutically acceptable carrier" as used herein refers to a nontoxic carrier or vehicle that does not destroy the pharmacological activity of the compound with which it is formulated. Pharmaceutically acceptable carriers or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, cyclodextrins, sodium carboxymethylcellulose, polyacrylates, waxes, polyethylene-polyoxypropylene-block polymers, polyethylene glycol and wool fat.

"Pharmaceutically acceptable salt" refers to an acid or base salt of a compound of the invention, which salt possesses the desired pharmacological activity and is neither biologically nor otherwise undesirable. The salt may be formed with acids that include without limitation acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride hydrobromide, hydroiodide, 2-hydroxyethane-sulfonate, lactate, maleate, methanesulfonate, 2-naphthalenesulfonate, nicotinate, oxalate, thiocyanate, tosylate and undecanoate. Examples of a base salt include without limitation ammonium salts, alkali metal salts such as sodium and potassium salts, alkaline earth metal salts such as calcium and magnesium salts, salts with organic bases such as dicyclohexylamine salts, N-methyl-D- glucamine, and salts with amino acids such as arginine and lysine. In some embodiments, the basic nitrogen-containing groups may be quarternized with agents including lower alkyl halides such as methyl, ethyl, propyl and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; and aralkyl halides such as phenethyl bromides.

"Animal" refers to a living organism having sensation and the power of voluntary movement, and which requires for its existence oxygen and organic food.

"Mammal" refers to a warm-blooded vertebrate animal with hair or fur. Examples include without limitation members of the human, equine, porcine, bovine, murine, canine or feline species.

"Cancer" refers to an abnormal growth of cells which tend to proliferate in an uncontrolled way and, in some cases, to metastasize (spread). Specific cancers types include without limitation the cancers identified in Publication No. US 2006/0014949 and the following:

- cardiac: sarcoma (e.g., such as angiosarcoma, fibrosarcoma, rhabdomyosarcoma, liposarcoma and the like), rhabdomyoma and teratoma;
- lung: bronchogenic carcinoma (e.g., such as squamous cell, undifferentiated small cell, undifferentiated large cell, adenocarcinoma and the like), alveolar (e.g., such as bronchiolar) carcinoma, sarcoma, lymphoma, non-small cell lung cancer and mesothelioma;
- gastrointestinal: esophagus (e.g., such as squamous cell carcinoma, adenocarcinoma, leiomyosarcoma, lymphoma and the like), stomach (e.g., such as carcinoma, lymphoma, leiomyosarcoma and the like), pancreas (e.g., such as ductal adenocarcinoma, insulinoma, carcinoid tumors, vipoma and the like), small bowel (e.g., such as adenocarcinoma, lymphoma, carcinoid tumors, Karposi's sarcoma, and the like), large bowel (e.g., such as adenocarcinoma, and the like);
- genitourinary tract: kidney (e.g., such as adenocarcinoma, lymphoma, leukemia, and the like), bladder and urethra (e.g., such as squamous cell carcinoma, transitional cell carcinoma, adenocarcinoma and the like), prostate (e.g., such as adenocarcinoma, sarcoma), testis (e.g., such as seminoma, teratoma, embryonal carcinoma, teratocarcinoma, choriocarcinoma, sarcoma, interstitial cell carcinoma, and the like);
- liver: hepatoma (e.g., hepatocellular carcinoma and the like), cholangiocarcinoma, hepatoblastoma, and angiosarcoma;
- bone: osteogenic sarcoma (e.g., such as osteosarcoma and the like), fibrosarcoma, malignant fibrous histiocytoma, chondrosarcoma, Ewing's sarcoma, malignant lymphoma (e.g., such as reticulum cell sarcoma), multiple myeloma, malignant giant cell tumor chordoma (e.g., such as osteocartilaginous exostoses), chondroblastoma, and giant cell tumors;
- nervous system: skull, meninges (e.g., such as meningiosarcoma, gliomatosis and the like), brain (e.g., such as astrocytoma, medulloblastoma, glioma, ependymoma, germinoma [pinealoma], glioblastoma multiform, oligodendroglioma, retinoblastoma, congenital tumors and the like), spinal cord (e.g., such as sarcoma and the like);
- breast cancer;
- gynecological: uterus (e.g., such as endometrial carcinoma and the like), cervix (e.g., such as cervical carcinoma, and the like), ovaries (e.g., such as ovarian carcinoma [serous cystadenocarcinoma, mucinous cystadenocarcinoma, unclassified carcinoma], Sertoli-Leydig cell tumors, dysgerminoma, malignant teratoma, and the like), vulva (e.g., such as squamous cell carcinoma, intraepithelial carcinoma, adenocarcinoma, fibrosarcoma, melanoma and the like), vagina (e.g., such as clear cell carcinoma, [squamous cell carcinoma, botryoid sarcoma (embryonal rhabdomyosarcoma], fallopian tubes (carcinoma) and the like);
- hematologic: blood (e.g., such as myeloid leukemia [acute and chronic], acute lymphoblastic leukemia, chronic lymphocytic leukemia, chronic myelocytic leukemia, myeloproliferative diseases, multiple myeloma, myelodysplastic syndrome and the like), Hodgkin's disease, non-Hodgkin's lymphoma;
- skin: malignant melanoma, basal cell carcinoma, squamous cell carcinoma, Karposi's sarcoma, and the like; and adrenal glands: neuroblastoma.

As used herein, "therapeutically effective amount" refers to an amount sufficient to elicit the desired biological response. A therapeutically effective amount of gemcitabine, for example, is an amount sufficient to treat a disease or disorder as described herein. A therapeutically effective amount of a compound given by formulae I-VIII is an amount sufficient to increase the in vivo exposure of a non-decitabine CDA substrate.

Throughout the specification, where discrepancies exist between the named compound and the structure shown, the structure shall control. Where any named synonyms (e.g., abbreviations, IUPAC names, generic or other chemic names, or registry numbers) provided for any particular compound actually relate to different compounds, then the specification shall be construed to refer to these compounds in the alternative.

Compounds of the Invention

The present invention provides compounds that inhibit the activity of CDA. In another embodiment, these compounds may be administered in combination with another anti-cancer medicament (e.g., a non-decitabine CDA substrate, a prodrug of a non-decitabine CDA substrate, or a precursor of a non-decitabine CDA substrate) for purposes of treating cancer (e.g., myelodysplastic syndrome, acute myelogenous leukemia, chronic myelocytic leukemia, non-small cell lung cancer, pancreatic cancer, ovarian cancer and breast cancer).

The present invention is directed to compounds of formula I:

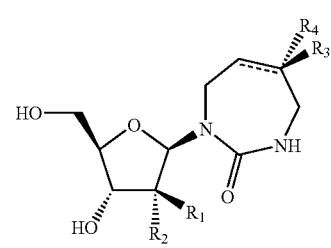

wherein:
one of $R_1$ and $R_2$ is F, and the other is selected from H and F;
one of $R_3$ and $R_4$ is H, and the other is selected from H and OH;
where ----- is a covalent bond or absent, and $R_4$ is absent and $R_3$ is flat when ----- is a covalent bond;
or a pharmaceutically acceptable salt, a $C_{1-6}$ alkyl ester, or a $C_{2-6}$ alkenyl ester thereof.

As used throughout the specification, the expression "$R_3$ is flat" means that $R_3$ resides in the same plane as the plane containing the carbon to which $R_3$ is attached as well as the two carbon atoms immediately adjacent to the carbon to which $R_3$ is attached.

In one embodiment of formula I, $R_1$ and $R_2$ are each F.

In another embodiment, formula I is represented by a compound of formula II:

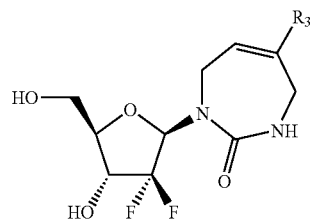

II or a pharmaceutically acceptable salt, a $C_{1-6}$ alkyl ester, or a $C_{2-6}$ alkenyl ester thereof.

In another aspect, the present invention is directed to ER-876437 (or, 2H-1,3-Diazepin-2-one, 1,3,4,7-tetrahydro-1-β-(D-2-deoxy-2,2-difluororibofuranosyl)-; or 1-((2R,4R,5R)-3,3-difluoro-4-hydroxy-5-(hydroxymethyl)tetrahydrofuran-2-yl)-3,4-dihydro-1H-1,3-diazepin-2(7H)-one, shown as formula VIII). Here and elsewhere, where discrepancies exist between a compound's chemical name and its structural depiction, the structural depiction will control. Where discrepancies exist between the structural depiction and $^1$H NMR data, the $^1$H NMR data will control.

In another aspect, the present invention is directed to compounds of formula VIII:

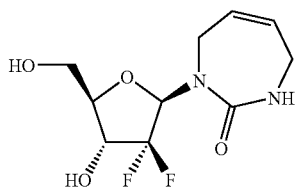

VIII or a pharmaceutically acceptable salt, a $C_{1-6}$ alkyl ester, or a $C_{2-6}$ alkenyl ester thereof.

In another aspect, the present invention is directed to compounds of formula VIII:

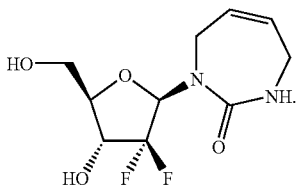

VIII in another embodiment, formula I is represented by a compound of formula III:

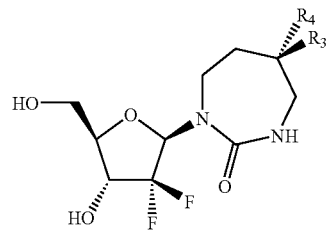

III wherein:
one of $R_3$ and $R_4$ is H, and the other is selected from H and OH;
or a pharmaceutically acceptable salt, a $C_{1-6}$ alkyl ester, or a $C_{2-6}$ alkenyl ester thereof.

In another embodiment, formula I is represented by a compound of formula IV:

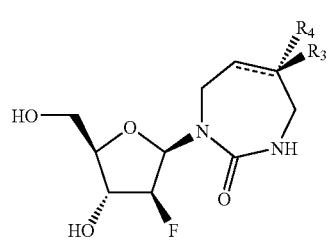

IV or a pharmaceutically acceptable salt, a $C_{1-6}$ alkyl ester, or a $C_{2-6}$ alkenyl ester thereof.

In one embodiment, formula IV is represented by a compound of formula V:

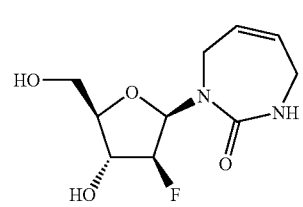

V or a pharmaceutically acceptable salt, a $C_{1-6}$ alkyl ester, or a $C_{2-6}$ alkenyl ester thereof.

In another embodiment, formula I is represented by a compound of formula VI:

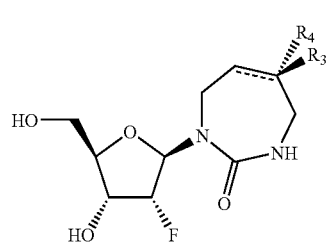

VI or a pharmaceutically acceptable salt, a $C_{1-6}$ alkyl ester, or a $C_{2-6}$ alkenyl ester thereof.

In one embodiment, formula VI is represented by a compound of formula VII:

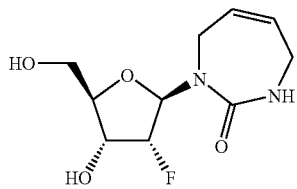

or a pharmaceutically acceptable salt, a $C_{1-6}$ alkyl ester, or a $C_{2-6}$ alkenyl ester thereof.

The present invention is also directed to pharmaceutical compositions comprising a compound of formula I:

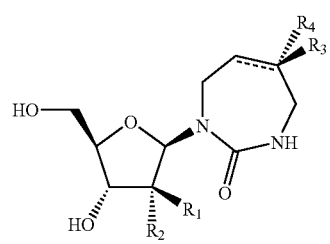

wherein:

one of $R_1$ and $R_2$ is F, and the other is selected from H and F;

one of $R_3$ and $R_4$ is H, and the other is selected from H and OH;

where ----- is a covalent bond or absent, and $R_4$ is absent and $R_3$ is flat when ----- is a covalent bond;

or a pharmaceutically acceptable salt, a $C_{1-6}$ alkyl ester, or a $C_{2-6}$ alkenyl ester thereof; and a pharmaceutically acceptable carrier.

In another embodiment, the present invention is also directed to pharmaceutical compositions comprising a compound of formula II:

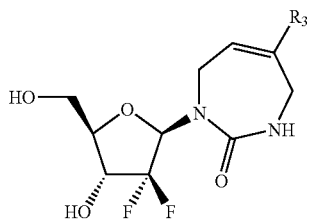

wherein R3 is selected from H and OH; or a pharmaceutically acceptable salt, a $C_{1-6}$ alkyl ester, or a $C_{2-6}$ alkenyl ester thereof; and a pharmaceutically acceptable carrier.

In another embodiment, the present invention is also directed to pharmaceutical compositions comprising a compound of formula III:

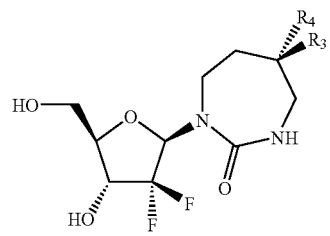

wherein:

one of $R_3$ and $R_4$ is H, and the other is selected from H and OH;

or a pharmaceutically acceptable salt, a $C_{1-6}$ alkyl ester, or a $C_{2-6}$ alkenyl ester thereof; and a pharmaceutically acceptable carrier.

In another embodiment, the present invention is also directed to a pharmaceutical composition comprising a non-decitabine CDA substrate and a compound of formula I:

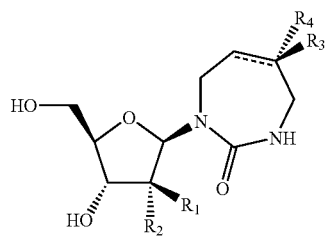

wherein:

one of $R_1$ and $R_2$ is F, and the other is selected from H and F;

one of $R_3$ and $R_4$ is H, and the other is selected from H and OH;

where ----- is a covalent bond or absent, and $R_4$ is absent when ----- is a covalent bond;

or a pharmaceutically acceptable salt, a $C_{1-6}$ alkyl ester, or a $C_{2-6}$ alkenyl ester thereof.

In one embodiment of the pharmaceutical composition comprising a non-decitabine CDA substrate and a compound of formula I, said non-decitabine CDA substrate is selected from the group consisting of 5-azacytidine, gemcitabine, ara-C, tezacitabine, 5-fluoro-2'-deoxycytidine, and cytochlor. In another embodiment, the pharmaceutical composition comprises a prodrug of a non-decitabine CDA substrate and a compound of formula I, said prodrug of a non-decitabine CDA substrate is selected from the group consisting of a prodrug of 5-azacytidine, gemcitabine, ara-C, tezacitabine, 5-fluoro-2'-deoxycytidine, or cytochlor.

In another embodiment, the present invention is also directed to a pharmaceutical composition comprising a non-decitabine CDA substrate and a compound of formula VIII:

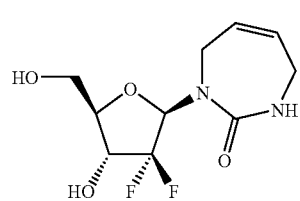

or a pharmaceutically acceptable salt, a $C_{1-6}$ alkyl ester, or a $C_{2-6}$ alkenyl ester thereof.

In another embodiment, the present invention is also directed to a pharmaceutical composition comprising a prodrug of a non-decitabine CDA substrate and a compound of formula VIII:

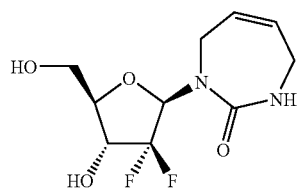

VIII or a pharmaceutically acceptable salt, a $C_{1-6}$ alkyl ester, or a $C_{2-6}$ alkenyl ester thereof.

In one embodiment of the pharmaceutical composition comprising a non-decitabine CDA substrate and a compound of formula VIII, said non-decitabine CDA substrate is selected from the group consisting of 5-azacytidine, gemcitabine, ara-C, tezacitabine, 5-fluoro-2'-deoxycytidine, and cytochlor. In another embodiment of the pharmaceutical composition comprising a prodrug of a non-decitabine CDA substrate and a compound of formula VIII, said prodrug of a non-decitabine CDA substrate is selected from the group consisting of a prodrug of 5-azacytidine, gemcitabine, ara-C, tezacitabine, 5-fluoro-2'-deoxycytidine, and cytochlor.

In another embodiment of the invention, a pharmaceutical composition can comprise (a) a compound of any one of formulae I-VIII and also (b) a non-decitabine CDA substrate. The non-decitabine CDA substrate may be 5-azacytidine, gemcitabine, ara-C, tezacitabine, 5-fluoro-2'-deoxycytidine, or cytochlor. In a particular embodiment, the pharmaceutical composition comprises (a) a compound of any one of formulae I-VIII and also (b) gemcitabine.

Another embodiment of the invention is directed to methods of administering the pharmaceutical compositions described herein. Hence, the present invention is directed to a method of treating a subject for cancer comprising administering to the subject a non-decitabine CDA substrate; and administering to the subject a pharmaceutical composition comprising a compound of any one of formulae I-VIII. The non-decitabine CDA substrate and the compound given may be any one of formulae I-VIII and may be administered to the subject sequentially or simultaneously. A sequential administration includes (a) first administering the non-decitabine CDA substrate followed by (b) administering the pharmaceutical composition comprising a compound of any one of formulae I-VIII. An alternative sequential administration includes (a) first administering the pharmaceutical composition comprising a compound of any one of formulae I-VIII followed by (b) administering the non-decitabine CDA substrate. A simultaneous administration includes administering the non-decitabine CDA substrate and the pharmaceutical composition comprising a compound of any one of formulae I-VIII at the same time; or at substantially the same time.

When administration involves the separate administration (e.g., sequential administration) of the first compound (e.g., a compound of Formula I) and a second compound (e.g., a non-decitabine CDA substrate), as described herein, the compounds are administered sufficiently close in time to have the desired therapeutic effect. For example, the period of time between each administration, which can result in the desired therapeutic effect, can range from minutes to hours to days and may be determined based on the properties of each compound such as potency, solubility, bioavailability, plasma half-life and kinetic profile. For example, the compounds may be administered in any order within 24-72 hours of each other or within any time less than 24 hours of each other. Alternatively, the compounds may be administered in any order within one week of each other.

When the non-decitabine CDA substrate and the compound of any one of formulae I-VIII are administered sequentially, they are separately formulated and may be provided in any order. When the non-decitabine CDA substrate and the compound of any one of formulae I-VIII are administered simultaneously, however, they may be either separately formulated or combined in the same formulation. When combined in the same formulation, the non-decitabine CDA substrate and the compound of any one of formulae I-VIII may be formulated so as to be released into the subject at the same time or at different times. The release profile of a formulation comprising both the non-decitabine CDA substrate and the compound of any one of formulae includes the following:

A) release and bioavailability of the non-decitabine CDA substrate followed by release and bioavailability of the compound of any one of formulae I-VIII;
B) release and bioavailability of the compound of any one of formulae I-VIII followed by release and bioavailability of the non-decitabine CDA substrate;
C) release and bioavailability of the compound of any one of formulae I-VIII at the same time as (or substantially at the same time as) release and bioavailability of the non-decitabine CDA substrate.

Thus, provided herein is a method of treating cancer, comprising administering to a subject in need thereof a composition comprising a non-decitabine CDA substrate and a compound of any one of formulae I-VIII.

When the non-decitabine CDA substrate is gemcitabine, the cancer to be treated may be colorectal cancer, pancreas tumor, breast tumor, brain tumor, prostate tumor, lung tumor, metastatic or recurrent nasopharyngeal carcinoma, metastatic solid tumors, prostate adenocarcinoma, urinary tract tumor, renal tumor, renal cell carcinoma, transitional cell carcinoma, urethral cancer, head and neck tumor, nonresectable head and neck cancer, squamous cell carcinoma of the head and neck, malignant pleural or peritoneal mesothelioma, cervical cancer, uterus tumor, testis tumor, germ cell tumor, granulosa cell tumor of the ovary, genital tract tumor, leukemia, adult T-cell lymphoma, B-cell lymphoma, Hodgkins disease, lymphoproliferative disease, mantle cell lymphoma, human myeloid and lymphoid leukemia, non-hodgkin lymphoma, hematological cancers, cutaneous T-cell lymphoma, acute myelogenous leukemia, acute lymphoblastic leukemia hemotological neoplasm, chronic lymphocytic leukemia, sarcoma, leiomyosarcoma, soft tissue sarcomas, Kaposi's sarcoma, osteosarcoma of the bone, hepatobiliary system tumor, liver carcinoma, cholangiocarcinoma, gallbladder tumor, pancreatic ductal adenocarcinoma, peritoneal tumor, intestine tumor, stomach tumor, endometrioid carcinoma, central nervous system tumor, small cell lung cancer, medulloblastoma, neuroblastoma or glioma.

In a particular embodiment, when the non-decitabine CDA substrate is gemcitabine, the cancer to be treated is pancreatic cancer, ovarian cancer, metastatic breast cancer, non-small cell lung cancer, bladder cancer, transitional cell carcinoma, biliary tract cancer, urothelial cancer, gallbladder carcinoma, fallopian tube cancer, primary peritoneal cancer, squamous cell carcinoma of the head and neck, hepatocellular carcinoma, liver tumor, lung carcinoma, uterine cervix tumor or colon cancer.

In still another embodiment, when the non-decitabine non-decitabine CDA substrate is gemcitabine, the cancer to be treated is non-small cell lung cancer, pancreatic cancer, bladder cancer, breast cancer, or oesophageal cancer. Thus, provided herein is a method of treating non-small cell lung cancer, pancreatic cancer, bladder cancer, breast cancer, or oesophageal cancer in a subject in need thereof, comprising administering to the subject a pharmaceutical composition comprising a compound of Formula VIII and gemticabine.

In another embodiment, provided herein is a method of treating cancer in a subject in need thereof, comprising administering to the subject a composition comprising gemcitabine and ER-876437. In still another embodiment, provided herein is a method of treating cancer in a subject in need thereof, comprising administering to the subject a composition comprising gemcitabine and ER-876437, wherein the cancer is selected from the group consisting of non-small cell lung cancer, pancreatic cancer, ovarian cancer and breast cancer.

In another embodiment, provided herein is a method of treating psoriasis vulgaris, smallpox, liver cirrhosis, thromboembolism, meningitis, salivary gland disease, urethral disease, lymphoproliferative disease, or neutropenia in a subject in need thereof, comprising administering to the subject a composition comprising gemcitabine and ER-876437.

In another embodiment, the invention is directed to combinations of any one of the compounds given by formulae I-VIII with a prodrug of a non-decitabine CDA substrate. Such combinations may be formulated or administered in all manners as described herein for combinations comprising the non-decitabine CDA substrate.

In another embodiment of the invention, the non-decitabine CDA substrate and the compound of any one of formulae I-VIII may be administered sequentially (in any order) or simultaneously with other pharmaceutical agents typically administered to subjects being treated for cancer. Such other pharmaceutical agents include without limitation anti-emetics, agents that increase appetite, other cytotoxic or chemotherapeutic agents, and agents that relieve pain. The non-decitabine CDA substrate and the compound of any one of formulae I-VIII may be formulated together with or separately from such other pharmaceutical agents.

A combination with such other pharmaceutical agents can either result in synergistic increase in anti-cancer activity, or such an increase may be additive. Compositions described herein typically include lower dosages of each compound in a composition, thereby avoiding adverse interactions between compounds or harmful side effects, such as ones which have been reported for similar compounds. Furthermore, normal amounts of each compound when given in combination could provide for greater efficacy in subjects who are either unresponsive or minimally responsive to each compound when used alone.

A synergistic effect may be calculated, for example, using suitable methods such as the Sigmoid-Emax equation (Holford, N. H. G. and Scheiner, L. B., Clin. Pharmacokinet. 6: 429-453 (1981)), the equation of Loewe additivity (Loewe, S, and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984)). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

In certain embodiments, the invention provides a pharmaceutical composition of any of the compositions of the present invention. In a related embodiment, the invention provides a pharmaceutical composition of any of the compositions of the present invention and a pharmaceutically acceptable carrier or excipient of any of these compositions. In certain embodiments, the invention includes the compositions as novel chemical entities.

In one embodiment, the invention includes a packaged cancer treatment. The packaged treatment includes a composition of the invention packaged with instructions for using an effective amount of the composition of the invention for an intended use. In other embodiments, the present invention provides a use of any of the compositions of the invention for manufacture of a medicament to treat cancer infection in a subject.

Synthetic Procedure

Within the scope of this text, a readily removable group that is not a constituent of the particular desired end product of the compounds of the present invention is designated a "protecting group." The protection of functional groups by such protecting groups, the protecting groups themselves, and their cleavage reactions are described for example in standard reference works, such as e.g., Science of Synthesis: Houben-Weyl Methods of Molecular Transformation. Georg Thieme Verlag, Stuttgart, Germany. 2005. 41627 pp. (URL: http://www.science-of-synthesis.com (Electronic Version, 48 Volumes)); J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (*Methods of Organic Chemistry*), Houben Weyl, 4th edition, Volume 15/I, Georg Thieme Verlag, Stuttgart 1974, in H.-D. Jakubke and H. Jeschkeit, "Aminosäuren, Peptide, Proteine" (*Amino acids, Peptides, Proteins*), Verlag Chemie, Weinheim, Deerfield Beach, and Basel 1982, and in Jochen Lehmann, "Chemie der Kohlenhydrate: Monosaccharide and Derivate" (*Chemistry of Carbohydrates: Monosaccharides and Derivatives*), Georg Thieme Verlag, Stuttgart 1974. A characteristic of protecting groups is that they may be removed readily (i.e., without the occurrence of undesired secondary reactions) for example by solvolysis, reduction, photolysis or alternatively under physiological conditions (e.g., by enzymatic cleavage).

Acid addition salts of the compounds of the invention are most suitably formed from pharmaceutically acceptable acids, and include for example those formed with inorganic acids, e.g., hydrochloric, hydrobromic, sulphuric or phosphoric acids and organic acids, e.g., succinic, malaeic, acetic or fumaric acid. Other non-pharmaceutically acceptable salts, e.g., oxalates may be used for example in the isolation of the compounds of the invention, for laboratory use, or for subsequent conversion to a pharmaceutically acceptable acid addition salt. Also included within the scope of the invention are solvates and hydrates of the invention.

The conversion of a given compound salt to a desired compound salt is achieved by applying standard techniques, in which an aqueous solution of the given salt is treated with a solution of base e.g. sodium carbonate or potassium hydroxide, to liberate the free base which is then extracted into an appropriate solvent, such as ether. The free base is then separated from the aqueous portion, dried, and treated with the requisite acid to give the desired salt.

In vivo hydrolyzable esters or amides of certain compounds of the invention may be formed by treating those compounds having a free hydroxy or amino functionality with the acid chloride of the desired ester in the presence of a base in an inert solvent such as methylene chloride or chloroform. Suitable bases include triethylamine or pyridine. Conversely, compounds of the invention having a free carboxy group may be esterified using standard conditions which can include activation followed by treatment with the desired alcohol in the presence of a suitable base.

Mixtures of isomers obtainable according to the invention may be separated in a manner known per se into the individual isomers; diastereoisomers may be separated, for example, by partitioning between polyphasic solvent mixtures, recrystallisation or chromatographic separation, for example over silica gel or by, e.g., medium pressure liquid chromatography over a reversed phase column, and racemates may be separated, for example, by the formation of salts with optically pure salt-forming reagents and separation of the mixture of diastereoisomers so obtainable, for example by means of fractional crystallisation, or by chromatography over optically active column materials.

Intermediates and final products may be worked up or purified according to standard methods, e.g., using chromatographic methods, distribution methods, (re-) crystallization, and the like.

Methods of preparing gemcitabine are known in the art.

In another embodiment, the invention is directed to a method of coupling cyclic urea compounds such as imidazolidin-2-one, tetrahydropyrimidin-2(1H)-one, 1,3-diazepan-2-one or 1,3,4,7-tetrahydro-2H-1,3-diazepin-2-one (ER-878899) to a C-2-substituted tetrahydrofuran ring comprising forming a reaction mixture by mixing (i) a first solution comprising the 1,3,4,7-tetrahydro-2H-1,3-diazepin-2-one in a reaction solvent with (ii) a second solution comprising the C-2-substituted tetrahydrofuran ring in the reaction solvent under reflux conditions. In this embodiment, the reflux conditions can maintain the volume of the reaction mixture as the first solution is added to the second solution. Alternatively, the reflux conditions can prevent the volume of the reaction mixture from increasing by more than 50%, 40%, 30%, 20%, 10%, 5%, 4%, 3%, 2% or 1%. In this embodiment, the reaction solvent can be a polar, aprotic solvent having a boiling point greater than 150° C., such as dimethylacetamide (DMA) or dimethylsulfoxide (DMSO). According to this embodiment, the second solution is heated to greater than 150° C., and the first solution can be added via syringe to the second solution. According to this embodiment, the first solution can be added to the second solution over a time period extending less than 10 hours, less than 5 hours, less than 3 hours, less than 2 hours, less than 1 hour or less than 30 minutes. According to this embodiment, the second solution can be heated from 150° C. to 250° C., from 175° C. to 225° C., or from 200° C. to 220° C. According to this embodiment, the C-2-substituted tetrahydrofuran ring can have substituents in the C-3 position, which can include one halogen in the C-3 position, two halogens in the C-3 position, or two fluorines in the C-3 position. According to this embodiment, the tetrahydrofuran ring can be ER-878898. With the exception of mutually exclusive values, any of the alternative features described in this paragraph can be used together.

In another embodiment, the invention is directed to a method of isolating ER-879381 from a mixture comprising ER-878617 comprising (i) contacting the mixture with a chromatographic substance, and separating the mixture on the substance using toluene and acetonitrile as the mobile phase. According to this embodiment, the chromatographic substance can be silica gel. According to this embodiment, the mobile phase can be toulene:acetonitrile in a 7:1 ratio. Alternatively, according to this embodiment, the toulene:acetonitrile can have a ratio of greater than 7:1, or less than 7:1. With the exception of mutually exclusive values, any of the alternative features described in this paragraph can be used together.

Dosage Forms

In certain other embodiments, the compositions of the instant invention (e.g., a compound of formula I in combination with a non-decitabine CDA substrate, e.g., ER-876437 in combination with gemcitabine) may be administered to a subject in need thereof using the formulations and methods described in U.S. Pat. No. 6,001,994, U.S. Pat. No. 6,469,058, and U.S. Pat. No. 6,555,518, and all of which are incorporated herein by reference in their entireties.

In some embodiments, pharmaceutical compositions of the compounds (or combinations) of the invention may be in unitary dosage form suitable for administration orally, rectally or by parenteral injection. For example, in preparing compositions in oral dosage form, any of the usual pharmaceutical media may be employed, such as, for example, water, glycols, oils, alcohols and the like, as in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are employed. For parenteral compositions, carriers usually comprise sterile water, at least in large part, though other ingredients, for example, to aid solubility, may be included. Injectable solutions, for example, are prepared using a carrier which comprises saline solution, glucose solution or a mixture of saline and glucose solution. Injectable suspensions may also be prepared in which case appropriate liquid carriers, suspending agents and the like may be employed. In case of compositions suitable for percutaneous administration, carrier optionally comprises a penetration enhancing agent or a suitable wetting agent, which may be combined with suitable additives of any nature in minor proportions, which additives do not cause a significant deleterious effect to the skin. Additives may facilitate the administration to the skin or may be helpful for preparing desired compositions. These compositions may be administered in various ways, e.g., as a transdermal patch, as a spot-on, as an ointment.

It is especially advantageous to formulate the pharmaceutical compositions described herein in dosage unit form for ease of administration and uniformity of dosage. Dosage unit form, as used herein, refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

In general it is contemplated that a therapeutically effective amount of a first or a second compound would be from 0.0001 mg/kg to 0.001 mg/kg; 0.001 mg/kg to 10 mg/kg body weight or from 0.02 mg/kg to 5 mg/kg body weight. In some embodiments, a therapeutically effective amount of a first or a second compound is from 0.007 mg to 0.07 mg, 0.07 mg to 700 mg, or from 1.4 mg to 350 mg. A method of prophylactic or curative treatment may also include administering the composition in a regimen of between one to five intakes per day.

In some embodiments, a therapeutically effective amount of a first compound or a second compound includes, but is not limited to, the amount less than 0.01 mg/dose, or less than 0.5 mg/dose, or less than 1 mg/dose, or less than 2 mg/dose, or less than 5 mg/dose, or less than 10 mg/dose, or less than 20 mg/dose, or less than 25 mg/dose, or less than 50 mg/dose, or less than 100 mg/dose, or less than 500 mg/dose. The number of times a day a first or a second compound is administrated to a subject may be determined based on various criteria commonly used in the art or those described herein.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, α-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical, buccal, sublingual, rectal, vaginal or parenteral administration. The formulations may conveniently be presented in unit dosage form and may be prepared by any methods well known in the art of pharmacy. The amount of active ingredient that may be combined with a carrier material to produce a single dosage form will generally be that amount of the composition that produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a composition of the present invention with the carrier and, optionally, one or more accessory ingredients. In general, the formulations are prepared by uniformly and intimately bringing into association a composition of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) or as mouth washes and the like, each containing a predetermined amount of a composition of the present invention as an active ingredient. A composition of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, or any of the following: fillers or extenders, such as starches, lactose, sucrose, glucose, mannitol, or silicic acid; binders, such as, for example, carboxymethylcellulose, alginates, gelatin, polyvinyl pyrrolidone, sucrose or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered composition moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes or microspheres. They may be sterilized by, for example, filtration through a bacteria-retaining filter, or by incorporating sterilizing agents in the form of sterile solid compositions that may be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that may be used include polymeric substances and waxes. The active ingredient can also be in micro-encapsulated form, if appropriate, with one or more of the above-described excipients.

Liquid dosage forms for oral administration of the compositions of the invention include pharmaceutically acceptable emulsions, microemulsions, solutions, suspensions, syrups and elixirs. In addition to the active ingredient, the liquid dosage forms may contain inert diluent commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compositions, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compositions of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active composition.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a composition of this invention include powders, sprays, ointments, pastes, creams, lotions, gels, solutions, patches and inhalants. The active composition may be mixed under sterile conditions with a pharmaceutically acceptable carrier, and with any preservatives, buffers, or propellants that may be required.

The ointments, pastes, creams and gels may contain, in addition to an active composition of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a composition of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a composition of the present invention to the body. Such dosage forms may be made by dissolving or dispersing the composition in the proper medium. Absorption enhancers can also be used to increase the flux of the composition across the skin. The rate of such flux may be controlled by either providing a rate controlling membrane or dispersing the active composition in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compositions of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity may be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compositions in biodegradable polymers such as polylactide-polyglycolide, Depending on the ratio of drug to polymer, and the nature of the particular polymer employed, the rate of drug release may be controlled. Examples of other biodegradable polymers include poly (orthoesters) and poly(anhydrides). Depot injectable formulations are also prepared by entrapping the drug in liposomes or microemulsions that are compatible with body tissue.

The preparations of the present invention may be given orally, parenterally, topically, or rectally. They are of course given by forms suitable for each administration route. For example, they are administered in tablets or capsule form, by injection, inhalation, eye lotion, ointment, suppository, etc., administration by injection, infusion or inhalation; topical by lotion or ointment; and rectal by suppositories. Oral or IV administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, or the pharmaceutical compositions of the present invention, are formulated into pharmaceutically acceptable dosage forms by conventional methods.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds or materials used in combination with the particular compound employed, the age, sex, weight, condition, general health and prior medical history of the patient being treated, and like factors well known in the medical arts.

A physician or veterinarian can determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound that is the lowest dose effective to produce a therapeutic effect. Such an effective dose will generally depend upon the factors described above. Generally, intravenous and subcutaneous doses of the compounds of this invention for a patient, when used for the indicated analgesic effects, will range from about 0.0001 to about 100 mg per kilogram of body weight per day, more preferably from about 0.01 to about 50 mg per kg per day, and still more preferably from about 1.0 to about 100 mg per kg per day. An effective amount is that amount treats a viral infection.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical composition.

EXAMPLES

General methods and experimentals for preparing compounds of the present invention are set forth below.

Example I

Chemical Syntheses

Unless otherwise stated, for Examples I.B.-I.C., solvent removal was carried out using a Büchi rotary evaporator. Analytical chromatography was carried out using a Hewlett Packard series 1100 HPLC and preparative chromatography was carried out using either Biotage SP4 instrument or a Waters 4000 instrument using Chiralpak IA columns under neutral condition, unless indicated otherwise. Mass spectra were recorded using Waters Acquity UPLC/MS system. Like or comparable equipment was used for the remaining examples.

NMR spectra were recorded using a Varian 400 MHz spectrometer (Examples I.B.-I.C.) or using a Fluka 400 MHz spectrometer (Examples I.A. and I.D.).

Example I.A.

ER-876437

I.A.1.: Preparation of ER-878899
(1,3,4,7-tetrahydro-2H-1,3-diazepin-2-one)

ER-878899 was prepared as outlined in Scheme I below. This preparation was described in *J. Med. Chem.* 1981, 24, 662-666; *J. Org. Chem.* 1980, 45, 485-489 and *Bull. Soc. Chim. Fr.* 1973, 198-292, all of which are hereby incorporated by reference in their entirety.

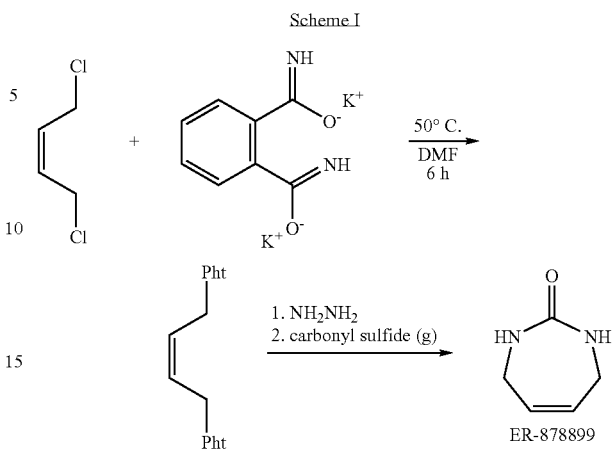

Mechanical stirring is required for the formation of ER-878899 made according to Scheme I. Carbonyl sulfide may be bubbled into the reaction flask using a glass pipette (of large diameter) and not a needle, which tends to clog due to the solid formed during the reaction. At the end of the reaction, the insoluble material in the reaction medium was filtered, and ER-878899 may be present in the filter cake.

I.A.2.: Preparation of ER-876437

ER-878899, prepared according to I.A.1., was used in Scheme II as described below.

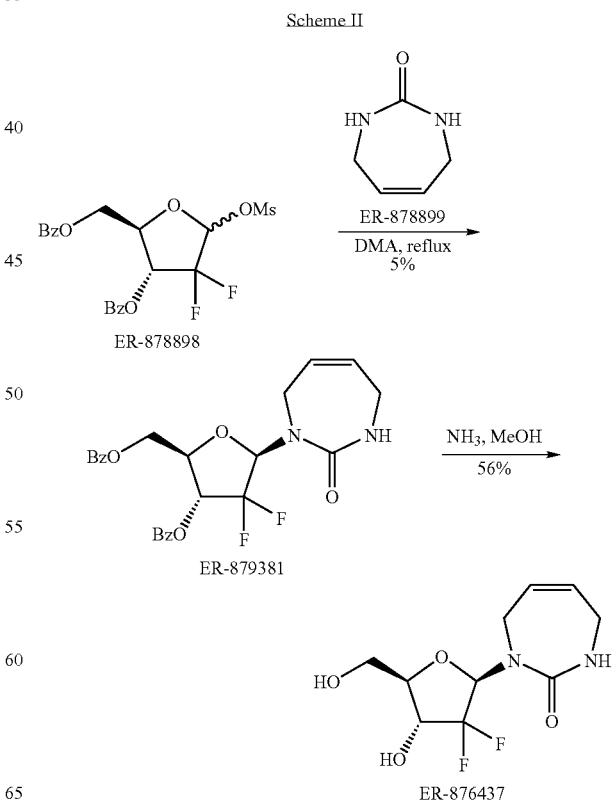

1-(3,3-Difluoro-4-benzoyl-5-benzoxymethyl-tetrahydro-furan-2-yl)-1,3,4,7-tetrahydro-[1,3]diazepin-2-one (ER-879381)

The commercially available mesylate ER-878898 shown above in Scheme II (3.8 g, 8.3 mmol) and the urea ER-878899 (900 mg, 8.0 mmol) were added to dimethylacetamide (DMA) (400 ml). Upon heating (170° C.), the reaction components solublized. The solution was heated overnight (15 h) under an atmosphere of nitrogen.

The DMA was then removed in vacuo. The residue was resuspended in EtOAc (150 ml) and then washed with water (2×75 ml). The combined organic layers were dried over MgSO$_4$, filtered, and concentrated in vacuo. The material was chromatographed on SiO$_2$ and was eluted with 50% EtOAc/hexanes. The material obtained after chromatography was the unresolved α/β anomers. The anomers were then separated using normal phase preparative HPLC (50% EtOAc/hexanes isocratic, 10 ml/min, Rt=25.7 min.); column: phenomenex luna 10μ Silica 100A, 250×21.20 mm; refractive index detector. The β anomer ER-879381 was isolated in >90% purity (10% α anomer, Rt. 24 min). $^1$H NMR (CDCl$_3$) δ 8.05 (m, 4H), 7.59 (m, 2H), 7.43 (m, 4H), 5.99 (m, 1H), 5.72 (m, 2H), 5.54 (m, 1H), 4.77 (dd, J=12.1, 3.4 Hz, 1H), 4.65 (br s, 1H), 4.56 (dd, J=12.4, 4.0 Hz, 1H), 4.38 (m, 1H), 3.80 (m, 4H).

1-(3,3-Difluoro-4-hydroxy-5-hydroxymethyl-tetrahydro-furan-2-yl)-1,3,4,7-tetrahydro-[1,3]diazepin-2-one (ER-876437)

ER-879381 was dissolved in NH$_3$ (7M) in MeOH (40 ml). The solution stirred overnight. The solvent was removed and the residue was purified by RP HPLC (10% acetonitrile/H$_2$O, flow 10 ml/min, R$_t$=23 minutes); column: phenomenex tuna 5μ C18(2) 100A, 250×21.2 mm; refractive index detector. The desired compound ER-876437 was obtained in 1.5% (62 mg) overall yield. $^1$H NMR (D$_2$O) δ 5.86 (m, 2H), 5.69 (dd, J=14.3 Hz, 6.2 Hz, 1H), 4.14 (m, 1H), 3.86 (m 1H), 3.74 (m, 6H). $^{13}$C NMR (D$_2$O) δ 164.5, 127.3, 126.2, 122.1 (dd, J=252, 261 Hz, 1C), 85.9 (dd, J=41, 22 Hz, 1C), 77.4 (d, J=8 Hz, 1C), 69.5 (dd, J=22 Hz, 19 Hz, 1C), 58.9, 41.0, 40.7.

The carbon, hydrogen and nitrogen components of the molecular formula (C$_{10}$H$_{14}$N$_2$O$_4$F$_2$+0.5H$_2$O) was calculated to be C, 43.96; H, 5.53; and N, 10.25. Elemental analysis revealed this material to contain C, 43.99; H, 5.36; and N, 10.21.

Marginal improvements to the yield of the coupling reaction of ER-878899 to the mesylate may be obtained by changing the reaction solvent. When diglyme is used as the solvent, a 15% yield improvement may be observed.

Example I.B.

ER-876437

I.B.1.: Preparation of ER-878899 (1,3,4,7-tetrahydro-2H-1,3-diazepin-2-one)

ER-878705 (shown below) was prepared following the procedure described in Feigenbaum. A. and Lehn, J. M., *Bull. Soc. Chim. Fr.*, 1973, 198-202 and Liu, P. S., Marquez, V. E., Driscoll, J. S. and Fuller, R. W., *J. Med. Chem.*, 1981, 24, 662-666.

Scheme III

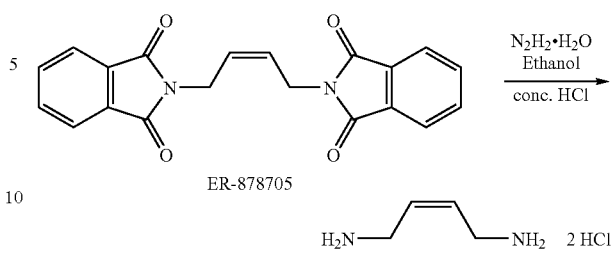

To a white suspension of ER-878705 (79.7 g, 230 mmol) in ethanol (470 mL) in a two-neck 2 L flask equipped with mechanical stirrer was added hydrazine hydrate (23.5 ml., 483 mmol) at room temperature. The resulting white suspension was heated to 50° C. for 30 minutes to obtain a clear light yellow solution. As white precipitate started appearing, the mixture was heated to 60° C. for 3 hours and the stirring became very difficult. After allowing the mixture to cool to room temperature, concentrated hydrogen chloride solution (40.3 mL, 483 mmol) was added and the mixture became easily stirred. After stirring for 30 minutes, the mixture was filtered and washed with 5×200 mL of water. The filtrate was concentrated to a dry solid. The dry solid was suspended in 200 mL of ethanol, and stirred for 1 hour to make a nice suspension. The suspension was filtered and washed with 3×100 mL pure ethanol. The cake (white granular-like crystal) was collected and dried to give 34.6 (94%) g of 1,4-diamino-2-butene di-hydrochloride salt. $^1$H NMR showed the product contains phthalhydazide as a minor impurity in the ratio of 5:1. $^1$H NMR (400 MHz, CD$_3$OD) δ 5.85 (ddd, J=1.6, 1.8 and 4.4 Hz, 2H), 3.69 (d, J=4.4, 4H).

Scheme IV

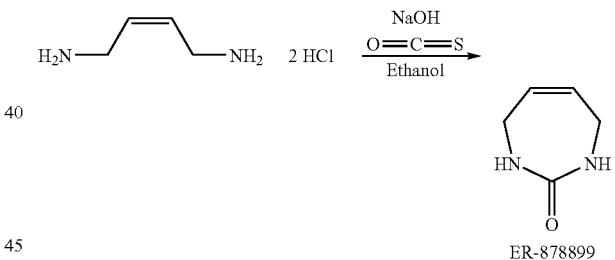

To a suspension of 1,4-diamino-2-butene di-hydrochloride salt (22.7 g, 143 mmol) in ethanol (1.2 L) in a two-neck 2 L flask was added 1.0 M NaOH solution (330 mL, 330 mmol). Upon addition of NaOH to the suspension, the mixture became a transparent and colorless solution. The solution was heated to 70° C. and carbonyl sulfide was bubbled through the heated mixture. Thereafter, the mixture was heated to 80° C. at reflux. After 3 hours, the bubbling was stopped and the mixture was heated an additional 1.5 hours, cooled to room temperature and neutralized by addition of 1.0 N HCl (50 mmol). The mixture was concentrated to a dry gray solid. The solid was suspended in 1 L of methanol, stirred for 2 hours, filtered and washed with methanol. The filtrate was concentrated to about 200 mL volume, cooled to 0° C., filtered and washed with cold methanol. The solid was collected and dried to give 5.05 g product. $^1$H NMR showed it contained very minor impurity phthalhydazide in the ratio of 13:1. $^1$H NMR (400 MHz, CD3OD) δ 5.91 (ddd, J=0.8, 1.2 and 1.6 Hz, 2H), 3.67 (d, J=4.0, 4H). The mother liquor was concentrated to about 30 mL, cooled to −10° C., filtered and washed with cooled MeOH (−10° C.). The solid was collected and dried to give 7.10 g of product with minor contamination of phthalhydrazide in the ratio of 4:1 as determined by $^1$H NMR.

I.B.2.: Preparation of ER-878617

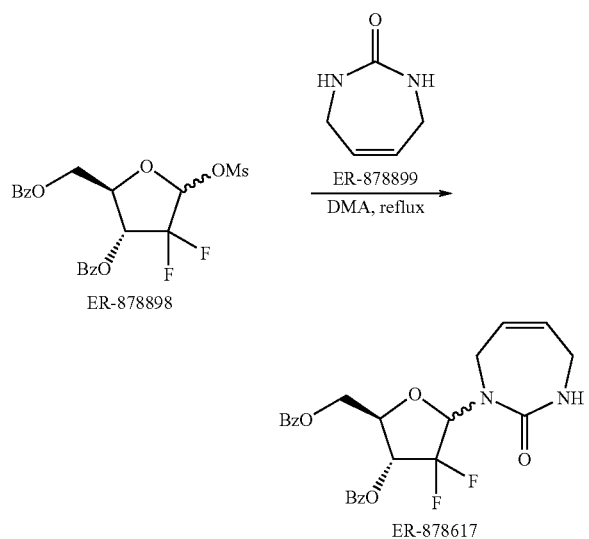

As depicted in Scheme V above, a solution of ER-878898 (1.33 g, 2.92 mmol, available from Waterstone or Depew Fine Chemical) and ER-878899 (200.0 mg, 1.78 mmol) in dry DMA (30 mL) was heated and stirred at 180-190° C. (oil bath temperature) as DMA distilled out slowly. Additional azeotroped 1,3,4,7-tetrahydro-2H-1,3-diazepin-2-one (800.0 mg, 7.13 mmol) in DMA (50 mL) was added with syringe pump over 2 hours during this DMA distillation. After addition of all material, the reaction was kept at reflux for 30 minutes and allowed to cool down. The reaction mixture was concentrated in vacuo and the residue was purified with chromatography to give ER-878617 (624.8 mg, 45%) as a mixture of two epimers.

I.B.3.: Preparation of ER-876437

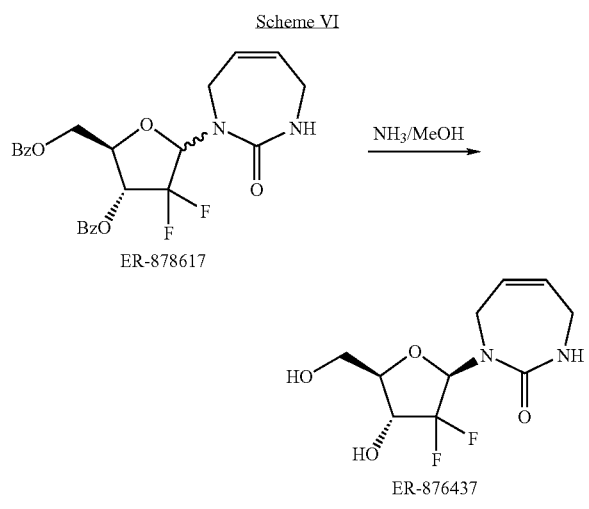

As depicted in Scheme VI above, a solution of ER-878617 (624.8 mg, 1.32 mmol) in 7 M ammonia/methanol (53 mL) was stirred at ambient temperature for 18 hours. The reaction mixture was concentrated in vacuo and the residue was purified with preparative TLC to give a crude product (274.2 mg, 78%) as the mixture of two epimers. The mixture of two epimers were separated on preparative chromatography with Chiralpak IA column (Daicel Chemical Industries, Ltd., Tokyo Japan) to give ER-876437 (160.2 mg).

Example I.C.

ER-876437

I.C.1.: Preparation of ER-879381

ER-879381 was made according to Scheme VII as shown below. ER-878899 was prepared as described above in Example I.B.1.

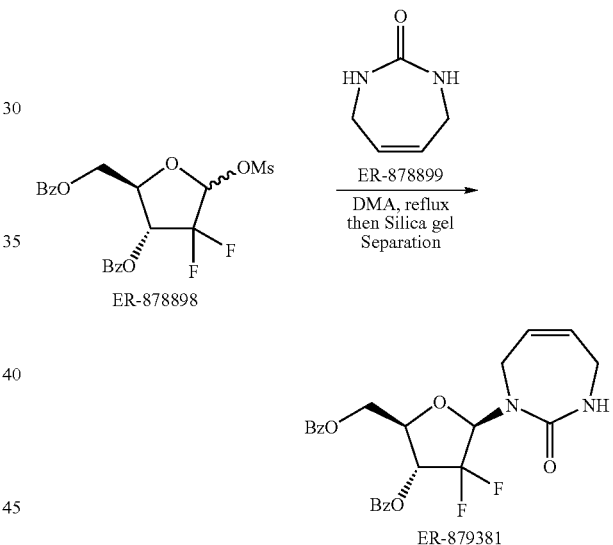

As depicted in Scheme VII above, a solution of ER-878898 (8.0 g, 18 mmol, available from Waterstone or Depew Fine Chemical) and ER-878899 (1.2 g, 10.7 mmol) in dry DMA (100 mL) was heated and stirred at 200-220° C. (oil bath temperature) as DMA distilled out slowly. Additional azeotroped 1,3,4,7-tetrahydro-2H-1,3-diazepin-2-one (4.8 g, 42.9 mmol) in DMA (350 mL) was added through syringe pump over 2 hours during this DMA distillation. After addition of all material, the reaction was kept at reflux for 30 minutes and allowed to cool down. The reaction mixture was concentrated in vacuo and the residue was combined with the residue from a separate experiment conducted on the same scale using the same procedure. The combined residue was purified with silica gel chromatography (mobile phase: 50-100% A AcOEt/Heptane) to give a mixture of two epimers (9.38 g). The mixture of two epimers was further separated with silica gel chromatography (mobile phase: toluene:acetonitrile=7:1) to produce ER-879381 (3.94 g).

I.C.2.: Preparation of ER-876437

ER-876437 was prepared as shown below in Scheme VIII.

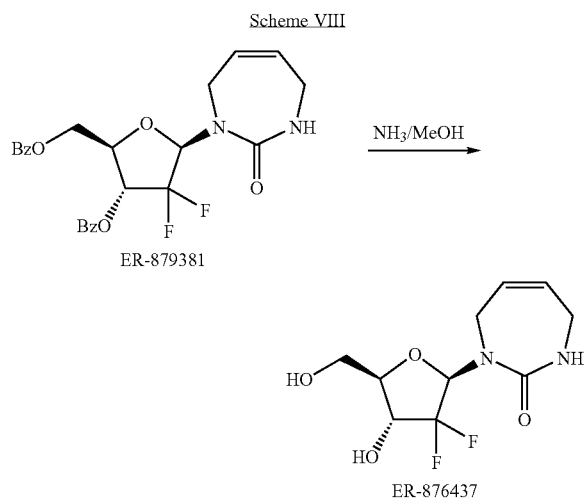

As depicted in Scheme VIII above, a solution of ER-879381 (3.8 g, 8.0 mmol) in 7 M ammonia/methanol (100 mL) was stirred at ambient temperature for 17 hours. The reaction mixture was concentrated in vacuo and the residue was purified with chromatography (mobile phase: 50-100% AcOEt/Heptane) to give ER-876437 (1.89 g, yield 89%).

Example I.D.

ER-878895

I.D.1.: Preparation of ER-878890

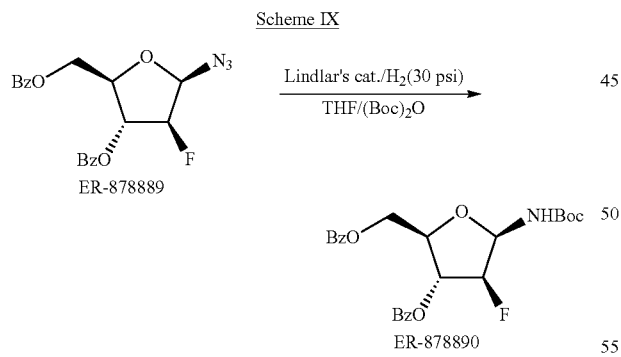

As depicted in Scheme IX above, a solution of ER-878889 (prepared according to Stimac, A. and Kobe, J., Carbohydr. Res., 2000, 329, 317-324, 4.3 g, 11.7 mmol) and di-tert-butyldicarbonate (5.4 g, 24.6 mmol) in THF (125 mL) was stirred in the presence of Lindlar's catalyst (1 g) at 30 psi over the weekend. The reaction suspension containing the hydrogenated product was filtered through Celite and concentrated. The residue was purified with radial chromatography to give ER-878890 (2.8 g). ER-878890 was further purified by recrystallization from AcOEt/Hexane to give white needles with mp 106-108° C.

I.D.2.: Preparation of ER-878891

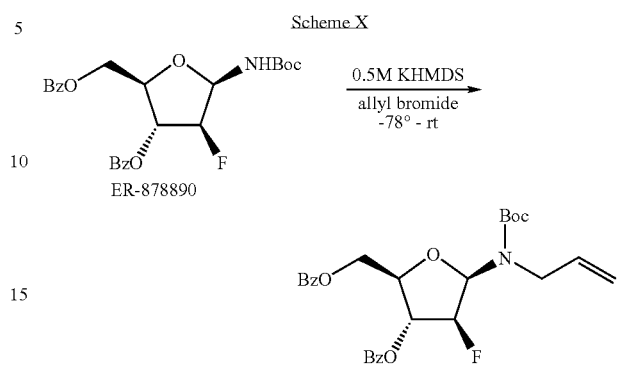

As depicted in Scheme X above, to a stirring solution of ER-878890 (1.6 g, 3.48 mmol) in THF/DMF (100 mL/30 mL) was added 0.5 M potassium hexamethydisilazide (KHMDS) in toluene (8.5 mL, 4.25 mmol) dropwise at about −78° C. (dry ice/acetone bath), followed by addition of allyl bromide (0.4 mL, 4.6 mmol). The reaction mixture was stirred overnight as the dry ice-acetone bath slowly warmed to room temperature (~25° C.). The reaction was quenched with saturated aqueous ammonium chloride and extracted with AcOEt. The organic phase was washed with brine and dried over anhydrous magnesium sulfate. The dried solution was filtered and evaporated. The residue was purified with radial chromatography to give ER-878891 (0.64 g).

I.D.3.: Preparation of ER-878892

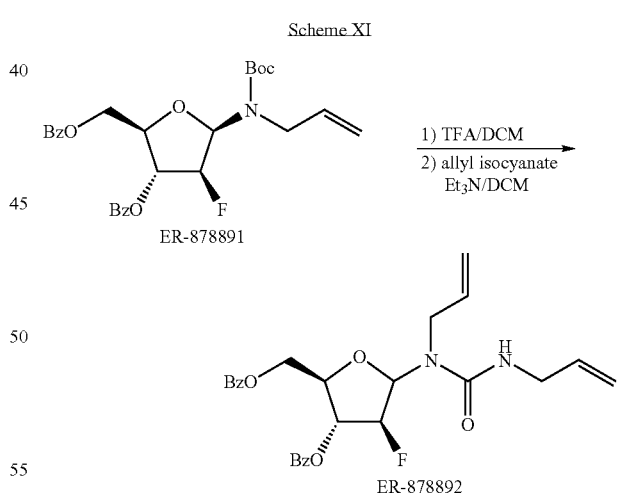

As depicted in Scheme XI above, to a stirring solution of ER-878891 (0.1 g, 0.2 mmol) in dichloromethane (DCM) (1 mL) under nitrogen was added trifluoroacetic acid (TFA) (0.5 mL) at room temperature. ER-878891 disappeared in 1 hour and the solvent and TFA were evaporated in vacuo. To the resulting oil redissolved in DCM (2 mL) was added allyl isocyanate (0.2 mL, 2.2 mmol) at room temperature. The reaction mixture was evaporated after 1 hour and purified by radial chromatography to give ER-878892 (50% yield) as a mixture of two anomers (beta/alpha ~3/1).

I.D.4.: Preparation of ER-878893

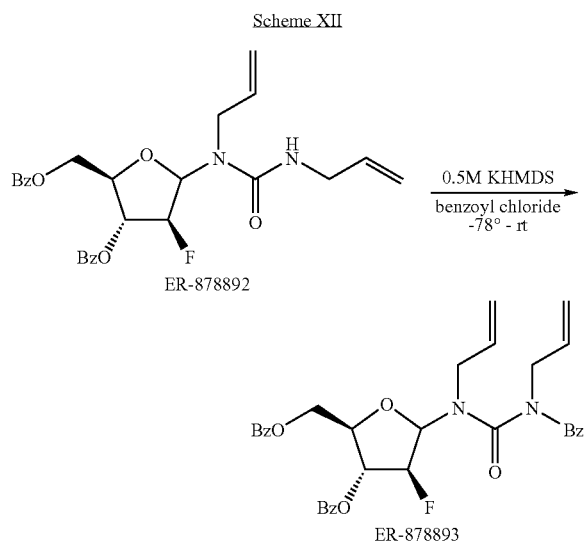

As depicted in Scheme XII above, to a stirring solution of ER-878892 (0.27 g, 0.56 mmol) in THF (10 mL) under nitrogen was added 0.5M KHMDS in toluene (1.5 mL, 0.75 mmol) at about −78° C. (dry ice/acetone bath), followed by addition of benzoyl chloride (0.6 mL, 5.1 mmol). The reaction mixture was stirred overnight and allowed to slowly warm to room temperature. The reaction was quenched with saturated aqueous ammonium chloride and extracted with AcOEt. The organic phase was washed with brine, dried over anhydrous magnesium sulfate, filtered and evaporated. The residue was purified with radial chromatography to give ER-878893 (0.13 g, 50% yield) as a mixture of anomers.

I.D.5.: Preparation of ER-878894

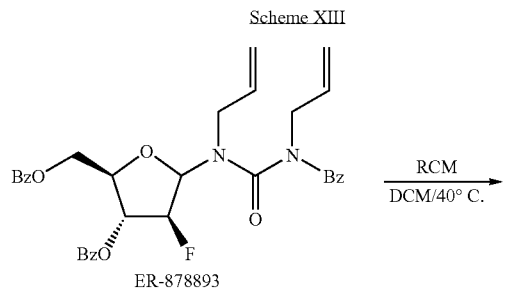

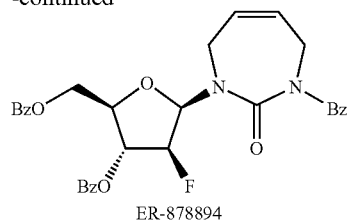

As depicted in Scheme XIII above, to a degassed solution of ER-878893 (0.13 g, 0.22 mmol) in DCM (120 mL) was added Grubb's $2^{nd}$ generation catalyst (~30 mg, available from Sigma-Aldrich, St. Louis, Mo.) under nitrogen. This catalyst affords the ring closing metathesis (RCM). The reaction mixture was heated at 40° C. for 1 hour followed by evaporation of the solvent. To the residue dissolved in AcOEt (20 mL) was added Silicycle Si-triamine Pd scavenger (Silicycle Inc.) and stirred vigorously for 1 hour. The reaction mixture was filtered and concentrated. The resulting pale yellow viscous oil was purified with radial chromatography and the less polar compound was determined to be ER-878894 (40 mg) which crystallized on standing.

I.D.6.: Preparation of ER-878895

Scheme XIV

As depicted in Scheme XIV above, a solution of ER-878894 (65 mg, 0.14 mmol) in 0.1N NaOH/MeOH (3 mL) was stirred for 30 minutes until all of the UV active spots disappeared by TLC. The solvent was removed in vacuo and the crude solid was dissolved in water (2 mL). The solution was neutralized with HCl and the solvent was removed in vacuo. The residue was purified by reverse phase preparative HPLC to afford ER-878895 (12 mg, 35%).

Table 1 provides analytical data for compounds described herein.

TABLE 1

| Analytical Data | | |
|---|---|---|
| Structure | ER-# | Analytical Data |
|  | 878617 Salt free | $^1$H NMR: (400 MHz, CDCl$_3$) δ 8.05 (m, 4H), 7.55 (m, 2H), 7.45 (m, 4H), 6.22 (t, J = 10.4 Hz), 5.95 (dd, J = 12.8, 10.6 Hz), 5.88-5.66 (m), 5.5 (m), 4.76(dd, J = 12.4, 3.6 Hz), 4.65 (m), 4.55 (m), 4.55 (dd, J = 12, 4.4 Hz), 4.36 (m), 3.94-3.64 (m) MS (ESI) m/z 473.31 (M + H)$^+$ |

TABLE 1-continued

| Analytical Data | | |
|---|---|---|
| Structure | ER-# | Analytical Data |
| BzO—[sugar with 2,2-diF, 3-OBz, N-diazepinone]  | 879381 Salt free | $^1$H NMR: (400 MHz, CDCl$_3$) δ 8.05 (m, 4H), 7.64 (m, 2H), 7.48 (m, 4H), 6.04 (dd, J = 12.0, 10.4 Hz, 1H), 5.76 (m, 2H), 5.58 (ddd, J = 12.0, 6.4, 5.2 Hz, 1H), 4.81(dd, J = 12.4, 3.6 Hz, 1H), 4.61 (dd, J = 12.8, 4.4 Hz, 1H), 4.58 (broad, partially overlap with 4.61 peaks, 1H), 4.43 (dt, J = 6.4, 3.4 Hz, 1H), 3.99-3.71 (m, 4H) |
| HO—[sugar with 2,2-diF, 3-OH, N-diazepinone] | 876437 Salt free | $^1$H NMR: (400 MHz, CD$_3$OD) δ 5.83 (m, 2H), 5.69 (dd, J = 21.2, 8.0 Hz, 1H), 4.05 (ddd, J = 14.0, 11.2, 8.4 Hz, 1H), 3.86-3.58 (m, 7H) MS (ESI) m/z 265.17 (M + H)$^+$ |
| BzO—[sugar with 2-F, 3-OBz, NHBoc] | 878890 Salt free | $^1$H NMR: (400 MHz, CDCl$_3$) δ 8.11-8.00 (m, 4H), 7.66-7.53 (m, 2H), 7.52-7.40 (m, 4H), 5.86 (dd, J = 16, 10 Hz, 1H), 5.57 (d, J = 18 Hz, 1H), 5.41 (s, 1H), 5.30 (s, 1H), 5.23 (d, J = 50 Hz, 1 H), 4.60 (s, 2H), 1.47 (s, 9H) |
| BzO—[sugar with 2-F, 3-OBz, N(Boc)(allyl)] | 878891 Salt free | $^1$H NMR: (400 MHz, CDCl$_3$) δ 8.08 (d, J = 7.6 Hz, 2H), 8.05 (d, J = 8.0 Hz, 2H), 7.62 (t, J = 7.6 Hz, 1H), 7.56 (t, J = 7.6 Hz, 1H), 7.46 (m, 4H), 6.0 (dd, J = 18.4, 4.4 Hz, 1H), 5.88 (m, 1H), 5.71 (dt, J = 19.6, 3.2 Hz, 1H), 5.48 (d, J = 52 Hz, 1H), 5.18 (d, J = 17.2 Hz, 1H), 5.14 (d, J = 10.8 Hz, 1H), 4.61 (broad s, 3H), 3.93 (m, 2H), 1.47 (s, 9H) |
| BzO—[sugar with 2-F, 3-OBz, N(allyl)C(O)NH-allyl] | 878892 Salt free | $^1$H NMR: (400 MHz, CDCl$_3$) δ 8.11-8.00 (m, 4H), 7.66-7.53 (m, 2H), 7.52-7.40 (m, 4H), 6.35 (dd, J = 26, 3 Hz, 1H), 6.06 (dd, J = 18, 5 Hz, 1H), 6.00-5.79 (m, 3H), 5.67 (dt, J = 19, 4 Hz, 1H), 5.58-5.50 (m, 1H), 5.44-4.95 (m, 8H), 4.74-4.53 (m, 4H), 4.01-3.97 (m, 2H), 3.91-3.83 (m, 3H), 1.71 (s, 1H) |
| BzO—[sugar with 2-F, 3-OBz, N-(N'-Bz-diazepinone)] | 878894 Salt free | $^1$H NMR: (400 MHz, CDCl$_3$) δ 8.12 (dd, J = 8.2, 1.2 Hz, 2H), 7.98 (dd, J = 8.2, 1.2 Hz, 2H), 7.6 (m, 5H), 7.45, (m, 6H), 5.93 (dd, J = 24.4, 3 Hz, 1H), 5.79 (s, 2H), 5.59 (dd, J = 18.6, 3.2 Hz, 1H), 5.14 (dd, J = 50.8, 2.8 Hz, 1H), 4.85 (d, J = 18.8 Hz, 1H), 4.81 (dd, J = 12, 3.8 Hz, 1H), 4.72 (dd. J = 12, 4.8 Hz, 1H), 4.35 (m, 2H), 4.17 (m, 2H) MS (ESI) m/z 559.2 (M + H)$^+$ |
| HO—[sugar with 2-F, 3-OH, N-diazepinone] | 878895 Salt free | $^1$H NMR: (400 MHz, D$_2$O) δ 5.8 (m, 2H), 5.7 (dd, J = 18.4, 5.2 Hz, 1H), 4.93 (ddd, J = 53, 5.2, 3.8 Hz, 1H), 4.19 (ddd, J = 22.8, 6.4, 3.6 Hz, 1H), 3.84-3.61 (m, 7H) MS (ESI) m/z 247.11 (M + H)$^+$ |

Example II

Assay for Inhibition of Cytidine Deaminase (CDA)

The cytidine deaminase (CDA) enzymatic assay described by Cacciamani, T. et al., *Arch. Biochem. Biophys.* 1991, 290, 285-92; Cohen R. et al., *J. Biol. Chem.*, 1971, 246, 7566-8; and Vincenzetti S. et al., *Protein Expr. Purif.* 1996, 8, 247-53 was used to determine the inhibitory activity ($IC_{50}$) of compounds described herein. Using this assay, the $IC_{50}$ of these compounds was determined by following the decrease of substrate (cytidine) caused by the deamination reaction catalyzed by CDA. Disappearance of substrate (cytidine) over time was monitored by the absorbance at 280 nm of the reaction.

The assay reaction was carried out in potassium phosphate buffer (pH 7.4, 20 mM, containing 1 mM DTT) in a total volume of 100 µl in a 96-well plate format. The final reaction mixture contained cytidine (50 µM) and purified human recombinant CDA. Purified enzyme was diluted so as to produce an absorbance change of approximately 2 milli-absorbance units/minute. Base line measurements of absorbance change over time were made before substrate (cytidine) addition. After substrate addition, absorbance change was read every minute for 30 minutes with a FlexStation® 3 (Molecular Devices, Sunnyvale, Calif.). For each compound, 8 different concentrations (10 µM, 3.33 µM, 1.11 µM, 0.37 µM, 0.12 µM, 0.041 µM, and 0.014 µM, and 0.0047 µM) were used to inhibit the reaction. The slopes of the absorbance change over time in each reaction were calculated and used by the SoftMax® Pro 5 software (Molecular Devices, Sunnyvale, Calif.) to obtain $IC_{50}$ values.

TABLE 2

Inhibitory Potency of Test Compounds

| Structure | ER-Number | $IC_{50}$ (nM) |
|---|---|---|
| (structure) | 876437 | 237 ± 86, n = 4 |
| (structure) | 876400 | 101 ± 53, n = 4 |
| (structure) | 878519 | 1616 ± 643, n = 3 |
| (structure) | 878895 | 140, n = 1 |
| (structure) | 876404 | 113, n = 2 |

Example III

Pharmacokinetics of ER-876437 and ER-876400 in Mice after Iv and PO Administrations ER-876437 and ER-876400 were both administered to mice at 10 mg/kg intravenously (IV) via the tail vein, and at 10 mg/kg per os (PO, or, orally) via gastric gavage. All doses were prepared in phosphate buffered saline (PBS) and were administered at a volume of 5 mL/kg. Five mice per group were used in these studies. Blood samples were taken serially from the tail vein of each mouse at predetermined timepoints. Blood samples from all mice in each group were pooled together prior to processing for plasma. The pooled blood samples were spun down within 30-60 minutes after withdrawal and the plasma was harvested and frozen for assay. After preparation and extraction the samples were assayed by LC/MS/MS. The observed concentrations (ng/mL), are reported in Table 3 below.

TABLE 3

Plasma concentrations (ng/mL) of ER-876437 and ER-876400 in mice after IV and PO administrations

| | ER-876437 | | ER-876400 | |
|---|---|---|---|---|
| Time (hr) | IV | PO | IV | PO |
| 0.167 | 11838 | 8597 | 19860 | 7101 |
| 0.5 | 7686 | 3720 | 10166 | 7859 |
| 1 | 3469 | 4179 | 4206 | 4665 |
| 2 | 1450 | 1145 | 1753 [a] | 1750 |
| 4 | 214 | 146 | 495 [a] | 320 |
| 6 | 184 | 36 | 118 | 87 |
| 8 | 64 | 103 | 59 | 44 |
| 24 | 20 | 39 | 93 | 264 |

[a] Above the quantitation limit

The pharmacokinetic (PK) parameters of ER-876437 and ER-876400 were calculated via non-compartmental analysis using Watson® v. 7.2. The resulting PK parameters are presented in Tables 4 and 5 below:

TABLE 4

PK parameters of ER-876437 and ER-876400 in mice after IV administrations

| Parameter | Units | ER-876437 | ER-876400 |
|---|---|---|---|
| Dose | mg/kg | 10.0 | 10.0 |
| $t_{1/2}$ | hr | 6.1 | 16.1 |
| $AUC_{0-t}$ | ng·hr/mL | 12893 | 18838 |
| $AUC_{0-\infty}$ | ng·hr/mL | 13071 | 20999 |
| $AUC_{0-\infty}/D$ | ng·hr/mL/D | 1307 | 2100 |
| $AUC_{Extrap}$ | % | 1.4 | 10.3 |
| CL | L/kg/hr | 0.77 | 0.48 |
| Vss | L/kg | 1.64 | 3.2 |

TABLE 5

PK parameters of ER-876437 and ER-876400 in mice after PO administrations

| Parameter | Units | ER-876437 | ER-876400 |
|---|---|---|---|
| Dose | mg/kg | 10.0 | 10.0 |
| $C_{max}$ | ng/mL | 8597 | 7859 |
| $t_{max}$ | hr | 0.167 | 0.5 |
| $AUC_{0-t}$ | ng·hr/mL | 8579 | 13160 |
| $AUC_{0-\infty}$ | ng·hr/mL | 9499 | NC |
| $AUC_{0-\infty}/D$ | ng·hr/mL/D | 950 | NC |
| $AUC_{Extrap}$ | % | 9.7 | NC |
| $t_{1/2}$ | hr | 16.3 | NC |
| F | % | 66.5 $^a$ | 69.9$^a$ |

$^a$ Calculated based on $AUC_{0-t}$
NC = Not calculated due to insufficient data The results of the present study suggest that the PK profiles of ER-876437 and ER-876400 in male BALB-c mice are similar. Following 10 mg/kg IV the PK of both ER-876437 and ER-876400 may be characterized by moderate distribution ($V_{SS}$=1.64 and 3.20 L/kg, respectively), slow clearance (CL=0.77 and 0.48 L/hr/kg, respectively), and slow elimination ($t_{1/2}$=6.1 and 16.1 hr, respectively).

The overall exposures ($AUC_{0-\infty}$) after IV administration of ER-876437 and ER-876400 to mice were 13071 and 20999 ng·hr/mL, respectively, which resulted in dose-normalized exposures ($AUC_{0-\infty}/D$) of respectively 1307 and 2100 mL/g. Following 10 mg/kg PO, the $C_{max}$ of ER-876437 and ER-876400 were respectively 8597 and 7859 ng/mL, and were observed at a $t_{max}$ of respectively 1.0 and 2.0 hr. The $AUC_{0-t}$ after PO administration of 10 mg/kg were 8579 and 13160 ng·hr/mL for ER-876437 and ER-876400, respectively. The $AUC_{0-\infty}$ of ER-876437 was 9499 ng·hr/mL and the $t_{1/2}$ was 16.3 hr. Due to insufficient data in the terminal elimination phase these parameters could not be determined for ER-876400. In addition, the $t_{1/2}$ for ER-876437 after PO administration is roughly 2.5-fold higher that that after IV administration.

The bioavailabilies (F %) of ER-876437 and ER-876400 were similar: 66.5 and 69.9%, respectively.

In conclusion, the PK profiles of ER-876437 and ER-876400 in male BALB-c mice after a single IV or PO dose of 10 mg/kg are similar. It is noted, however, that under normal feeding conditions, mice have a high gastric pH of around 5. See Simpson, R. J. et al. "Forms of soluble iron in mouse stomach and duodenal lumen: significance for mucosal update," *British Journal of Nutrition*. 63:79-89 (1990), which is hereby wholly incorporated by reference.

Example IV

ER-876400 and ER-876437 Stability in Simulated Gastric Fluid at 37° C.

This example describes the stabilities of ER-876400 and ER-876437 in simulated gastric fluid having a pH of 1.45 at room temperature (~25° C.) and at 37° C. For humans, under fasted conditions, the gastric pH has been reported to range from 1.4 to 2.1. See Kararli, T. T. Comparison of the GI anatomy, physiology, and biochemistry of humans and commonly used laboratory animals. *BioPharm & DrugDispos.* 16:351-380, 1995, which is hereby wholly incorporated by reference. The gastric pH in fasted monkeys has been reported to have a similar range of 1-3. See Kondo, H. et al. Characteristics of the gastric pH profiles of unfed and fed cynomolgus monkeys as pharmaceutical product development subjects. *BioPharm & DrugDispos.* 24:45-51, 2003, which is hereby wholly incorporated by reference.

Materials: Simulated gastric fluid (SGF) was prepared by mixing the following into 100 mL of HPLC grade (or purified) water: 200 mg of sodium chloride and 1.87 mL of a 37.52% HCl stock solution.

Sample Preparation The initial (t=0) samples were prepared by respectively diluting ER-876400 or ER-876437 in water. All other samples were prepared by dissolving ~2 mg of analyte (either ER-876400 or ER-876437) in ~1.0 mL of simulated gastric fluid at 37° C.

The HPLC analyses were conducted using a Waters UPLC solvent delivery system with Corona CAD detection. The HPLC Column (Waters Atlantis HHS T3 2.1×100 mm, 1.8 um) was maintained at 40° C. and preequilibrated with a solution containing 98% water and 2% acetonitrile. The temperature controlled auto-sampler was maintained at 37° C. The flow rate for the Water/MeCN mobile phase was 0.65 mL/min, with a gradient following sample injection (5 µL) as follows:

| Gradient: | Time (min) | % Water | % MeCN |
|---|---|---|---|
| | 0-2 | 98 | 2 |
| | 2-2.5 | linear gradient from (98% Water/2% MeCN) to (60% Water/40% MeCN) | |
| | 2.5-3.5 | 60 | 40 |

Hence, in these HPLC-SGF degradation studies, a 5 µL aliquot was taken from the SGF/analyte solution at various times and loaded onto the HPLC column with the above described features and conditions. The Water/MeCN mobile phase was applied to the column with the above described flow rate and gradient and the HPLC chromatograms were collected. After 3.5 minutes, the column was reequilibrated with 98% water/2% MeCN for 1.5 minutes.

Figure 2:
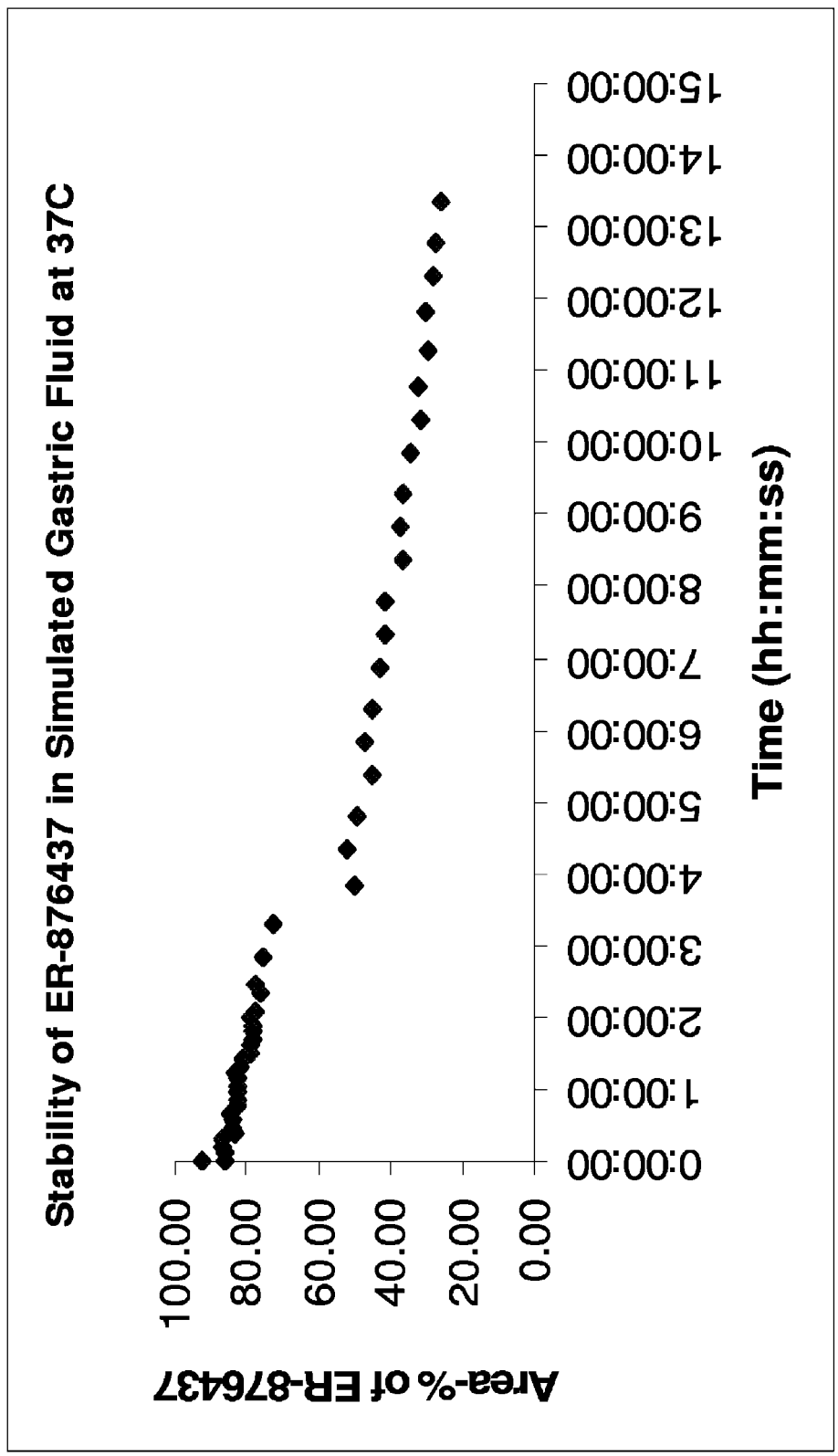
FIG. 2 shows a plot of total HPLC area-% purities of ER-876437 (1-((2R,4R,5R)-3,3-difluoro-4-hydroxy-5-(hydroxymethyl)tetrahydrofuran-2-yl)-3,4-dihydro-1H-1,3-diazepin-2(7H)-one) as a function of time in simulated gastric fluid at 37° C.

HPLC chromatograms of either ER-876400 or ER-876437 in water afforded identification of the peak attributed to ER-876400 or ER-876437. HPLC traces of SGF without any ER-876400 or ER-876437 provided blank (or background) chromatograms that could be used to identify SGF-related peaks and to distinguish those peaks from the analytes' peaks. Chromatograms were collected at the times identified in Tables 6 and 7, and the corresponding percentage of sample respectively attributed to either ER-876400 or ER-876437 are provide for each sampling time. These results are also depicted as plots in FIGS. 1 and 2.

TABLE 6

Stability of ER-876400 in SGF at 37° C.

| Analysis Time (hours:minutes:seconds) | % ER-876400 (peak retention time: 1.46 min) |
| --- | --- |
| 0:00:00 | 84.04 |
| 0:00:30 | 19.59 |
| 0:06:08 | 17.04 |
| 0:11:45 | 16.72 |
| 0:17:23 | 15.17 |
| 0:23:01 | 14.20 |
| 0:28:38 | 13.23 |
| 0:34:16 | 12.51 |
| 0:39:54 | 14.05 |
| 0:45:33 | 11.42 |
| 0:51:10 | 10.71 |
| 0:56:48 | 8.87 |
| 1:02:27 | 9.14 |
| 1:08:07 | 8.81 |
| 1:13:46 | 7.66 |
| 1:19:23 | 4.05 |
| 1:25:01 | 6.44 |
| 1:30:38 | 5.92 |
| 1:36:16 | 5.72 |
| 1:41:53 | 5.69 |
| 1:47:32 | 4.98 |
| 1:53:10 | 4.51 |
| 1:58:49 | 3.85 |
| 2:04:28 | 3.59 |
| 2:21:24 | 2.82 |
| 2:49:37 | 1.52 |
| 3:17:48 | 0.81 |
| 3:23:28 | 0.62 |
| 3:46:00 | 0.39 |
| 3:51:38 | 0.25 |

TABLE 7

Stability of ER-876437 in SGF at 37° C.

| Analysis Time (Hours:Minutes:Seconds) | % ER-876437 (peak retention time: 2.90 min) |
| --- | --- |
| 0:00:00 | 92.18 |
| 0:00:30 | 85.88 |
| 0:06:08 | 85.72 |
| 0:11:45 | 86.46 |
| 0:17:24 | 86.38 |
| 0:23:02 | 83.22 |
| 0:28:39 | 83.48 |
| 0:34:17 | 83.80 |
| 0:39:54 | 84.16 |
| 0:45:32 | 82.62 |
| 0:51:10 | 82.41 |
| 0:56:47 | 82.45 |
| 1:02:26 | 82.45 |
| 1:08:04 | 82.55 |
| 1:13:41 | 83.11 |
| 1:19:19 | 81.82 |
| 1:24:56 | 81.24 |
| 1:30:33 | 79.20 |
| 1:36:10 | 79.14 |
| 1:41:47 | 78.47 |
| 1:47:24 | 77.88 |
| 1:53:02 | 78.29 |
| 1:58:39 | 78.56 |
| 2:04:16 | 77.21 |
| 2:21:12 | 76.06 |
| 2:26:50 | 77.34 |
| 2:49:21 | 75.34 |
| 3:17:30 | 72.37 |
| 3:51:16 | 50.13 |
| 4:19:26 | 51.88 |
| 4:47:38 | 48.95 |
| 5:21:25 | 45.19 |
| 5:49:35 | 47.44 |
| 6:17:45 | 44.94 |
| 6:51:31 | 43.29 |
| 7:19:40 | 41.85 |
| 7:47:22 | 41.72 |
| 8:21:11 | 36.89 |
| 8:49:19 | 37.52 |
| 9:17:30 | 36.34 |
| 9:51:17 | 34.61 |
| 10:19:29 | 31.94 |
| 10:47:39 | 32.33 |
| 11:15:53 | 29.85 |
| 11:49:44 | 29.94 |
| 12:17:54 | 27.99 |
| 12:46:10 | 27.39 |
| 13:20:01 | 26.14 |

Conclusion: In simulated gastric fluid at 37° C., ER-876400 was found to degrade by 50% in less than 30 seconds while ER-876437 has a half-life of roughly 4-6 hours.

Example V

Effect of ER-876437 on a Non-Decitabine CDA Substrate in Survival Murine Lymphoma L1210 Model This study may be employed to determine whether ER-876437 enhances the oral efficacy of a non-decitabine CDA substrate (or prodrug thereof) in the L1210 survival model in mice.

Preparation of L1210 Cells: L1210 ascitic cells may be prepared by passaging them in mice at least three times as follows. Each CD2F1 female mouse may be intraperitoneally (IP) injected with about $10^5$ L1210 ascitic cells. After one week, the mouse may be sacrificed (asphyxiation via $CO_2$). After sacrificing, the mouse may be placed on its back, its belly surface may be cleaned with alcohol wipes, and a small incision may be made into the peritoneal cavity. 2 ml of ice cold 2.1% BSA in saline may be injected into the cavity and then the fluid may be withdrawn and transferred with an 18 G 3 cc syringe into a clean sterile tube and kept on ice. The fluid may be diluted 1:10 in 2.1% BSA in saline and one drop of Zap oglobin II lytic reagent (available from Beckman Coulter, Inc.) may be added to 1 ml of diluted ascites. Diluted ascites (diluted 1:10 again) may be counted on a hematocytometer and the number of cells per mL may be calculated. About $10^5$ L1210 cells may be used for a subsequent passage for another mouse passage. Or, a stock of L1210 ascites in BSA solution may be diluted to $1 \times 10^4$ cells/0.1 ml for use in the study mice.

Preparation of Study Mice: CD2F1 6-7 weeks old female mice may be randomly separated into groups such as those identified in Table 8. The mice may be prepared with intravenous (IV) injection of L1210 ascites (prepared as described above) one day prior to commencing the dosing. Mice may be injected with 0.1 ml of cell solution via caudal vein with a 27 G needle.

Mice may be dosed with vehicle or ER-876437 per os (PO, i.e., orally) 30 minutes prior to dosing with non-decitabine CDA substrate. ER-876437 may be prepared at 1 mg/ml in PBS and then diluted to 0.1 mg/ml, 0.01 mg/ml and 0.001 mg/ml in PBS for the lower doses.

A non-decitabine CDA substrate may be prepared at a 1 mg/ml stock in PBS and appropriately diluted to achieve a 0.01 mg/ml dosing solution. ER-876437 may be prepared at the beginning of each day of dosing and stored at 4° C. The non-decitabine CDA substrate may be prepared fresh twice a day, just prior to dosing. All solutions may be stored on ice while dosing. Mice may be dosed (intraperitoneally (IP) or per os (orally, PO)) twice a day (8 hours apart) for 4 consecutive days. A proposed final dosing scheme and proposed total non-decitabine CDA substrate (NDCS) and ER-876437 dose is outlined in Table 8. In the proposed dosing scheme, mice may be dosed (with vehicle, ER-876437 or NDCS) orally, intraperitoneally, or intravenously.

TABLE 8

Proposed Dosing Scheme

| Group # | Drug | NDCS Dose (rte Adm) | Cumulative NDCS Dose | ER-876437 Dose | Cumulative ER-876437 Dose |
|---|---|---|---|---|---|
| 1 | Vehicle | Veh | 0 mg/kg | Veh | 0 mg/kg |
| 2 | ER-876437 | Veh | 0 mg/kg | 10 mg/kg | 80 mg/kg |
| 3 | NDCS | 0.1 mg/kg | 0.8 mg/kg | Veh | 0 mg/kg |
| 4 | NDCS/ER-876437 | 0.1 mg/kg | 0.8 mg/kg | 0.01 mg/kg | 0.08 mg/kg |
| 5 | NDCS/ER-876437 | 0.1 mg/kg | 0.8 mg/kg | 0.1 mg/kg | 0.8 mg/kg |
| 6 | NDCS/ER-876437 | 0.1 mg/kg | 0.8 mg/kg | 1 mg/kg | 8 mg/kg |
| 7 | NDCS/ER-876437 | 0.1 mg/kg | 0.8 mg/kg | 10 mg/kg | 80 mg/kg |

Survival and Autopsy: Mice may be observed for survival and weighed daily for the duration of the study (30 days). Dead mice may be autopsied and observed for the presence of tumors in organs. Tumor deaths may be determined by liver weights greater than 1.6 g and spleen weights greater than 150 mg as per Covey J M and Zaharko D S, Eur J Cancer Clin Oncol, Vol. 21 p. 109-117, 1985.

Conclusions regarding whether co-administration of ER-876437 with a non-decitabine CDA substrate enhances survival as compared to administration of the non-decitabine CDA substrate alone in the L1210 survival model in mice may then be determined from the resulting data.

Example VI

In Vivo Efficacy Study of ER-876437 and Gemcitabine in A2780 Human Ovarian Cancer Xenograft Model This study evaluated the enhancing activity of ER-876437 on oral gemcitabine treatment in an A2780 human ovarian cancer xenograft model. ER-876437 was dosed 30 minutes prior to gemcitabine and both compounds were dosed orally. Animals were dosed daily from Monday to Friday for two weeks.

Materials and Methods

ER-876437 and gemcitabine-HCl (Gemzar® injectable, Eli Lilly) were formulated into 0.5% methyl cellulose (Sigma). Female nude mice (NU/NU, strain code 088, 6 weeks old, Charles River Laboratory) were implanted subcutaneously with $5 \times 10^6$ A2780 cancer cells per mouse. On day 13 when the tumors were approximately 150 mm³, treatment started as described in Table 9.

TABLE 9

Dosing Scheme for gemcitabine and ER-876437

| Group | Treatment | gemcitabine (PO, qdx5 for two weeks) | ER-876437* (PO, qdx5 for two weeks) |
|---|---|---|---|
| 1 | vehicle (0.5% methyl cellulose) | | |
| 2 | gemcitabine | 1 mg/kg | |
| 3 | ER-876437 | | 10 mg/kg |
| 4 | ER-876437*/gemcitabine | 1 mg/kg | 10 mg/kg |

*ER-876437 was dosed approximately 30 minutes prior to gemcitabine

Tumor volume and regressions were followed over time. Tumor volume was calculated by (length×width²)/2. Note that a complete regression was defined as no measurable tumor for at least 3 consecutive measurements; while a partial regression was defined as tumor shrinkage to equal or less than 50% of original tumor volume for 3 consecutive measurements. Tumor growth delay (TGD) was defined as the median number of days for the control and treatment groups to grow to 342.14 mm³. The average tumor volume on the first day of treatment (day 13) is 171.07 mm³. Hence, twice as much as the initial tumor size is 342.14 mm³.

Figure 3:
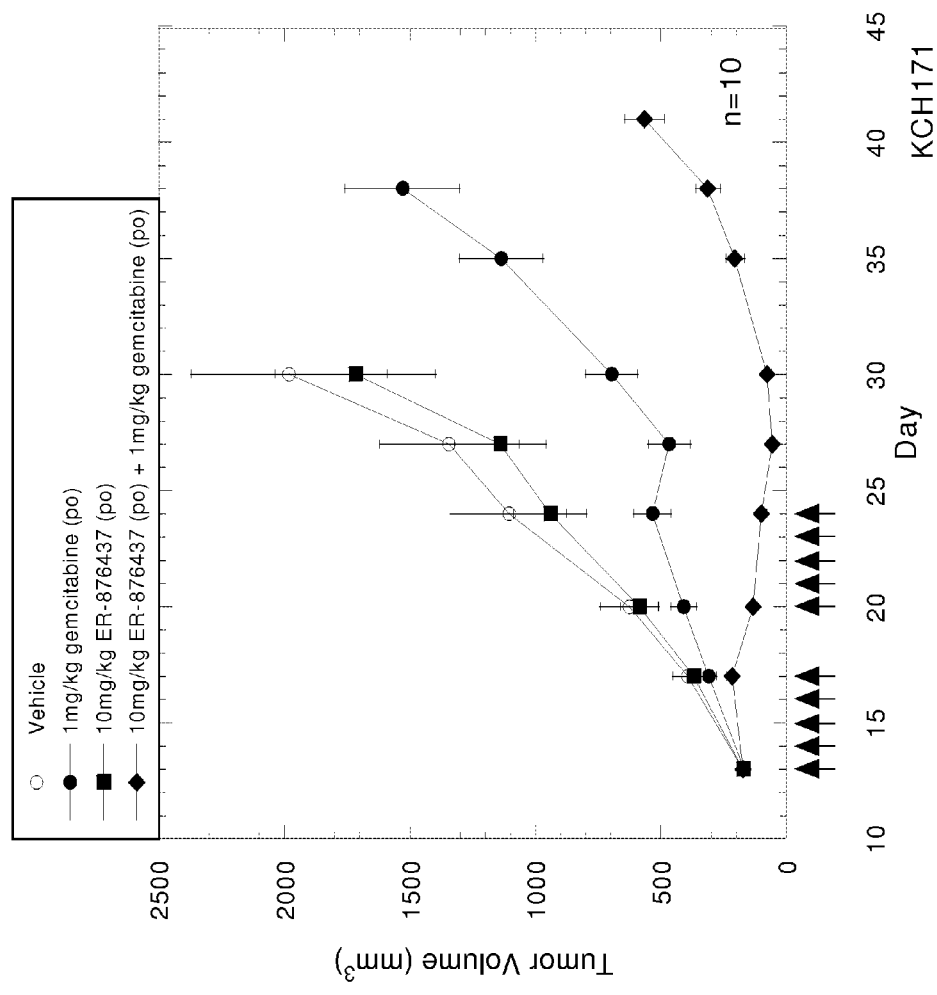
FIG. 3 shows the effect of combining gemcitabine (1 mg/kg) PO and ER-876437 (10 mg/kg) PO in the A2780 human ovarian cancer xenograft model.

Results:

ER-876437 alone (Group 3) had no effect at all on tumor growth (FIG. 3). Oral administration of gemcitabine in the regimen of 1 mg/kg PO qdx5 for two weeks (Group 2) showed limited efficacy after second week of treatment (FIG. 3), while ER-876437 alone (Group 3) did not show any efficacy during the whole treatment period (FIG. 3). When tumor doubling time is used to define the tumor growth delay (TGD), both gemcitabine alone (Group 2) and ER-876437 alone (Group 3) showed merely 2 days delay as compared to vehicle (Group 1) (Table 10). There is no statistically significant difference amongst Groups 1, 2 and 3 (Mann-Whitney test, GraphPad Prism 5, La Jolla, Calif.), with no regressions or tumor free survivors at day 41.

In contrast, when ER-876437 was administered approximately 30 minutes prior to gemcitabine (Group 4), one out of 10 mice (10%) showed complete regression and was a tumor free survivor at the study termination day (day 41). 3 out of 10 mice (30%) also showed partial tumor regression. These results show that there is therapeutic efficacy observed in the ER-876437/gemcitabine combination (Group 4) as compared to vehicle (Group 1), or as compared to gemcitabine alone (Group 2) (FIG. 3). Significant difference in TGD is observed when comparing this combination (Group 4) to gemcitabine alone (Group 2) (P=0.0001, Mann-Whitney test, GraphPad Prism 5, La Jolla. Calif., Table 10).

TABLE 10

Effect of Combination Treatment of Oral Gemcitabine and Oral ER-876437 on Tumor Growth Delay in the A2780 Ovarian Cancer Model.

| Treatment | TGD† | P value* |
|---|---|---|
| Vehicle | NA | |
| 1 mg/kg gemcitabine | 2 days | |
| 10 mg/kg ER-876437 | 2 days | |
| 1 mg/kg gemcitabine + 10 mg/kg ER-876437 | 23 days | 0.0001 |

Note:
†TGD, tumor growth delay.
*Mann-Whitney test was used to assess whether tumor growth delay differ significantly between gemcitabine alone group and ER-876437 plus gemcitabine combination group.

Conclusion:

Pre-treatment of ER-876437 showed significant enhancement of therapeutic activity of oral gemcitabine in this study. Significant tumor growth delay in the combination group compared to oral gemcitabine alone was identified with the Mann-Whitney statistical test (GraphPad Prism 5, La Jolla, Calif.).

Example VII

Effect of ER-876437 on the Half-Life of Gemcitabine in the Presence of CDA in Tris-HCl Buffer at 37° C.

This example describes the effect of ER-876437 on the half-life ($T_{1/2}$) of gemcitabine in the presence of cytidine deaminase (CDA) in Tris-HCl buffer at 37° C.

Materials and Equipment

This Example employed a Phenomenex Luna C18(2) HPLC column (100 Å 4.6×250 mm 5 μm). The solvent delivery system employed an HPLC quaternary pump, low pressure mixing. An autosampler having a variable loop, 0.1 to 100 μL range and temperature controlled thermostat was used. The UV detector can employ a dual wavelength detector, a diode array detector, a variable wavelength detector or equivalent, and can be recorded using chromatographic software (e.g., Waters Empower 2 Build 2154, Agilent ChemStation software version A.09.03 or higher for HPLC or equivalent). The analytical balance employed was capable of weighing ±0.1 mg. Degassed HPLC grade water and degassed HPLC grade acetonitrile were used as solvents for the mobile phases.

Diluting solution used to make the below solutions was Tris-HCl (37° C., ph 7.4, Boston BioProducts). Diluting solution also served as the blank for the UV spectra.

Gemcitabine Standard Control: 0.2 mM gemcitabine control was prepared by weighing 2.6 mg of gemcitabine in a 10 mL volumetric flask. The flask was diluted to volume with Tris-HCl buffer stored at 37° C. and mixed by inversion. Solution was labeled as gemcitabine stock solution. 1.0 mL of gemcitabine stock solution was transferred to a 5 mL volumetric flask and diluted to volume with the diluting solution and mixed by inversion.

ER-876437 Standard Control: 0.4 mM ER-876437 control was prepared by weighing 5.2 mg of ER-876437 in a 10 mL volumetric flask. The flask was diluted to volume with Tris-HCl buffer stored at 37° C. and mixed by inversion. Solution was labeled as ER-876437 stock solution. 1.0 mL of ER-876437 stock solution was transferred to a 5 mL volumetric flask and diluted to volume with the diluting solution and mixed by inversion.

Gemcitabine with CDA: 1.0 mL of gemcitabine stock solution was transferred to a 5 mL volumetric flask. Approximately 2-3 mL of diluting solution was transferred to the flask. 0.125 mL of CDA solution was transferred to the flask and diluted to volume with diluting solution. The sample was mixed by inversion and injected into the HPLC immediately after preparing.

Gemcitabine with CDA and ER-876437: 1.0 mL of ER-876437 stock solution was transferred to a 5 mL volumetric flask. Approximately 2 mL of diluting solution was transferred to the flask. 0.125 mL of CDA solution was transferred to the flask. 1.0 mL of gemcitabine stock solution was transferred to the same flask and diluted to volume with diluting solution. The sample was mixed by inversion and injected into the HPLC immediately after preparing.

HPLC Parameters: The above solutions were run on an HPLC column using the parameters shown in Table 11.

TABLE 11

HPLC Parameters

| | | | |
|---|---|---|---|
| Column Temperature: | | 25° C. | |
| Autosampler Temperature: | | 37° C. | |
| Flow rate: | | 1.0 mL/min. Flow rate may be adjusted ±0.2 mL/min to obtain specified retention times. | |
| Gradient: | Time, min | %-Solvent A* | %-Solvent B* |
| | Initial | 96 | 4 |
| | 10 | 96 | 4 |
| | 20 | 75 | 25 |
| | 25 | 75 | 25 |
| Re-equilibration time | | 10 minutes | |
| Injection volume: | | 25 μL | |
| Needle Wash Solution: | | Use the diluting solution | |
| Detection: | | 205 nm UV | |
| Run Time: | | 25 minutes | |

*Solvent A: water; solvent B: acetonitrile

The retention time for gemcitabine was found to be approximately 8 minutes; and the retention time of ER-876437 was found to be approximately 21.8 minutes.

Results and Discussion

TABLE 12

Summary of Results

| Solutions | Estimated $T_{1/2}$ |
|---|---|
| Gemcitabine with CDA in Tris-HCl buffer at 37° C. | <35 minutes |
| Gemcitabine with CDA and ER-876437 in Tris-HCl buffer at 37° C. | More than 13 h |

The levels of gemcitabine, in the presence and absence of CDA, with or without ER-876437, in Tris-HCl buffer at 37° C. were measured by HPLC analysis using UV detection. The areas of the gemcitabine and ER-876437 peaks in the experimental samples were measured and compared to the areas of the gemcitabine and ER-876437 time zero injections, respectively. Results were reported as percent remaining or control.

Figure 4:
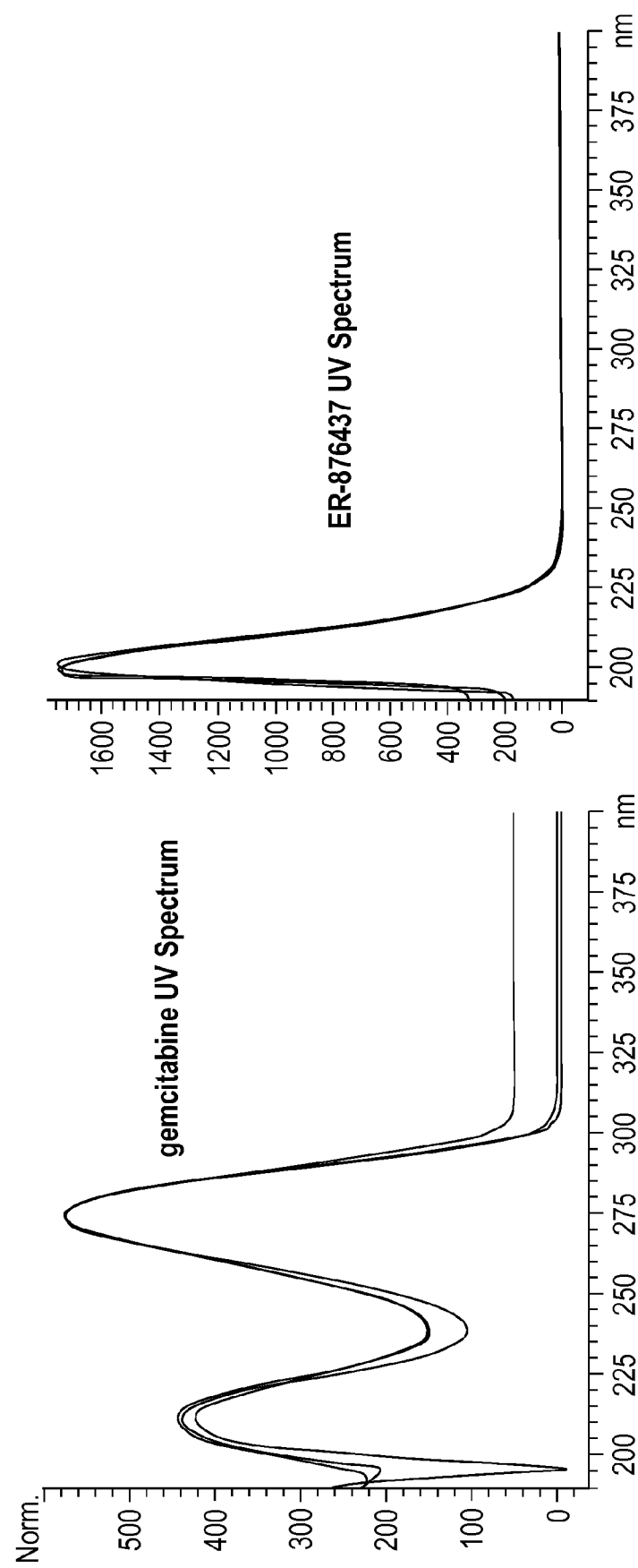
FIG. 4 shows the UV spectrum of gemcitabine and ER-876437.
Figure 5:
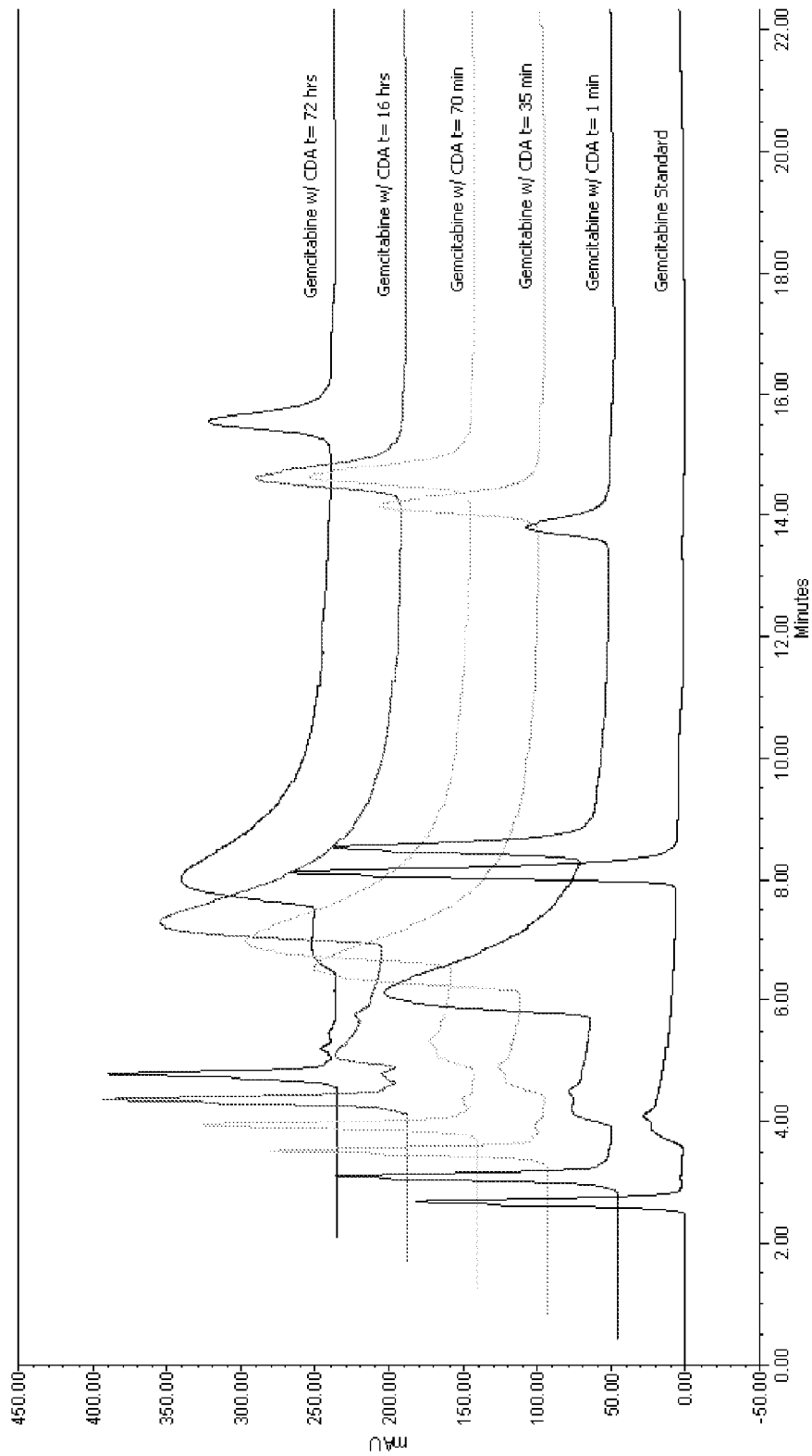
FIG. 5 shows HPLC chromatograms of gemcitabine in the presence of CDA in Tris-HCl buffer at 37° C. at selected time points.
Figure 6:
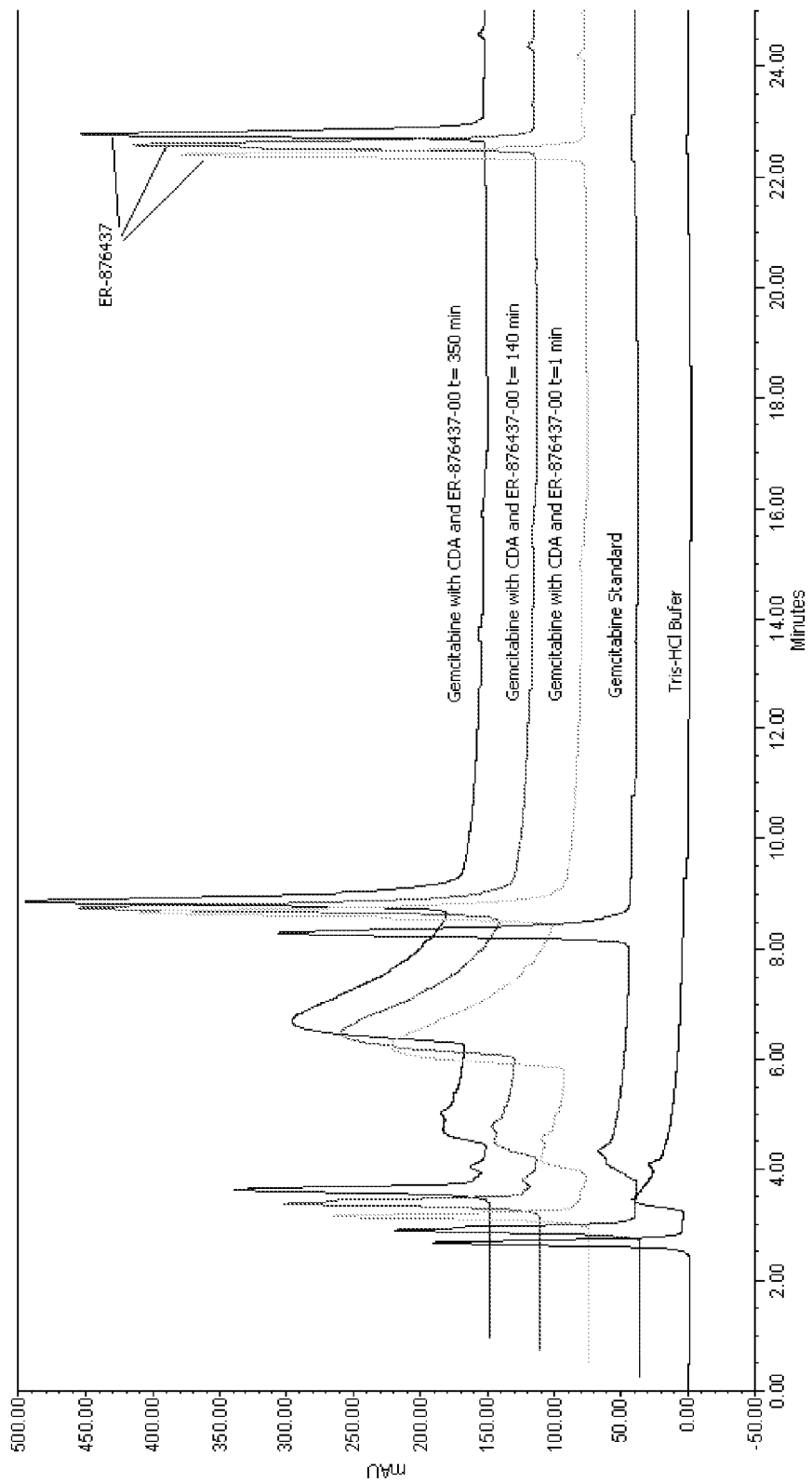
FIG. 6 shows HPLC chromatograms of gemcitabine in the presence of CDA and ER-876437 in Tris-HCl buffer at 37° C. at selected time points.

Data was collected at 205 nm UV because gemcitabine and ER-876437 share this UV maximum. See FIG. 4. Results were captured every 35 minutes for 12 hours and intermittently thereafter due to the length of the analytical method. HPLC chromatograms showing overlaid traces at specified time points are shown in FIG. 5 and FIG. 6.

HPLC chromatograms in these figures are shown with a constant, additive offset for clarity. Although the bottom trace is shown starting at time=0.00 minutes, each successive chromatogram is arbitrarily shifted to the right of the previous chromatogram (by a constant amount of time) so as to avoid having the peaks overlap. The actual times associated with the peaks shown in these chromatograms can be realized by shifting the start of the chromatogram trace (at the left hand side) back to the vertical axis where time equals 0.00 minutes. Similarly, the actual UV absorption of any peak can be realized by shifting the baseline of the chromatogram to the position where mAU=0.00.

Figure 7:
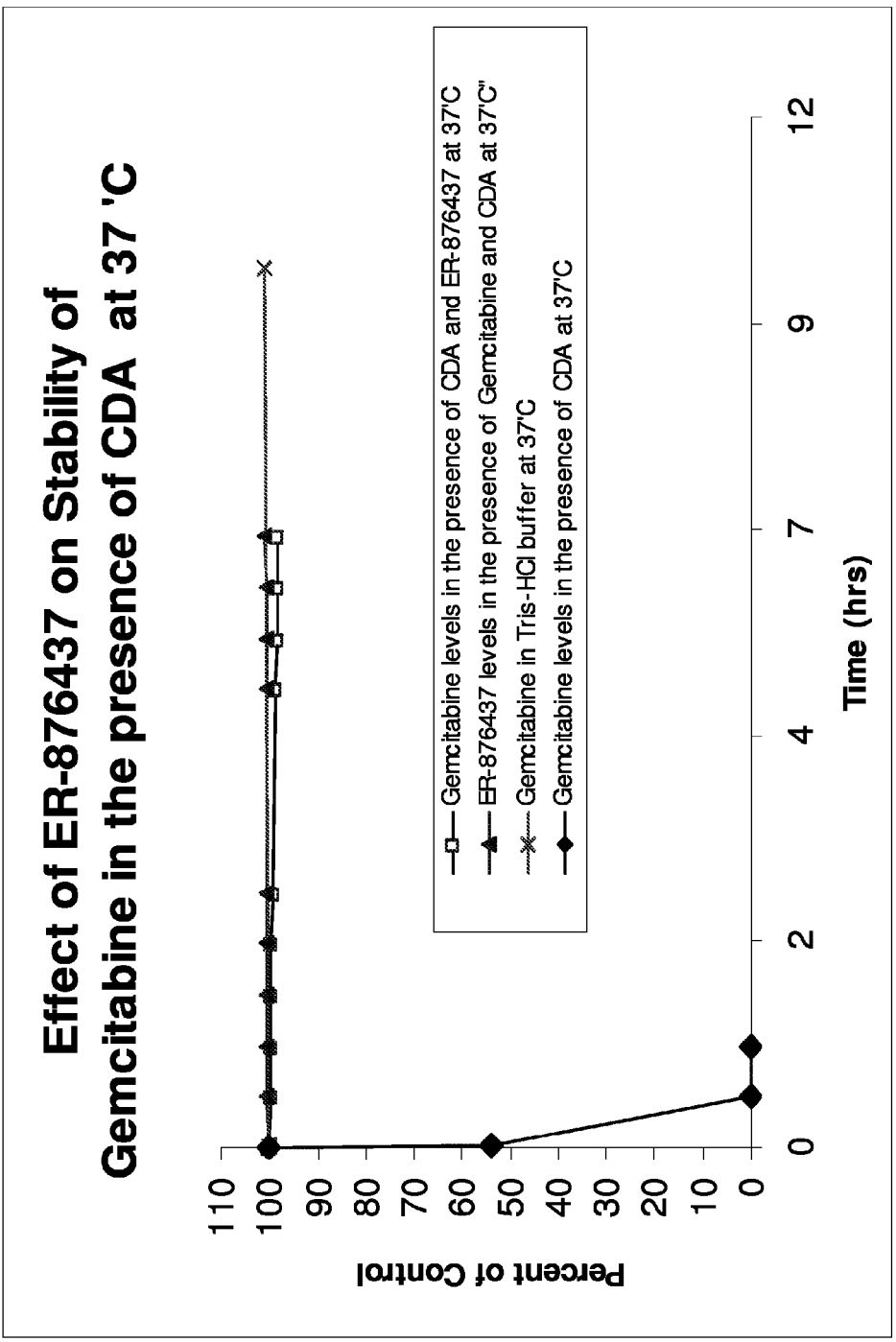
FIG. 7 shows the effect of ER-876437 on the levels of gemcitabine in the presence of CDA in Tris-HCl buffer at 37° C.

In the absence of CDA, no reduction in the gemcitabine concentration was observed after 10 hours, while, in the presence of CDA, the concentration of gemcitabine was reduced to nearly 0% control within 1 hour and the $T_{1/2}$ was found to be <35 minutes. Addition of ER-876437 to the incubation mixture resulted in inhibition of the reaction with greater than 95% of gemcitabine remaining after 7 h. Similarly, the levels of ER-876437 were not affected after 7 hours of exposure to CDA with gemcitabine. A summary of all the results are shown in FIG. 7.

In conclusion, the $T_{1/2}$ of gemcitabine in the presence of CDA in Tris-HCl buffer at 37° C. was found to be <35 minutes. ER-876437 nearly completely inhibited this effect. Gemcitabine alone in Tris-HCl buffer at 37° C. did not show any degradation at the end of observation Example VIII Effect of ER-876437 on the Half-Life of Cytarabine in the Presence of CDA in Tris-HCl Buffer at 37° C.

This example describes the effect of ER-876437 on the half-life ($T_{1/2}$) of cytarabine (Sigma) in the presence of cytidine deaminase (CDA) in Tris-HCl buffer at 37° C.

With exceptions identified below, materials and equipment are the same as were described above for Example VII.

Diluting solution used to make the below solutions was Tris-HCl (37° C., ph 7.4, Boston BioProducts). Diluting solution also served as the blank for the UV spectra.

Cytarabine Standard Control: 0.2 mM cytarabine control was prepared by weighing 2.4 mg of cytarabine in a 10 mL volumetric flask. The flask was diluted to volume with Tris-HCl buffer stored at 37° C. and mixed by inversion. Solution was labeled as cytarabine stock solution. 1.0 mL of cytarabine stock solution was transferred to a 5 mL volumetric flask and diluted to volume with the diluting solution and mixed by inversion.

ER-876437 Standard Control: 0.4 mM ER-876437 control was prepared by weighing 5.2 mg of ER-876437 in a 10 mL volumetric flask. The flask was diluted to volume with Tris-HCl buffer stored at 37° C. and mixed by inversion. Solution was labeled as ER-876437 stock solution. 1.0 mL of ER-876437 stock solution was transferred to a 5 mL volumetric flask and diluted to volume with the diluting solution and mixed by inversion.

Cytarabine with CDA: 1.0 mL of cytarabine stock solution was transferred to a 5 mL volumetric flask. Approximately 2-3 mL of diluting solution was transferred to the flask. 0.125 mL of CDA solution was transferred to the flask and diluted to volume with diluting solution. The sample was mixed by inversion and injected into the HPLC immediately after preparing.

Cytarabine with CDA and ER-876437: 1.0 mL of ER-876437 stock solution was transferred to a 5 mL volumetric flask. Approximately 2 mL of diluting solution was transferred to the flask. 0.125 mL of CDA solution was transferred to the flask. 1.0 mL of cytarabine stock solution was transferred to the same flask and diluted to volume with diluting solution. The sample was mixed by inversion and injected into the HPLC immediately after preparing.

The above standards and samples were run on an HPLC column using the parameters shown in Table 11 of Example VII, except that UV spectra were collected at 205 and 275 nm. The retention time for cytarabine was found to be approximately 4.4 minutes; and the retention time of ER-876437 was found to be approximately 21.8 minutes.

Results and Discussion

TABLE 13

Summary of Results

| Solutions | Estimated $T_{1/2}$ |
|---|---|
| Cytarabine with CDA in Tris-HCl buffer at 37° C. | <35 minutes |
| Cytarabine with CDA and ER-876437 in Tris-HCl buffer at 37° C. | More than 52 h |

The levels of cytarabine, in the presence and absence of CDA, with or without ER-876437, in Tris-HCl buffer at 37° C. were measured by HPLC analysis using UV detection. The areas of the cytarabine and ER-876437 peaks in the stability samples were measured and compared to the areas of the cytarabine and ER-876437 standard controls, respectively. Results were reported as percent remaining of control.

Figure 8:
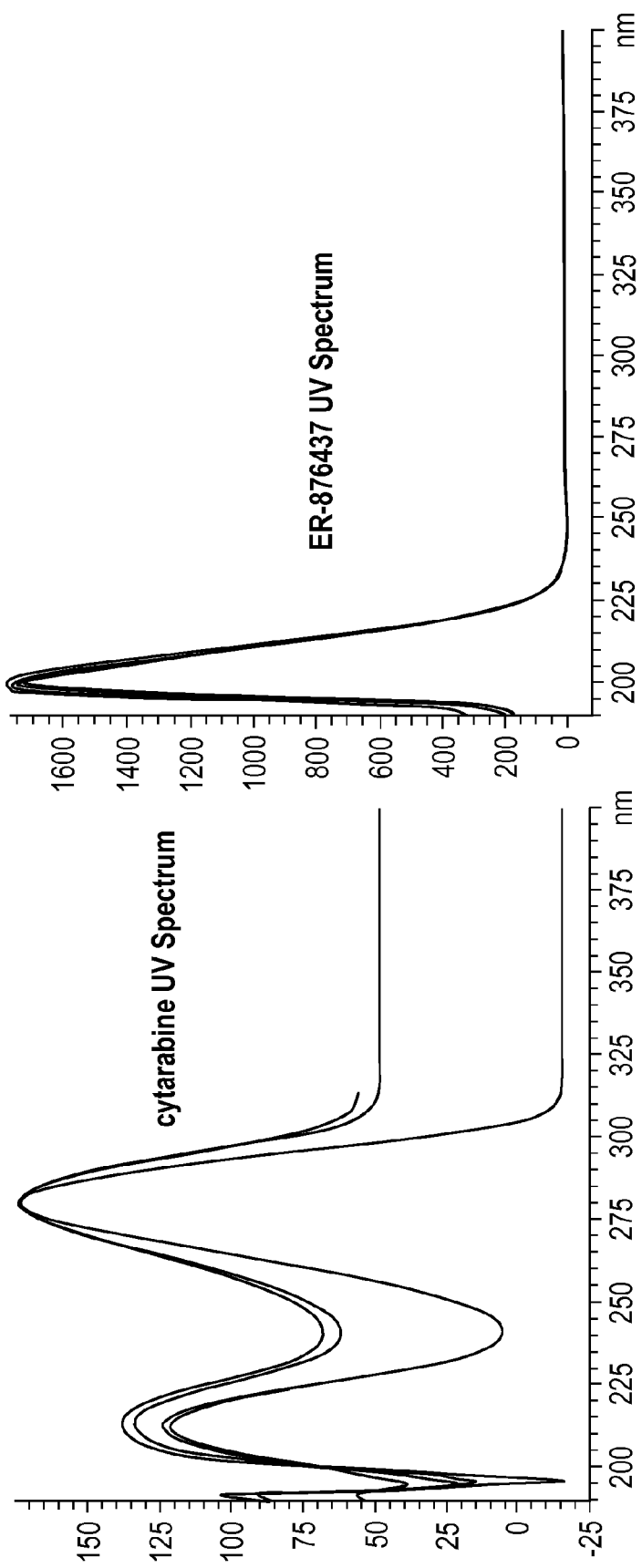
FIG. 8 shows the UV spectrum of cytaribine and ER-876437.

Since ER-876437 and cytarabine have different UV maxima, HPLC chromatograms were collected at 205 nm and 275 nm UV. Cytarabine results were calculated using 275 nm UV and ER-876437 results were calculated using 205 nm UV. See FIG. 8 for ER-876437 and cytarabine UV Spectra.

Results were captured every 35 minutes for 12 hours and intermittently thereafter due to the length of the analytical method. HPLC Chromatograms showing overlaid traces at specified time points are shown in FIGS. 9 and 10.

HPLC chromatograms in these figures are shown with a constant, additive offset for clarity. Although the bottom trace is shown starting at time=0.00 minutes, each successive chromatogram is arbitrarily shifted to the right of the previous chromatogram (by a constant amount of time) so as to avoid having the peaks overlap. The actual times associated with the peaks shown in these chromatograms can be realized by shifting the start of the chromatogram trace (at the left hand side) back to the vertical axis where time equals 0.00 minutes. Similarly, the actual UV absorption of any peak can be realized by shifting the baseline of the chromatogram to the position where mAU=0.00.

In the absence of CDA, no reduction in the cytarabine concentration was observed after 55 hours, while, in the presence of CDA, the concentration of cytarabine was reduced to nearly 0% control within 35 minutes and the $T_{1/2}$ was found to be <35 minutes. Addition of ER-876437 to the incubation mixture resulted in inhibition of the reaction with greater than 95% of cytarabine remaining after 52 h. Similarly, the levels of ER-876437 were not affected after 52 hours of exposure to CDA with cytarabine. A summary of all the results are shown in FIGS. 11 and 12.

In conclusion, the $T_{1/2}$ of cytarabine in the presence of CDA in Tris-HCl buffer at 37° C. was found to be <35 minutes. ER-876437 nearly completely inhibited this effect. Cytarabine alone in Tris-HCl buffer at 37 C did not show any degradation at the end of observation period (52 h).

All publications or patent applications described herein are hereby wholly incorporated by reference.

We claim:

1. A composition comprising a non-decitabine cytidine deaminase (CDA) substrate used for treating cancer and a compound of formula I:

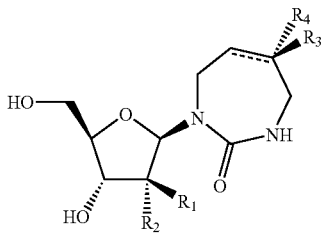

wherein:
one of $R_1$ and $R_2$ is F, and the other is selected from H and F;
one of $R_3$ and $R_4$ is H, and the other is selected from H and OH;
where - - - is a covalent bond or absent, and $R_4$ is absent when - - - is a covalent bond;
or a pharmaceutically acceptable salt, a $C_{1-6}$ alkyl ester or a $C_{2-6}$ alkenyl ester thereof.

2. The composition of claim 1, wherein said non-decitabine CDA substrate is selected from the group consisting of 5-azacytidine, ara-C, tezacitabine, 5-fluoro-2'-deoxycytidine, and cytochlor.

3. The composition of claim 1, wherein the compound of formula I is a compound of formula VIII:

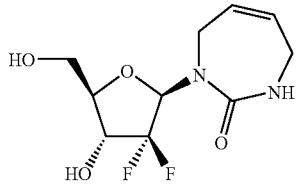

or a pharmaceutically acceptable salt, a $C_{1-6}$ alkyl ester, or a $C_{2-6}$ alkenyl ester thereof.

4. A method of treating a cancer being treated with a non-decitabine CDA substrate used for treating cancer comprising:
administering to a subject a composition comprising a non-decitabine CDA substrate used for treating cancer; and
administering to a subject a composition comprising a compound of formula I:

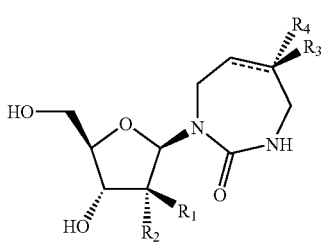

wherein:
one of $R_1$ and $R_2$ is F, and the other is selected from H and F;

one of $R_3$ and $R_4$ is H, and the other is selected from H and OH;
where - - - is a covalent bond or absent, and $R_4$ is absent when - - - is a covalent bond;
or a pharmaceutically acceptable salt, a $C_{1-6}$ alkyl ester, or a $C_{2-6}$ alkenyl ester thereof.

5. The method of claim 4, wherein said non-decitabine CDA substrate is selected from the group consisting of 5-azacytidine, ara-C, tezacitabine, 5-fluoro-2'-deoxycytidine, and cytochlor.

6. The method of claim 4, wherein said cancer is selected from the group consisting of hematological cancers and solid cancers.

7. The method of claim 6, wherein said cancer is a hematological cancer selected from the group consisting of myelodysplastic syndrome, acute myeloid leukemia and chronic myeloid leukemia.

8. The method of claim 6, wherein the cancer is a solid cancer selected from the group consisting of pancreatic cancer, ovarian cancer, peritoneal cancer, non small cell lung cancer, metastatic breast cancer, bladder cancer, transitional cell carcinoma, biliary tract cancer, gallbladder carcinoma, fallopian tube cancer, squamous cell carcinoma of the head and neck, hepatocellular carcinoma, liver tumor, lung carcinoma, uterine cervix tumor and colon cancer.

9. The method of claim 4, wherein the compound is a compound of formula VIII:

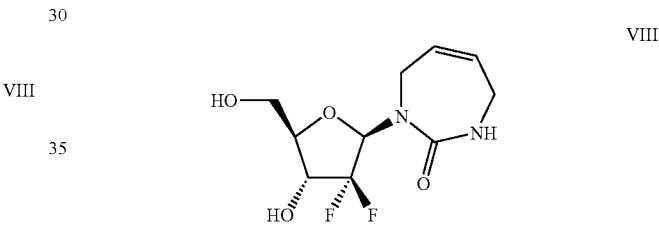

or a pharmaceutically acceptable salt, a $C_{1-6}$ alkyl ester, or a $C_{2-6}$ alkenyl ester thereof.

10. The method of claim 9, wherein said cancer is selected from the group consisting of hematological cancers and solid cancers.

11. The method of claim 10, wherein said cancer is a hematological cancer selected from the group consisting of myelodysplastic syndrome, acute myeloid leukemia and chronic myeloid leukemia.

12. The composition of claim 1, wherein the non-decitabine CDA substrate is gemcitabine.

13. The composition of claim 12, wherein the compound of formula I is a compound of formula VIII:

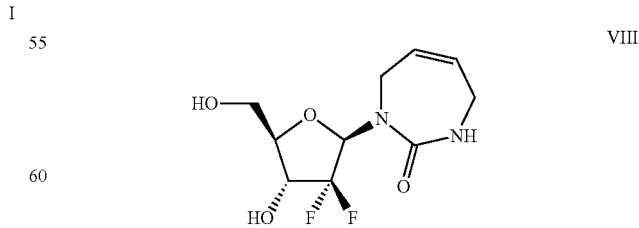

or a pharmaceutically acceptable salt, a $C_{1-6}$ alkyl ester, or a $C_{2-6}$ alkenyl ester thereof.

14. The method of claim 4, wherein said non-decitabine CDA substrate is gemcitabine.

15. The method of claim 14, wherein the compound is a compound of formula VIII:

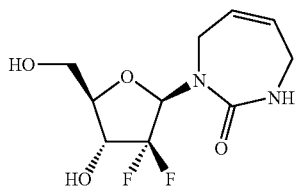

VIII or a pharmaceutically acceptable salt, a $C_{1-6}$ alkyl ester, or a $C_{2-6}$ alkenyl ester thereof.

16. A pharmaceutical composition comprising
(i) a non-decitabine CDA substrate used for treating cancer;
(ii) a compound of formula I:

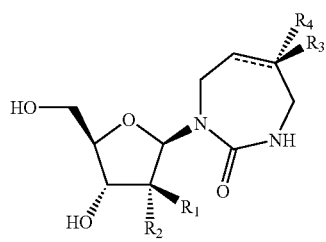

I wherein:
one of $R_1$ and $R_2$ is F, and the other is selected from H and F;
one of $R_3$ and $R_4$ is H, and the other is selected from H and OH;
where - - - is a covalent bond or absent, and $R_4$ is absent when - - - is a covalent bond;
or a pharmaceutically acceptable salt, a $C_{1-6}$ alkyl ester or a $C_{2-6}$ alkenyl ester thereof; and
(iii) a pharmaceutically acceptable excipient.

17. The pharmaceutical composition of claim 16, wherein said non-decitabine CDA substrate is selected from the group consisting of 5-azacytidine, ara-C, tezacitabine, 5-fluoro-2'-deoxycytidine, gemcitabine, and cytochlor.

18. A pharmaceutical composition of claim 16, wherein the compound of formula I is a compound of formula VIII:

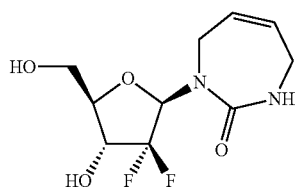

VIII or a pharmaceutically acceptable salt, a $C_{1-6}$ alkyl ester or a $C_{2-6}$ alkenyl ester thereof.

19. The method according to claim 4, wherein the composition comprising a non-decitabine CDA substrate used for treating cancer and the composition comprising a compound of formula I are simultaneously administered.

20. The method according to claim 4, wherein the composition comprising a non-decitabine CDA substrate used for treating cancer and the composition comprising a compound of formula I are sequentially administered.

* * * * *

UNITED STATES PATENT AND TRADEMARK OFFICE
CERTIFICATE OF CORRECTION

PATENT NO. : 8,329,665 B2
APPLICATION NO. : 12/755116
DATED : December 11, 2012
INVENTOR(S) : Belyakov et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 97 days.

Signed and Sealed this
Twenty-eighth Day of May, 2013

Teresa Stanek Rea
*Acting Director of the United States Patent and Trademark Office*